United States Patent
Zhang et al.

(10) Patent No.: US 11,566,051 B2
(45) Date of Patent: Jan. 31, 2023

(54) STABILIZED RSV F PROTEINS AND USES THEREOF

(71) Applicants: Merck Sharp & Dohme Corp., Rahway, NJ (US); Lan Zhang, Chalfont, PA (US); Arthur Fridman, East Norriton, PA (US); Eberhard Durr, Quakertown, PA (US); Andrew Bett, Lansdale, PA (US)

(72) Inventors: Lan Zhang, Chalfont, PA (US); Arthur Fridman, East Norriton, PA (US); Eberhard Durr, Quakertown, PA (US); Andrew Bett, Lansdale, PA (US)

(73) Assignee: Merck Sharp & Dohme LLC, Rahway, NJ (US)

(*) Notice: Subject to any disclaimer, the term of this patent is extended or adjusted under 35 U.S.C. 154(b) by 197 days.

(21) Appl. No.: 16/964,118

(22) PCT Filed: Jan. 24, 2019

(86) PCT No.: PCT/US2019/014873
§ 371 (c)(1),
(2) Date: Jul. 22, 2020

(87) PCT Pub. No.: WO2019/147749
PCT Pub. Date: Aug. 1, 2019

(65) Prior Publication Data
US 2021/0300971 A1   Sep. 30, 2021

Related U.S. Application Data

(60) Provisional application No. 62/623,184, filed on Jan. 29, 2018.

(51) Int. Cl.
| | | |
|---|---|---|
| *C07K 14/135* | (2006.01) | |
| *A61K 39/155* | (2006.01) | |
| *C12N 7/00* | (2006.01) | |
| *A61K 39/00* | (2006.01) | |

(52) U.S. Cl.
CPC .......... *C07K 14/135* (2013.01); *A61K 39/155* (2013.01); *C12N 7/00* (2013.01); *A61K 2039/54* (2013.01); *A61K 2039/55505* (2013.01); *A61K 2039/55555* (2013.01); *C12N 2760/18534* (2013.01)

(58) Field of Classification Search
None
See application file for complete search history.

(56) References Cited

U.S. PATENT DOCUMENTS

| 2004/0096451 A1 | 5/2004 | Young et al. |
| 2018/0311336 A1 * | 11/2018 | Ciaramella ............. A61P 37/04 |

FOREIGN PATENT DOCUMENTS

| RU | 2012105308 A | 8/2013 | |
| WO | 2011008974 A2 | 1/2011 | |
| WO | 2014160463 | 10/2014 | |
| WO | 2017075124 A1 | 5/2017 | |
| WO | 2017109629 A1 | 6/2017 | |
| WO | 2017172890 A1 | 10/2017 | |
| WO | WO-2017172890 A1 * | 10/2017 | ............. A61K 39/12 |

OTHER PUBLICATIONS

Flynn, Jessica A. et al., Stability Characterization of a Vaccine Antigen Based on the Respiratory Syncytial Virus Fusion Glycoprotein, PLoS One, 2016, 1-18, 11(10): e0164789.

Zhang, Lan et al., Design and characterization of a fusion glycoprotein vaccine for Respiratory Syncytial Virus with improved stability, Vaccine, 2018, 8119-8130, 36.

Anez, German et al., Passage of Dengue Virus Type 4 Vaccine Candidates in Fetal Rhesus Lung Cells Selects Heparin-Sensitive Variants That Result in Loss of Infectivity and Immunogenicity in Rhesus Macaques, Journal of Virology, 2009, 10384-10394, 83(20).

Chen, Xiaoying et al., Fusion Protein Linkers: Property, Design and Functionality, Adv. Drug Deliv. Rev., 2013, 1357-1369, 65.

Maeda, Yumi et al., Engineering of Functional Chimeric Protein G-Vargula Luciferase, Analytical Biochemistry, 1997, 147-152, 249.

Collins, Peter L., Nucleotide sequence of the gene encoding the fusion (F) glycoprotein of human respiratory syncytial virus, Proc. Natl. Acad. Sci. USA, 1984, 7683-7687, vol. 81, No. 24.

Pakula, Andrew A., Genetic Analysis of Protein Stability and Function, Annu. Rev. Genet., 1989, 289-310, 23.

Tokuriki, Nobuhiko et al., Stability effects of mutations and protein evolvability, Curr Opin Structural Biol, 2009, 596-604, 19.

* cited by examiner

*Primary Examiner* — Shanon A. Foley
*Assistant Examiner* — Myron G Hill
(74) *Attorney, Agent, or Firm* — Nichole M. Valeyko; Alysia Finnegan

(57) ABSTRACT

The disclosure relates to stable RSV F proteins and immunogenic compositions containing the same, as well as methods of using the immunogenic compositions and compositions comprising the RSV F proteins.

16 Claims, 27 Drawing Sheets

Specification includes a Sequence Listing.

SEQUENCE LISTING

```
<160> NUMBER OF SEQ ID NOS: 49

<210> SEQ ID NO 1
<211> LENGTH: 8
<212> TYPE: PRT
<213> ORGANISM: Artificial Sequence
<220> FEATURE:
<223> OTHER INFORMATION: Amino Acid Linker

<400> SEQUENCE: 1

Gly Gly Gly Ser Gly Gly Gly Ser
1               5

<210> SEQ ID NO 2
<211> LENGTH: 10
<212> TYPE: PRT
<213> ORGANISM: Artificial Sequence
<220> FEATURE:
<223> OTHER INFORMATION: Amino Acid Linker

<400> SEQUENCE: 2

Gly Gly Gly Ser Gly Gly Gly Ser Gly Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Amino Acid Linker

<400> SEQUENCE: 3

Gly Gly Gly Ser Gly Gly Gly Ser Gly Gly Gly Ser
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Amino Acid Linker

<400> SEQUENCE: 4

Gly Gly Gly Ser Gly Gly Gly Ser Gly Gly Gly Ser Gly Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: TEV Cleavage Site

<400> SEQUENCE: 5
```

```
Glu Asn Leu Tyr Phe Gln Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Strep Tag

<400> SEQUENCE: 6

Trp Ser His Pro Gln Phe Glu Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Thrombin Cleavage Site

<400> SEQUENCE: 7

Leu Val Pro Arg Gly Ser
1               5

<210> SEQ ID NO 8
<211> LENGTH: 31
<212> TYPE: PRT
<213> ORGANISM: Artificial Sequence
<220> FEATURE:
<223> OTHER INFORMATION: Foldon

<400> SEQUENCE: 8

Ser Ala Ile Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu
                20                  25                  30

<210> SEQ ID NO 9
<211> LENGTH: 25
<212> TYPE: PRT
<213> ORGANISM: Artificial Sequence
<220> FEATURE:
<223> OTHER INFORMATION: Signal Sequence

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly
                20                  25

<210> SEQ ID NO 10
<211> LENGTH: 574
<212> TYPE: PRT
<213> ORGANISM: Artificial Sequence
<220> FEATURE:
<223> OTHER INFORMATION: RSV F reference sequence

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
450                 455                 460
```

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Val Ile Ile Val Ile Leu Leu Ser Leu Ile Ala Val
530                 535                 540

Gly Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 11
<211> LENGTH: 556
<212> TYPE: PRT
<213> ORGANISM: Artificial Sequence
<220> FEATURE:
<223> OTHER INFORMATION: Peptide construct

<400> SEQUENCE: 11

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

```
Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Gly Tyr Ile Pro Glu Ala Pro Arg Asp Gly Gln Ala Tyr Val Arg
    530                 535                 540

Lys Asp Gly Glu Trp Val Leu Leu Ser Thr Phe Leu
545                 550                 555

<210> SEQ ID NO 12
<211> LENGTH: 605
<212> TYPE: PRT
<213> ORGANISM: Artificial Sequence
<220> FEATURE:
<223> OTHER INFORMATION: Peptide construct

<400> SEQUENCE: 12

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
```

```
                    485                 490                 495
Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Gly Tyr Ile Pro Glu Ala Pro Arg Asp Gly Gln Ala Tyr Val Arg
        530                 535                 540

Lys Asp Gly Glu Trp Val Leu Leu Ser Thr Phe Leu Glu Asn Leu Tyr
545                 550                 555                 560

Phe Gln Ser Trp Ser His Pro Gln Phe Glu Lys Gly Gly Ser Gly
                565                 570                 575

Gly Gly Ser Gly Gly Gly Ser Trp Ser His Pro Gln Phe Glu Lys Gly
            580                 585                 590

Ser Gly Ser Gly Ser His His His His His His
        595                 600                 605

<210> SEQ ID NO 13
<211> LENGTH: 544
<212> TYPE: PRT
<213> ORGANISM: Artificial Sequence
<220> FEATURE:
<223> OTHER INFORMATION: Peptide construct

<400> SEQUENCE: 13

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

```
                    245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Cys Ile Ile Lys Glu Glu Val Leu Ala Tyr Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
            485                 490                 495
Glu Lys Ile Asn Gln Ser Leu Ala Phe Ile Arg Lys Ser Asp Glu Leu
            500                 505                 510
Leu Ser Ala Ile Gly Gly Tyr Ile Pro Glu Ala Pro Arg Asp Gly Gln
            515                 520                 525
Ala Tyr Val Arg Lys Asp Gly Glu Trp Val Leu Leu Ser Thr Phe Leu
            530                 535                 540
```

<210> SEQ ID NO 14
<211> LENGTH: 503
<212> TYPE: PRT
<213> ORGANISM: Artificial Sequence
<220> FEATURE:
<223> OTHER INFORMATION: Peptide Construct

<400> SEQUENCE: 14

```
Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Asn Lys Cys Asn Gly Thr Asp Ala Lys Val Lys Leu Ile Lys
```

```
                65                  70                  75                  80
Gln Glu Leu Asp Lys Tyr Lys Asn Ala Val Thr Glu Leu Gln Leu Leu
                    85                  90                  95

Met Gly Gly Ser Gly Gly Ser Ala Ile Ala Ser Gly Val Ala
                    100                 105                 110

Val Cys Lys Val Leu His Leu Glu Gly Val Asn Lys Ile Lys Ser
                115                 120                 125

Ala Leu Leu Ser Thr Asn Lys Ala Val Val Ser Leu Ser Asn Gly Val
130                 135                 140

Ser Val Leu Thr Phe Lys Val Leu Asp Leu Lys Asn Tyr Ile Asp Lys
145                 150                 155                 160

Gln Leu Leu Pro Ile Leu Asn Lys Gln Ser Cys Ser Ile Ser Asn Ile
                165                 170                 175

Glu Thr Val Ile Glu Phe Gln Gln Lys Asn Asn Arg Leu Leu Glu Ile
                180                 185                 190

Thr Arg Glu Phe Ser Val Asn Ala Gly Val Thr Thr Pro Val Ser Thr
            195                 200                 205

Tyr Met Leu Thr Asn Ser Glu Leu Leu Ser Leu Ile Asn Asp Met Pro
210                 215                 220

Ile Thr Asn Asp Gln Lys Lys Leu Met Ser Asn Asn Val Gln Ile Val
225                 230                 235                 240

Arg Gln Gln Ser Tyr Ser Ile Met Cys Ile Ile Lys Glu Glu Val Leu
                245                 250                 255

Ala Tyr Val Val Gln Leu Pro Leu Tyr Gly Val Ile Asp Thr Pro Cys
                260                 265                 270

Trp Lys Leu His Thr Ser Pro Leu Cys Thr Thr Asn Thr Lys Glu Gly
            275                 280                 285

Ser Asn Ile Cys Leu Thr Arg Thr Asp Arg Gly Trp Tyr Cys Asp Asn
            290                 295                 300

Ala Gly Ser Val Ser Phe Phe Pro Gln Ala Glu Thr Cys Lys Val Gln
305                 310                 315                 320

Ser Asn Arg Val Phe Cys Asp Thr Met Asn Ser Leu Thr Leu Pro Ser
                325                 330                 335

Glu Val Asn Leu Cys Asn Val Asp Ile Phe Asn Pro Lys Tyr Asp Cys
                340                 345                 350

Lys Ile Met Thr Ser Lys Thr Asp Val Ser Ser Ser Val Ile Thr Ser
                355                 360                 365

Leu Gly Ala Ile Val Ser Cys Tyr Gly Lys Thr Lys Cys Thr Ala Ser
            370                 375                 380

Asn Lys Asn Arg Gly Ile Ile Lys Thr Phe Ser Asn Gly Cys Asp Tyr
385                 390                 395                 400

Val Ser Asn Lys Gly Val Asp Thr Val Ser Val Gly Asn Thr Leu Tyr
                405                 410                 415

Tyr Val Asn Lys Gln Glu Gly Lys Ser Leu Tyr Val Lys Gly Glu Pro
                420                 425                 430

Ile Ile Asn Phe Tyr Asp Pro Leu Val Phe Pro Ser Asp Glu Phe Asp
            435                 440                 445

Ala Ser Ile Ser Gln Val Asn Glu Lys Ile Asn Gln Ser Leu Ala Phe
450                 455                 460

Ile Arg Lys Ser Asp Glu Leu Leu Ser Ala Ile Gly Gly Tyr Ile Pro
465                 470                 475                 480

Glu Ala Pro Arg Asp Gly Gln Ala Tyr Val Arg Lys Asp Gly Glu Trp
                485                 490                 495
```

```
Val Leu Leu Ser Thr Phe Leu
            500

<210> SEQ ID NO 15
<211> LENGTH: 527
<212> TYPE: PRT
<213> ORGANISM: Artificial Sequence
<220> FEATURE:
<223> OTHER INFORMATION: Peptide construct

<400> SEQUENCE: 15

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Ser Ala Ile Ala Ser Gly Val Ala
            100                 105                 110

Val Cys Lys Val Leu His Leu Glu Gly Glu Val Asn Lys Ile Lys Ser
        115                 120                 125

Ala Leu Leu Ser Thr Asn Lys Ala Val Val Ser Leu Ser Asn Gly Val
    130                 135                 140

Ser Val Leu Thr Phe Lys Val Leu Asp Leu Lys Asn Tyr Ile Asp Lys
145                 150                 155                 160

Gln Leu Leu Pro Ile Leu Asn Lys Gln Ser Cys Ser Ile Ser Asn Ile
                165                 170                 175

Glu Thr Val Ile Glu Phe Gln Gln Lys Asn Asn Arg Leu Leu Glu Ile
            180                 185                 190

Thr Arg Glu Phe Ser Val Asn Ala Gly Val Thr Thr Pro Val Ser Thr
        195                 200                 205

Tyr Met Leu Thr Asn Ser Glu Leu Leu Ser Leu Ile Asn Asp Met Pro
    210                 215                 220

Ile Thr Asn Asp Gln Lys Lys Leu Met Ser Asn Asn Val Gln Ile Val
225                 230                 235                 240

Arg Gln Gln Ser Tyr Ser Ile Met Cys Ile Ile Lys Glu Glu Val Leu
                245                 250                 255

Ala Tyr Val Val Gln Leu Pro Leu Tyr Gly Val Ile Asp Thr Pro Cys
            260                 265                 270

Trp Lys Leu His Thr Ser Pro Leu Cys Thr Thr Asn Thr Lys Glu Gly
        275                 280                 285

Ser Asn Ile Cys Leu Thr Arg Thr Asp Arg Gly Trp Tyr Cys Asp Asn
    290                 295                 300

Ala Gly Ser Val Ser Phe Phe Pro Gln Ala Glu Thr Cys Lys Val Gln
305                 310                 315                 320

Ser Asn Arg Val Phe Cys Asp Thr Met Asn Ser Leu Thr Leu Pro Ser
                325                 330                 335

Glu Val Asn Leu Cys Asn Val Asp Ile Phe Asn Pro Lys Tyr Asp Cys
            340                 345                 350
```

```
Lys Ile Met Thr Ser Lys Thr Asp Val Ser Ser Val Ile Thr Ser
            355                 360                 365

Leu Gly Ala Ile Val Ser Cys Tyr Gly Lys Thr Lys Cys Thr Ala Ser
        370                 375                 380

Asn Lys Asn Arg Gly Ile Ile Lys Thr Phe Ser Asn Gly Cys Asp Tyr
385                 390                 395                 400

Val Ser Asn Lys Gly Val Asp Thr Val Ser Val Gly Asn Thr Leu Tyr
                405                 410                 415

Tyr Val Asn Lys Gln Glu Gly Lys Ser Leu Tyr Val Lys Gly Glu Pro
                420                 425                 430

Ile Ile Asn Phe Tyr Asp Pro Leu Val Phe Pro Ser Asp Glu Phe Asp
            435                 440                 445

Ala Ser Ile Ser Gln Val Asn Glu Lys Ile Asn Gln Ser Leu Ala Phe
        450                 455                 460

Ile Arg Lys Ser Asp Glu Leu Leu Ser Ala Ile Gly Gly Tyr Ile Pro
465                 470                 475                 480

Glu Ala Pro Arg Asp Gly Gln Ala Tyr Val Arg Lys Asp Gly Glu Trp
                485                 490                 495

Val Leu Leu Ser Thr Phe Leu Gly Gly Leu Val Pro Arg Gly Ser His
                500                 505                 510

His His His His His Ser Ala Trp Ser His Pro Gln Phe Glu Lys
            515                 520                 525

<210> SEQ ID NO 16
<211> LENGTH: 505
<212> TYPE: PRT
<213> ORGANISM: Artificial Sequence
<220> FEATURE:
<223> OTHER INFORMATION: Peptide construct

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190
```

```
Glu Ile Thr Arg Glu Phe Ser Val Asn Ala Gly Val Thr Thr Pro Val
            195                 200                 205

Ser Thr Tyr Met Leu Thr Asn Ser Glu Leu Leu Ser Leu Ile Asn Asp
        210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
        290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Leu Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
        370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
        450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu
            500                 505

<210> SEQ ID NO 17
<211> LENGTH: 529
<212> TYPE: PRT
<213> ORGANISM: Artificial Sequence
<220> FEATURE:
<223> OTHER INFORMATION: Peptide Construct

<400> SEQUENCE: 17

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

```
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                     85                  90                  95

Met Gly Gly Gly Ser Gly Gly Ser Gly Gly Ala Ile Ala Ser Gly
                100                 105                 110

Val Ala Val Cys Lys Val Leu His Leu Glu Gly Glu Val Asn Lys Ile
                115                 120                 125

Lys Ser Ala Leu Leu Ser Thr Asn Lys Ala Val Val Ser Leu Ser Asn
130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
                180                 185                 190

Glu Ile Thr Arg Glu Phe Ser Val Asn Ala Gly Val Thr Thr Pro Val
                195                 200                 205

Ser Thr Tyr Met Leu Thr Asn Ser Glu Leu Leu Ser Leu Ile Asn Asp
210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
                260                 265                 270

Pro Cys Trp Lys Leu His Thr Ser Pro Leu Cys Thr Thr Asn Thr Lys
                275                 280                 285

Glu Gly Ser Asn Ile Cys Leu Thr Arg Thr Asp Arg Gly Trp Tyr Cys
                290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Leu Thr Leu
                325                 330                 335

Pro Ser Glu Val Asn Leu Cys Asn Val Asp Ile Phe Asn Pro Lys Tyr
                340                 345                 350

Asp Cys Lys Ile Met Thr Ser Lys Thr Asp Val Ser Ser Ser Val Ile
                355                 360                 365

Thr Ser Leu Gly Ala Ile Val Ser Cys Tyr Gly Lys Thr Lys Cys Thr
                370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Gln Glu Gly Lys Ser Leu Tyr Val Lys Gly
                420                 425                 430

Glu Pro Ile Ile Asn Phe Tyr Asp Pro Leu Val Phe Pro Ser Asp Glu
                435                 440                 445

Phe Asp Ala Ser Ile Ser Gln Val Asn Glu Lys Ile Asn Gln Ser Leu
450                 455                 460
```

```
Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
                500                 505                 510

Ser His His His His His His Ser Ala Trp Ser His Pro Gln Phe Glu
            515                 520                 525

Lys
```

<210> SEQ ID NO 18
<211> LENGTH: 507
<212> TYPE: PRT
<213> ORGANISM: Artificial Sequence
<220> FEATURE:
<223> OTHER INFORMATION: Peptide construct

<400> SEQUENCE: 18

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Ser Gly Gly Ser Ala Ile Ala
            100                 105                 110

Ser Gly Val Ala Val Cys Lys Val Leu His Leu Glu Gly Glu Val Asn
            115                 120                 125

Lys Ile Lys Ser Ala Leu Leu Ser Thr Asn Lys Ala Val Val Ser Leu
130                 135                 140

Ser Asn Gly Val Ser Val Leu Thr Phe Lys Val Leu Asp Leu Lys Asn
145                 150                 155                 160

Tyr Ile Asp Lys Gln Leu Leu Pro Ile Leu Asn Lys Gln Ser Cys Ser
                165                 170                 175

Ile Ser Asn Ile Glu Thr Val Ile Glu Phe Gln Gln Lys Asn Asn Arg
            180                 185                 190

Leu Leu Glu Ile Thr Arg Glu Phe Ser Val Asn Ala Gly Val Thr Thr
        195                 200                 205

Pro Val Ser Thr Tyr Met Leu Thr Asn Ser Glu Leu Leu Ser Leu Ile
    210                 215                 220

Asn Asp Met Pro Ile Thr Asn Asp Gln Lys Lys Leu Met Ser Asn Asn
225                 230                 235                 240

Val Gln Ile Val Arg Gln Gln Ser Tyr Ser Ile Met Cys Ile Ile Lys
                245                 250                 255

Glu Glu Val Leu Ala Tyr Val Val Gln Leu Pro Leu Tyr Gly Val Ile
            260                 265                 270

Asp Thr Pro Cys Trp Lys Leu His Thr Ser Pro Leu Cys Thr Thr Asn
        275                 280                 285

Thr Lys Glu Gly Ser Asn Ile Cys Leu Thr Arg Thr Asp Arg Gly Trp
```

```
                290                 295                 300
Tyr Cys Asp Asn Ala Gly Ser Val Ser Phe Phe Pro Gln Ala Glu Thr
305                 310                 315                 320

Cys Lys Val Gln Ser Asn Arg Val Phe Cys Asp Thr Met Asn Ser Leu
                325                 330                 335

Thr Leu Pro Ser Glu Val Asn Leu Cys Asn Val Asp Ile Phe Asn Pro
            340                 345                 350

Lys Tyr Asp Cys Lys Ile Met Thr Ser Lys Thr Asp Val Ser Ser Ser
            355                 360                 365

Val Ile Thr Ser Leu Gly Ala Ile Val Ser Cys Tyr Gly Lys Thr Lys
        370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
                405                 410                 415

Asn Thr Leu Tyr Tyr Val Asn Lys Gln Glu Gly Lys Ser Leu Tyr Val
            420                 425                 430

Lys Gly Glu Pro Ile Ile Asn Phe Tyr Asp Pro Leu Val Phe Pro Ser
        435                 440                 445

Asp Glu Phe Asp Ala Ser Ile Ser Gln Val Asn Glu Lys Ile Asn Gln
    450                 455                 460

Ser Leu Ala Phe Ile Arg Lys Ser Asp Glu Leu Leu Ser Ala Ile Gly
465                 470                 475                 480

Gly Tyr Ile Pro Glu Ala Pro Arg Asp Gly Gln Ala Tyr Val Arg Lys
                485                 490                 495

Asp Gly Glu Trp Val Leu Leu Ser Thr Phe Leu
            500                 505

<210> SEQ ID NO 19
<211> LENGTH: 531
<212> TYPE: PRT
<213> ORGANISM: Artificial Sequence
<220> FEATURE:
<223> OTHER INFORMATION: Peptide construct

<400> SEQUENCE: 19

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Ser Ala Ile Ala
            100                 105                 110

Ser Gly Val Ala Val Cys Lys Val Leu His Leu Glu Gly Glu Val Asn
        115                 120                 125

Lys Ile Lys Ser Ala Leu Leu Ser Thr Asn Lys Ala Val Val Ser Leu
    130                 135                 140

Ser Asn Gly Val Ser Val Leu Thr Phe Lys Val Leu Asp Leu Lys Asn
```

Tyr Ile Asp Lys Gln Leu Leu Pro Ile Leu Asn Lys Gln Ser Cys Ser
145                 150                 155                 160

Ile Ser Asn Ile Glu Thr Val Ile Glu Phe Gln Gln Lys Asn Asn Arg
        165                 170                 175

Leu Leu Glu Ile Thr Arg Glu Phe Ser Val Asn Ala Gly Val Thr Thr
            180                 185                 190

Pro Val Ser Thr Tyr Met Leu Thr Asn Ser Glu Leu Leu Ser Leu Ile
        195                 200                 205

Asn Asp Met Pro Ile Thr Asn Asp Gln Lys Lys Leu Met Ser Asn Asn
210                 215                 220

Val Gln Ile Val Arg Gln Ser Tyr Ser Ile Met Cys Ile Ile Lys
225                 230                 235                 240

Glu Glu Val Leu Ala Tyr Val Val Gln Leu Pro Leu Tyr Gly Val Ile
            245                 250                 255

Asp Thr Pro Cys Trp Lys Leu His Thr Ser Pro Leu Cys Thr Thr Asn
        260                 265                 270

Thr Lys Glu Gly Ser Asn Ile Cys Leu Thr Arg Thr Asp Arg Gly Trp
    275                 280                 285

Tyr Cys Asp Asn Ala Gly Ser Val Ser Phe Phe Pro Gln Ala Glu Thr
290                 295                 300

Cys Lys Val Gln Ser Asn Arg Val Phe Cys Asp Thr Met Asn Ser Leu
305                 310                 315                 320

Thr Leu Pro Ser Glu Val Asn Leu Cys Asn Val Asp Ile Phe Asn Pro
            325                 330                 335

Lys Tyr Asp Cys Lys Ile Met Thr Ser Lys Thr Asp Val Ser Ser Ser
        340                 345                 350

Val Ile Thr Ser Leu Gly Ala Ile Val Ser Cys Tyr Gly Lys Thr Lys
    355                 360                 365

Cys Thr Ala Ser Asn Lys Asn Arg Gly Ile Ile Lys Thr Phe Ser Asn
370                 375                 380

Gly Cys Asp Tyr Val Ser Asn Lys Gly Val Asp Thr Val Ser Val Gly
385                 390                 395                 400

Asn Thr Leu Tyr Tyr Val Asn Lys Gln Glu Gly Lys Ser Leu Tyr Val
            405                 410                 415

Lys Gly Glu Pro Ile Ile Asn Phe Tyr Asp Pro Leu Val Phe Pro Ser
        420                 425                 430

Asp Glu Phe Asp Ala Ser Ile Ser Gln Val Asn Glu Lys Ile Asn Gln
    435                 440                 445

Ser Leu Ala Phe Ile Arg Lys Ser Asp Glu Leu Leu Ser Ala Ile Gly
450                 455                 460

Gly Tyr Ile Pro Glu Ala Pro Arg Asp Gly Gln Ala Tyr Val Arg Lys
465                 470                 475                 480

Asp Gly Glu Trp Val Leu Leu Ser Thr Phe Leu Gly Gly Leu Val Pro
            485                 490                 495

Arg Gly Ser His His His His His His Ser Ala Trp Ser His Pro Gln
        500                 505                 510

Phe Glu Lys
515                 520                 525

530

<210> SEQ ID NO 20
<211> LENGTH: 509
<212> TYPE: PRT
<213> ORGANISM: Artificial Sequence
<220> FEATURE:
<223> OTHER INFORMATION: Peptide construct

<400> SEQUENCE: 20

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Gly Ser Gly Ser Ala
            100                 105                 110

Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400
```

```
Ser Asn Gly Cys Asp Tyr Val Ser Asn Lys Gly Val Asp Thr Val Ser
            405                 410                 415

Val Gly Asn Thr Leu Tyr Tyr Val Asn Lys Gln Glu Gly Lys Ser Leu
        420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
            485                 490                 495

Arg Lys Asp Gly Glu Trp Val Leu Leu Ser Thr Phe Leu
            500                 505
```

<210> SEQ ID NO 21
<211> LENGTH: 533
<212> TYPE: PRT
<213> ORGANISM: Artificial Sequence
<220> FEATURE:
<223> OTHER INFORMATION: Peptide construct

<400> SEQUENCE: 21

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255
```

-continued

```
Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
        435                 440                 445

Pro Ser Asp Glu Phe Asp Ala Ser Ile Ser Gln Val Asn Glu Lys Ile
    450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His His Ser Ala Trp Ser His
        515                 520                 525

Pro Gln Phe Glu Lys
    530

<210> SEQ ID NO 22
<211> LENGTH: 509
<212> TYPE: PRT
<213> ORGANISM: Artificial Sequence
<220> FEATURE:
<223> OTHER INFORMATION: Peptide construct

<400> SEQUENCE: 22

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Glu Leu Gln Leu Leu
                85                  90                  95

Met Gly Gly Gly Ser Gly Gly Gly Ser Gly Gly Gly Ser Gly Ser Ala
            100                 105                 110

Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
        130                 135                 140

Cys Leu Ser Asn Gly Val Cys Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
        210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
        290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
        370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
        435                 440                 445

Pro Ser Asp Glu Phe Asp Ala Ser Ile Ser Gln Val Asn Glu Lys Ile
        450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495
```

-continued

```
Arg Lys Asp Gly Glu Trp Val Leu Leu Ser Thr Phe Leu
            500                 505
```

```
<210> SEQ ID NO 23
<211> LENGTH: 533
<212> TYPE: PRT
<213> ORGANISM: Artificial Sequence
<220> FEATURE:
<223> OTHER INFORMATION: Peptide construct

<400> SEQUENCE: 23

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Ser Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Cys Leu Ser Asn Gly Val Cys Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350
```

```
Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
        435                 440                 445

Pro Ser Asp Glu Phe Asp Ala Ser Ile Ser Gln Val Asn Glu Lys Ile
    450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His His Ser Ala Trp Ser His
        515                 520                 525

Pro Gln Phe Glu Lys
    530
```

<210> SEQ ID NO 24
<211> LENGTH: 509
<212> TYPE: PRT
<213> ORGANISM: Artificial Sequence
<220> FEATURE:
<223> OTHER INFORMATION: Peptide construct

<400> SEQUENCE: 24

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Gly Ser Gly Gly Ser Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175
```

```
Cys Ser Ile Ser Asn Ile Glu Thr Val Ile Glu Phe Gln Gln Lys Asn
                180                 185                 190

Asn Arg Leu Leu Glu Ile Thr Arg Glu Phe Ser Val Asn Ala Gly Val
            195                 200                 205

Thr Thr Pro Val Ser Thr Tyr Met Leu Thr Asn Ser Glu Leu Leu Ser
        210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
        435                 440                 445

Pro Ser Cys Glu Phe Asp Cys Ser Ile Ser Gln Val Asn Glu Lys Ile
    450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu
            500                 505

<210> SEQ ID NO 25
<211> LENGTH: 533
<212> TYPE: PRT
<213> ORGANISM: Artificial Sequence
<220> FEATURE:
<223> OTHER INFORMATION: Peptide construct

<400> SEQUENCE: 25

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30
```

```
Tyr Gln Ser Thr Cys Ser Ala Val Ser Lys Gly Tyr Leu Ser Ala Leu
         35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gly Gly Gly Ser Gly Gly Gly Ser Gly Gly Gly Ser Gly Ser Ala
            100                 105                 110
Ile Ala Ser Gly Val Ala Val Cys Lys Val Leu His Leu Glu Gly Glu
            115                 120                 125
Val Asn Lys Ile Lys Ser Ala Leu Leu Ser Thr Asn Lys Ala Val Val
    130                 135                 140
Ser Leu Ser Asn Gly Val Ser Val Leu Thr Phe Lys Val Leu Asp Leu
145                 150                 155                 160
Lys Asn Tyr Ile Asp Lys Gln Leu Leu Pro Ile Leu Asn Lys Gln Ser
                165                 170                 175
Cys Ser Ile Ser Asn Ile Glu Thr Val Ile Glu Phe Gln Gln Lys Asn
                180                 185                 190
Asn Arg Leu Leu Glu Ile Thr Arg Glu Phe Ser Val Asn Ala Gly Val
            195                 200                 205
Thr Thr Pro Val Ser Thr Tyr Met Leu Thr Asn Ser Glu Leu Leu Ser
    210                 215                 220
Leu Ile Asn Asp Met Pro Ile Thr Asn Asp Gln Lys Lys Leu Met Ser
225                 230                 235                 240
Asn Asn Val Gln Ile Val Arg Gln Gln Ser Tyr Ser Ile Met Cys Ile
                245                 250                 255
Ile Lys Glu Glu Val Leu Ala Tyr Val Val Gln Leu Pro Leu Tyr Gly
            260                 265                 270
Val Ile Asp Thr Pro Cys Trp Lys Leu His Thr Ser Pro Leu Cys Thr
            275                 280                 285
Thr Asn Thr Lys Glu Gly Ser Asn Ile Cys Leu Thr Arg Thr Asp Arg
    290                 295                 300
Gly Trp Tyr Cys Asp Asn Ala Gly Ser Val Ser Phe Phe Pro Gln Ala
305                 310                 315                 320
Glu Thr Cys Lys Val Gln Ser Asn Arg Val Phe Cys Asp Thr Met Asn
                325                 330                 335
Ser Leu Thr Leu Pro Ser Glu Val Asn Leu Cys Asn Val Asp Ile Phe
            340                 345                 350
Asn Pro Lys Tyr Asp Cys Lys Ile Met Thr Ser Lys Thr Asp Val Ser
            355                 360                 365
Ser Ser Val Ile Thr Ser Leu Gly Ala Ile Val Ser Cys Tyr Gly Lys
    370                 375                 380
Thr Lys Cys Thr Ala Ser Asn Lys Asn Arg Gly Ile Ile Lys Thr Phe
385                 390                 395                 400
Ser Asn Gly Cys Asp Tyr Val Ser Asn Lys Gly Val Asp Thr Val Ser
                405                 410                 415
Val Gly Asn Thr Leu Tyr Tyr Val Asn Lys Gln Glu Gly Lys Ser Leu
            420                 425                 430
Tyr Val Lys Gly Glu Pro Ile Ile Asn Phe Tyr Asp Pro Leu Val Phe
    435                 440                 445
Pro Ser Cys Glu Phe Asp Cys Ser Ile Ser Gln Val Asn Glu Lys Ile
```

```
                    450                 455                 460
Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His His Ser Ala Trp Ser His
        515                 520                 525

Pro Gln Phe Glu Lys
    530

<210> SEQ ID NO 26
<211> LENGTH: 509
<212> TYPE: PRT
<213> ORGANISM: Artificial Sequence
<220> FEATURE:
<223> OTHER INFORMATION: Peptide construct

<400> SEQUENCE: 26

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Gly Ser Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
```

```
            275                 280                 285
Thr Asn Thr Lys Glu Gly Ser Asn Ile Cys Leu Thr Arg Thr Asp Arg
            290                 295                 300
Gly Trp Tyr Cys Asp Asn Ala Gly Ser Val Ser Phe Phe Pro Gln Ala
305                 310                 315                 320
Glu Thr Cys Lys Val Gln Ser Asn Arg Val Phe Cys Asp Thr Met Asn
                325                 330                 335
Ser Leu Thr Leu Pro Ser Glu Val Asn Leu Cys Asn Val Asp Ile Phe
            340                 345                 350
Asn Pro Lys Tyr Asp Cys Lys Ile Met Thr Ser Lys Thr Asp Val Ser
            355                 360                 365
Ser Ser Val Ile Thr Ser Leu Gly Ala Ile Val Ser Cys Tyr Gly Lys
        370                 375                 380
Thr Lys Cys Thr Ala Ser Asn Lys Asn Arg Gly Ile Ile Lys Thr Phe
385                 390                 395                 400
Ser Asn Gly Cys Asp Tyr Val Ser Asn Lys Gly Val Asp Thr Val Ser
                405                 410                 415
Val Gly Asn Thr Leu Tyr Tyr Val Asn Lys Gln Glu Gly Lys Ser Leu
            420                 425                 430
Tyr Val Lys Gly Glu Pro Ile Ile Asn Phe Tyr Asp Pro Leu Val Phe
        435                 440                 445
Pro Ser Cys Glu Phe Cys Ala Ser Ile Ser Gln Val Asn Glu Lys Ile
        450                 455                 460
Asn Gln Ser Leu Ala Phe Ile Arg Lys Ser Asp Glu Leu Leu Ser Ala
465                 470                 475                 480
Ile Gly Gly Tyr Ile Pro Glu Ala Pro Arg Asp Gly Gln Ala Tyr Val
                485                 490                 495
Arg Lys Asp Gly Glu Trp Val Leu Leu Ser Thr Phe Leu
                500                 505

<210> SEQ ID NO 27
<211> LENGTH: 533
<212> TYPE: PRT
<213> ORGANISM: Artificial Sequence
<220> FEATURE:
<223> OTHER INFORMATION: Peptide construct

<400> SEQUENCE: 27

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
                20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gly Gly Gly Ser Gly Gly Gly Ser Gly Gly Gly Ser Gly Ser Ala
                100                 105                 110
Ile Ala Ser Gly Val Ala Val Cys Lys Val Leu His Leu Glu Gly Glu
            115                 120                 125
Val Asn Lys Ile Lys Ser Ala Leu Leu Ser Thr Asn Lys Ala Val Val
```

```
            130                 135                 140
Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
                180                 185                 190

Asn Arg Leu Leu Glu Ile Thr Arg Glu Phe Ser Val Asn Ala Gly Val
            195                 200                 205

Thr Thr Pro Val Ser Thr Tyr Met Leu Thr Asn Ser Glu Leu Leu Ser
        210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
                260                 265                 270

Val Ile Asp Thr Pro Cys Trp Lys Leu His Thr Ser Pro Leu Cys Thr
            275                 280                 285

Thr Asn Thr Lys Glu Gly Ser Asn Ile Cys Leu Thr Arg Thr Asp Arg
        290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
                340                 345                 350

Asn Pro Lys Tyr Asp Cys Lys Ile Met Thr Ser Lys Thr Asp Val Ser
            355                 360                 365

Ser Ser Val Ile Thr Ser Leu Gly Ala Ile Val Ser Cys Tyr Gly Lys
        370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
        435                 440                 445

Pro Ser Cys Glu Phe Cys Ala Ser Ile Ser Gln Val Asn Glu Lys Ile
        450                 455                 460

Asn Gln Ser Leu Ala Phe Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His Ser Ala Trp Ser His
        515                 520                 525

Pro Gln Phe Glu Lys
    530

<210> SEQ ID NO 28
```

<211> LENGTH: 509
<212> TYPE: PRT
<213> ORGANISM: Artificial Sequence
<220> FEATURE:
<223> OTHER INFORMATION: Peptide construct

<400> SEQUENCE: 28

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Ser Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380
```

```
Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
            405                 410                 415

Val Gly Asn Thr Leu Tyr Tyr Val Asn Lys Gln Glu Gly Lys Ser Leu
        420                 425                 430

Tyr Val Lys Gly Glu Pro Ile Ile Asn Phe Tyr Asp Pro Leu Val Phe
    435                 440                 445

Pro Ser Asp Glu Phe Asp Ala Ser Ile Ser Gln Val Asn Glu Lys Ile
450                 455                 460

Asn Gln Ser Leu Ala Phe Ile Arg Lys Ser Asp Glu Cys Cys Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu
            500                 505

<210> SEQ ID NO 29
<211> LENGTH: 533
<212> TYPE: PRT
<213> ORGANISM: Artificial Sequence
<220> FEATURE:
<223> OTHER INFORMATION: Peptide construct

<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Gly Ser Gly Gly Gly Ser Gly Ser Ala
            100                 105                 110

Ile Ala Ser Gly Val Ala Val Cys Lys Val Leu His Leu Glu Gly Glu
        115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240
```

-continued

Asn Asn Val Gln Ile Val Arg Gln Gln Ser Tyr Ser Ile Met Cys Ile
            245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
            275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
            355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
            450                 455                 460

Asn Gln Ser Leu Ala Phe Ile Arg Lys Ser Asp Glu Cys Cys Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His His Ser Ala Trp Ser His
            515                 520                 525

Pro Gln Phe Glu Lys
    530

<210> SEQ ID NO 30
<211> LENGTH: 509
<212> TYPE: PRT
<213> ORGANISM: Artificial Sequence
<220> FEATURE:
<223> OTHER INFORMATION: Peptide construct

<400> SEQUENCE: 30

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gly Gly Gly Ser Gly Gly Gly Ser Gly Gly Gly Ser Gly Ser Ala
            100                 105                 110

Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
            130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
                180                 185                 190

Asn Arg Leu Leu Glu Ile Thr Arg Glu Phe Ser Val Asn Ala Gly Val
            195                 200                 205

Thr Thr Pro Val Ser Thr Tyr Met Leu Thr Asn Ser Glu Leu Leu Ser
210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
            275                 280                 285

Thr Asn Thr Lys Glu Gly Ser Asn Ile Cys Leu Thr Arg Thr Asp Arg
290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
            355                 360                 365

Ser Ser Val Ile Thr Ser Leu Gly Ala Ile Val Ser Cys Tyr Gly Lys
            370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
            450                 455                 460

Asn Gln Ser Leu Ala Cys Ile Arg Lys Ser Asp Glu Leu Leu Ser Ala
465                 470                 475                 480
```

Ile Gly Gly Tyr Ile Pro Glu Ala Pro Arg Asp Gly Gln Ala Tyr Val
            485                 490                 495

Arg Lys Asp Gly Glu Trp Val Leu Leu Ser Thr Phe Leu
        500                 505

<210> SEQ ID NO 31
<211> LENGTH: 533
<212> TYPE: PRT
<213> ORGANISM: Artificial Sequence
<220> FEATURE:
<223> OTHER INFORMATION: Peptide construct

<400> SEQUENCE: 31

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Ser Gly Gly Ser Gly Ser Ala
            100                 105                 110

Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
    130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
    210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
    290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

```
Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
            355                 360                 365

Ser Ser Val Ile Thr Ser Leu Gly Ala Ile Val Ser Cys Tyr Gly Lys
            370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
            450                 455                 460

Asn Gln Ser Leu Ala Cys Ile Arg Lys Ser Asp Glu Leu Leu Ser Ala
465                 470                 475                 480

Ile Gly Gly Tyr Ile Pro Glu Ala Pro Arg Asp Gly Gln Ala Tyr Val
                485                 490                 495

Arg Lys Asp Gly Glu Trp Val Leu Leu Ser Thr Phe Leu Gly Gly Leu
            500                 505                 510

Val Pro Arg Gly Ser His His His His His His Ser Ala Trp Ser His
            515                 520                 525

Pro Gln Phe Glu Lys
            530

<210> SEQ ID NO 32
<211> LENGTH: 544
<212> TYPE: PRT
<213> ORGANISM: Artificial Sequence
<220> FEATURE:
<223> OTHER INFORMATION: Peptide construct

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Cys Lys Val Leu His Leu
145                 150                 155                 160
```

-continued

Glu Gly Glu Val Asn Lys Ile Lys Ser Ala Leu Leu Ser Thr Asn Lys
                165                 170                 175

Ala Val Val Cys Leu Ser Asn Gly Val Cys Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 33
<211> LENGTH: 568
<212> TYPE: PRT
<213> ORGANISM: Artificial Sequence
<220> FEATURE:
<223> OTHER INFORMATION: Peptide construct

<400> SEQUENCE: 33

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Cys Leu Ser Asn Gly Val Cys Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
```

```
                    405                 410                 415
Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 34
<211> LENGTH: 544
<212> TYPE: PRT
<213> ORGANISM: Artificial Sequence
<220> FEATURE:
<223> OTHER INFORMATION: Peptide construct

<400> SEQUENCE: 34

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
```

195                 200                 205
Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Cys Glu Phe Asp Cys Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 35
<211> LENGTH: 568
<212> TYPE: PRT
<213> ORGANISM: Artificial Sequence
<220> FEATURE:
<223> OTHER INFORMATION: Peptide construct

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe

```
            20                  25                  30
Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
             115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
             180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
             245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
             325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
             405                 410                 415

Tyr Gly Lys Thr Lys Cys Thr Ala Ser Asn Lys Asn Arg Gly Ile Ile
             420                 425                 430

Lys Thr Phe Ser Asn Gly Cys Asp Tyr Val Ser Asn Lys Gly Val Asp
        435                 440                 445
```

```
Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Cys Glu Phe Asp Cys Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 36
<211> LENGTH: 544
<212> TYPE: PRT
<213> ORGANISM: Artificial Sequence
<220> FEATURE:
<223> OTHER INFORMATION: Peptide construct

<400> SEQUENCE: 36

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65              70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
        100                 105                 110

Arg Phe Met Asn Tyr Thr Leu Asn Asn Ala Lys Lys Thr Asn Val Thr
    115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Phe Lys Val
        180                 185                 190

Leu Asp Leu Lys Asn Tyr Ile Asp Lys Gln Leu Leu Pro Ile Leu Asn
    195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
            275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Cys Glu Phe Cys Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

<210> SEQ ID NO 37
<211> LENGTH: 568
<212> TYPE: PRT
<213> ORGANISM: Artificial Sequence
<220> FEATURE:
<223> OTHER INFORMATION: Peptide construct

<400> SEQUENCE: 37

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480
```

-continued

```
Leu Val Phe Pro Ser Cys Glu Phe Cys Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 38
<211> LENGTH: 544
<212> TYPE: PRT
<213> ORGANISM: Artificial Sequence
<220> FEATURE:
<223> OTHER INFORMATION: Peptide construct

<400> SEQUENCE: 38

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Ser Tyr Ser Ile
            275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Cys
            500                 505                 510

Cys Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

<210> SEQ ID NO 39
<211> LENGTH: 568
<212> TYPE: PRT
<213> ORGANISM: Artificial Sequence
<220> FEATURE:
<223> OTHER INFORMATION: Peptide construct

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

```
Met Gln Ser Thr Pro Ala Thr Asn Arg Ala Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Cys
        500                 505                 510

Cys Ser Ala Ile Gly Gly Tyr Ile Pro Glu Ala Pro Arg Asp Gly Gln
```

```
            515                 520                 525
Ala Tyr Val Arg Lys Asp Gly Glu Trp Val Leu Leu Ser Thr Phe Leu
        530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 40
<211> LENGTH: 544
<212> TYPE: PRT
<213> ORGANISM: Artificial Sequence
<220> FEATURE:
<223> OTHER INFORMATION: Peptide construct

<400> SEQUENCE: 40

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
```

```
                305                 310                 315                 320
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Cys Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
            530                 535                 540

<210> SEQ ID NO 41
<211> LENGTH: 568
<212> TYPE: PRT
<213> ORGANISM: Artificial Sequence
<220> FEATURE:
<223> OTHER INFORMATION: Peptide construct

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
```

```
            130                 135                 140
Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Cys Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
        530                 535                 540

Gly Gly Leu Val Pro Arg Gly Ser His His His His His Ser Ala
545                 550                 555                 560
```

Trp Ser His Pro Gln Phe Glu Lys
565

<210> SEQ ID NO 42
<211> LENGTH: 512
<212> TYPE: PRT
<213> ORGANISM: Artificial Sequence
<220> FEATURE:
<223> OTHER INFORMATION: Peptide construct

<400> SEQUENCE: 42

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

```
Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Ser Ala Ile Gly Gly Tyr Ile Pro Glu Ala Pro Arg Asp Gly Gln
                485                 490                 495

Ala Tyr Val Arg Lys Asp Gly Glu Trp Val Leu Leu Ser Thr Phe Leu
            500                 505                 510
```

<210> SEQ ID NO 43
<211> LENGTH: 536
<212> TYPE: PRT
<213> ORGANISM: Artificial Sequence
<220> FEATURE:
<223> OTHER INFORMATION: Peptide construct

<400> SEQUENCE: 43

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205
```

```
Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Ser Ala Ile Gly Gly Tyr Ile Pro Glu Ala Pro Arg Asp Gly Gln
                485                 490                 495

Ala Tyr Val Arg Lys Asp Gly Glu Trp Val Leu Leu Ser Thr Phe Leu
            500                 505                 510

Gly Gly Leu Val Pro Arg Gly Ser His His His His His His Ser Ala
        515                 520                 525

Trp Ser His Pro Gln Phe Glu Lys
530                 535

<210> SEQ ID NO 44
<211> LENGTH: 477
<212> TYPE: PRT
<213> ORGANISM: Artificial Sequence
<220> FEATURE:
<223> OTHER INFORMATION: Peptide construct

<400> SEQUENCE: 44

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30
```

```
Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gly Gly Gly Ser Gly Gly Ser Gly Gly Ser Gly Ser Ala
                 100                 105                 110

Ile Ala Ser Gly Val Ala Val Cys Lys Val Leu His Leu Glu Gly Glu
                 115                 120                 125

Val Asn Lys Ile Lys Ser Ala Leu Leu Ser Thr Asn Lys Ala Val Val
                 130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                 165                 170                 175

Cys Ser Ile Ser Asn Ile Glu Thr Val Ile Glu Phe Gln Gln Lys Asn
                 180                 185                 190

Asn Arg Leu Leu Glu Ile Thr Arg Glu Phe Ser Val Asn Ala Gly Val
                 195                 200                 205

Thr Thr Pro Val Ser Thr Tyr Met Leu Thr Asn Ser Glu Leu Leu Ser
                 210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                 245                 250                 255

Ile Lys Glu Glu Val Leu Ala Tyr Val Val Gln Leu Pro Leu Tyr Gly
                 260                 265                 270

Val Ile Asp Thr Pro Cys Trp Lys Leu His Thr Ser Pro Leu Cys Thr
                 275                 280                 285

Thr Asn Thr Lys Glu Gly Ser Asn Ile Cys Leu Thr Arg Thr Asp Arg
                 290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                 325                 330                 335

Ser Leu Thr Leu Pro Ser Glu Val Asn Leu Cys Asn Val Asp Ile Phe
                 340                 345                 350

Asn Pro Lys Tyr Asp Cys Lys Ile Met Thr Ser Lys Thr Asp Val Ser
                 355                 360                 365

Ser Ser Val Ile Thr Ser Leu Gly Ala Ile Val Ser Cys Tyr Gly Lys
                 370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                 405                 410                 415

Val Gly Asn Thr Leu Tyr Tyr Val Asn Lys Gln Glu Gly Lys Ser Leu
                 420                 425                 430

Tyr Val Lys Gly Glu Pro Ile Ile Asn Phe Tyr Asp Pro Leu Ser Ala
                 435                 440                 445
```

Ile Gly Gly Tyr Ile Pro Glu Ala Pro Arg Asp Gly Gln Ala Tyr Val
450                 455                 460

Arg Lys Asp Gly Glu Trp Val Leu Leu Ser Thr Phe Leu
465                 470                 475

<210> SEQ ID NO 45
<211> LENGTH: 501
<212> TYPE: PRT
<213> ORGANISM: Artificial Sequence
<220> FEATURE:
<223> OTHER INFORMATION: Peptide construct

<400> SEQUENCE: 45

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gly Gly Ser Gly Gly Ser Gly Gly Ser Gly Ser Ala
                100                 105                 110

Ile Ala Ser Gly Val Ala Val Cys Lys Val Leu His Leu Glu Gly Glu
            115                 120                 125

Val Asn Lys Ile Lys Ser Ala Leu Leu Ser Thr Asn Lys Ala Val Val
        130                 135                 140

Ser Leu Ser Asn Gly Val Ser Val Leu Thr Phe Lys Val Leu Asp Leu
145                 150                 155                 160

Lys Asn Tyr Ile Asp Lys Gln Leu Leu Pro Ile Leu Asn Lys Gln Ser
                165                 170                 175

Cys Ser Ile Ser Asn Ile Glu Thr Val Ile Glu Phe Gln Gln Lys Asn
            180                 185                 190

Asn Arg Leu Leu Glu Ile Thr Arg Glu Phe Ser Val Asn Ala Gly Val
        195                 200                 205

Thr Thr Pro Val Ser Thr Tyr Met Leu Thr Asn Ser Glu Leu Leu Ser
210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Cys Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
        275                 280                 285

Thr Asn Thr Lys Glu Gly Ser Asn Ile Cys Leu Thr Arg Thr Asp Arg
290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
        355                 360                 365

Ser Ser Val Ile Thr Ser Leu Gly Ala Ile Val Ser Cys Tyr Gly Lys
    370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
            405                 410                 415

Val Gly Asn Thr Leu Tyr Tyr Val Asn Lys Gln Glu Gly Lys Ser Leu
        420                 425                 430

Tyr Val Lys Gly Glu Pro Ile Ile Asn Phe Tyr Asp Pro Leu Ser Ala
    435                 440                 445

Ile Gly Gly Tyr Ile Pro Glu Ala Pro Arg Asp Gly Gln Ala Tyr Val
    450                 455                 460

Arg Lys Asp Gly Glu Trp Val Leu Leu Ser Thr Phe Leu Gly Gly Leu
465                 470                 475                 480

Val Pro Arg Gly Ser His His His His His His Ser Ala Trp Ser His
            485                 490                 495

Pro Gln Phe Glu Lys
            500

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
ctcaatttcc tcacttctcc agtgt                                         25

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
cttgattcct cggtgtacct ctgt                                          24

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
tcccattatg cctaggccag cagca                                         25

<210> SEQ ID NO 49
<211> LENGTH: 4
<212> TYPE: PRT
<213> ORGANISM: Artificial Sequence
<220> FEATURE:
<223> OTHER INFORMATION: Amino acid linker

<400> SEQUENCE: 49

Gly Gly Gly Ser
1

STABILIZED RSV F PROTEINS AND USES THEREOF

CROSS REFERENCE TO RELATED APPLICATIONS

This application is a U.S. National Phase application under 371 National Stage of International Application No. PCT/US2019/014873, filed on Jan. 24, 2019, which claims priority to U.S. provisional Application No. 62/623,184, filed on Jan. 29, 2018.

FILED OF THE INVENTION

The present disclosure relates to stable RSV F proteins and immunogenic compositions containing the same, as well as methods of using the immunogenic compositions and compositions comprising the RSV F proteins.

REFERENCE TO SEQUENCE LISTING SUBMITTED ELECTRONICALLY

The sequence listing of the present application is submitted electronically via EFS-Web as an ASCII formatted sequence listing with a file name "24566USPCT-SEQLIST-17DECSEP2020.txt", creation date of Dec. 17, 2020, and a size of 167 Kb. This sequence listing submitted via EFS-Web is part of the specification and is herein incorporated by reference in its entirety.

BACKGROUND OF INVENTION

Respiratory Syncytial Virus (RSV) is a member of the pneumovirus family. RSV infection is the leading cause of lower respiratory tract infection in both young children and older adults (>65 years). Currently, there is no licensed vaccine available, and therapeutic options are limited.

The envelope of RSV contains three surface glycoproteins: F, G, and SH. The G and F proteins are protective antigens and targets of neutralizing antibodies. The F protein, however, is more conserved across RSV strains and types (A and B). RSV F is a type I viral fusion protein which structurally rearranges from a metastable prefusion form to a highly stable postfusion form. Although targets for neutralizing monoclonal antibodies exist on the postfusion conformation of F protein, the neutralizing Ab response primarily targets the F protein prefusion conformation in people naturally infected with RSV (Magro M et al., *Proc Natl Acad Sci USA;* 109(8):3089-94, 2012; Ngwuta JO et al., *Sci Transl Med* 2015; 7(309):309ra162). Therefore, engineered RSV F protein stabilized in its prefusion conformation has been an attractive strategy for developing RSV F vaccine antigens. For example, a recombinant RSV F trimer including the "DS-Cavl" substitutions (155C, 290C, 190F, and 207L) was previously shown to elicit neutralizing immune response in animal models that is greater than the response observed for post-fusion F based RSV immunogens (McLellan et al., *Science,* 342: 592-598, 2013). Described herein are new RSV antigens which are even more stable in the prefusion form of interest.

SUMMARY OF INVENTION

The present disclosure provides a recombinant respiratory syncytial virus (RSV) F trimer, comprising: three recombinant RSV F peptides each comprising a deletion of RSV F wild type amino acids at positions 98-146 and a linker of eight to fourteen amino acids between RSV F wild type amino acid positions 97 and 147, wherein the recombinant F peptides comprise the following modifications to stabilize the recombinant RSV F trimer in a prefusion conformation: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (0 a deletion of RSV F wild type amino acids 482-513. In one embodiment, each RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, each RSV F peptide comprises a deletion of RSV F wild type amino acids 514-574.

In one embodiment of the recombinant RSV F trimer, each of the recombinant F peptides further comprise a foldon sequence at the C-terminus of each peptide. In a further embodiment, the sequence of the foldon domain begins at the C-terminus of the peptide and replaces the RSV F wild type transmembrane domain and cytoplasmic domain (for example, the foldon domain replaces RSV F wild type amino acids 525-574). In a further embodiment, the sequence of the foldon domain begins after amino acid position 513 of wild type RSV F (i.e., the foldon sequence replaces amino acids 514-574 of wild type RSV-F). In another embodiment, when the RSV F peptides contain an additional deletion of amino acids 482-513 of wild type RSV F, the sequence of the foldon domain begins after amino acid position 481 of wild type RSV F (see, e.g., SEQ ID NO: 44). In some embodiments, the foldon sequence comprises SEQ ID NO: 8.

In one embodiment of the RSV F trimer, the recombinant F peptides each comprise the 190F and 207L amino acid substitutions, the 155C and 290C amino acid substitutions, the 486C and 490C amino acid substitutions, and the deletion of amino acids 514-574 of wild type RSV F. In one embodiment, each recombinant F peptide further comprises a non-native intra peptide disulfide bond between cysteines introduced by the 155C and 290C amino acid substitutions. In another embodiment, the RSV F trimer comprises one or more non-native inter peptide disulfide bond between cysteines introduced by the 486C and 490C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the RSV F trimer, the recombinant F peptides each comprise the 190F and 207L amino acid substitutions, the 155C and 290C amino acid substitutions, the 180C and 186C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions and/or a non-native intra peptide disulfide bond between cysteines introduced by the 190C and 186C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions, the 486C and 489C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions. In another embodiment, the RSV F trimer comprises a non-native inter-peptide disulfide bond between cysteines introduced by the 486C and 489C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the RSV trimer, the recombinant F peptides each comprise the 190F and 207L amino acid substitutions, the 155C and 290C amino acid substitutions, the 512C and 513C amino acid substitutions, and the deletion of amino acids 514-574 of wild type RSV F. In one embodiment, each recombinant RSV F peptide further comprises a non-native intra peptide disulfide bond between cysteines introduced by the 155C and 290C amino acid substitutions. In another embodiment, the RSV F trimer comprises a non-native inter-peptide disulfide bond between cysteines introduced by 512C and 513C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions, the 505C amino acid substitution, and the deletion of amino acids 514-574 of wild type RSV F. In another embodiment, each recombinant RSV F peptide further comprises a non-native intra peptide disulfide bond between cysteines introduced by the 155C and 290C amino acid substitutions. In a further embodiment, the C-terminus of the recombinant RSV F peptides each comprises a sequence of a foldon domain. In another embodiment, the sequence of the foldon domain comprises SEQ ID NO: 8.

In one embodiment of the recombinant RSV F trimer, the recombinant F peptides each comprise the 190F and 207L amino acid substitutions, the 155C and 290C amino acid substitutions and the deletion of amino acids 482-513 of wild type RSV F, as well as the deletion of amino acids 514-574 of wild type RSV F. In one embodiment, each recombinant RSV F peptide further comprises a non-native intra peptide disulfide bond between cysteines introduced by the 155C and 290C amino acid substitutions. In a further embodiment, the C-terminus of the recombinant RSV F peptides each comprises a sequence of a foldon domain.

In another embodiment, the sequence of the foldon domain comprises SEQ ID NO: 8.

In one embodiment, the linker is eight (8), ten (10), twelve (12), or fourteen (14) amino acids in length. In one embodiment, the linker comprises the amino acid sequence set forth in SEQ ID NO: 46. In another embodiment, the linker has the amino acid sequence as set forth in any of SEQ ID NOS: 1, 2, 3, or 4.

In one embodiment, the recombinant F peptides of the RSV F trimer each comprise, consist essentially of, or consist of, the mature amino acid sequence as set forth in SEQ ID NO: 22. In one embodiment, the recombinant F peptides of the RSV F trimer each comprise, consist essentially of, or consist of, the mature amino acid sequence as set forth in SEQ ID NO: 24. In one embodiment, the recombinant F peptides of the RSV F trimer each comprise, consist essentially of, or consist of, the mature amino acid sequence as set forth in SEQ ID NO 26. In one embodiment, the recombinant F peptides of the RSV F trimer each comprise, consist essentially of, or consist of, the mature amino acid sequence as set forth in SEQ ID NO 28. In one embodiment, the recombinant F peptides of the RSV F trimer each comprise, consist essentially of, or consist of, the mature amino acid sequence as set forth in SEQ ID NO: 30. In one embodiment, the recombinant F peptides of the RSV F trimer each comprise, consist essentially of, or consist of, the mature amino acid sequence as set forth in SEQ ID NO: 44.

The present disclosure also provides an RSV immunogenic composition comprising a recombinant respiratory syncytial virus (RSV) F trimer, comprising: three recombinant RSV F peptides each comprising a deletion of RSV F wild type amino acids at positions 98-146 and a linker of eight to fourteen amino acids between RSV F wild type amino acid positions 97 and 147, wherein the recombinant F peptides comprise the following modifications to stabilize the recombinant RSV F trimer in a prefusion conformation: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (f) a deletion of RSV F wild type amino acids 482-513. In one embodiment, each RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, each RSV F peptide comprises a deletion of RSV F wild type amino acids 514-574.

In one embodiment of the immunogenic composition, each of the recombinant F peptides further comprise a foldon sequence at the C-terminus of each peptide. In a further embodiment, the sequence of the foldon domain begins after amino acid position 513 of wild type RSV F (i.e., the foldon sequence replaces amino acids 514-574 of wild type RSV-F). In another embodiment, when the RSV F peptides contain an additional deletion of amino acids 482-513 of wild type RSV F, the sequence of the foldon domain begins after amino acid position 481 of wild type RSV F (see, e.g., SEQ ID NO: 44). In some embodiments, the foldon sequence comprises SEQ ID NO: 8.

In one embodiment of the immunogenic composition, the RSV F trimer is any of the RSV trimers described herein. In another embodiment of the immunogenic composition, the recombinant F peptides of the RSV F trimer each comprise, consist essentially of, or consist of, the mature amino acid sequence as set forth in any of SEQ ID NO: 22, 24, 26, 28, 30 and 44.

The present disclosure also provides a RSV peptide which comprises a deletion of RSV F wild type amino acids at positions 98-146 and a linker of eight to fourteen amino acids between RSV F wild type positions 97 and 147, and additional modifications to stabilize a recombinant RSV F trimer containing three of such recombinant RSV peptides in the prefusion conformation. Such additional modifications in the single chain RSV peptide comprise: (i) 190F and 207L amino acid substitutions, (ii) 155C and 290C amino acid substitutions, and one (or more) of (a) 486C and 490C amino acid substitutions; (b) 180C and 186C amino acid substitutions; (c) 486C and 489C amino acid substitutions; (d) 512C and 513C amino acid substitutions; (e) an 505C amino acid substitution; and (f) a deletion of RSV F wild type amino acids 482-513. In one embodiment, the RSV F peptide further comprises at the C-terminus a deletion of the RSV F wild type transmembrane domain and cystoplasmic domain (for example, comprises at the c-terminus a deletion of RSV F wild type amino acids 525-574). In a further embodiment, the RSV F peptide comprises a deletion of RSV F wild type amino acids 514-574.

In one embodiment, the RSV F peptide further comprises a foldon sequence at the C-terminus. In a further embodiment, the sequence of the foldon domain begins after amino acid position 513 of wild type RSV F (i.e., the foldon sequence replaces amino acids 514-574 of wild type RSV-F). In another embodiment, when the RSV F peptide contains an additional deletion of amino acids 482-513 of wild type RSV F, the sequence of the foldon domain begins after amino acid position 482 of wild type RSV F (see, e.g., SEQ ID NO: 44). In some embodiments, the foldon sequence comprises SEQ ID NO: 8.

In one embodiment, the RSV F peptide comprises the 190F and 207L amino acid substitutions, the 155C and 290C amino acid substitutions, the 486C and 490C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8. In one embodiment, the RSV F peptide comprises the 190F and 207L amino acid substitutions, the 155C and 290C amino acid substitutions, the 180C and 186C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions and/or a non-native intra peptide disulfide bond between cysteines introduced by the 190C and 186C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 486C and 489C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 512C and 513C amino acid substitutions, and the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions, the 505C amino acid substitution, and the deletion of amino acids 514-574 of wild type RSV F. In another embodiment, the RSV F peptide further comprises a non-native intra peptide disulfide bond between cysteines introduced by the 155C and 290C amino acid substitutions. In a further embodiment, the C-terminus of the RSV F peptide comprises a sequence of a foldon domain. In another embodiment, the sequence of the foldon domain comprises SEQ ID NO: 8.

In one embodiment, the RSV F peptide comprises the 190F and 207L amino acid substitutions, the 155C and 290C amino acid substitutions and the deletion of amino acids 482-513 of wild type RSV F, as well as the deletion of amino acids 514-574 of wild type RSV F. In one embodiment, the RSV F peptide further comprises a non-native intra peptide disulfide bond between cysteines introduced by the 155C and 290C amino acid substitutions. In a further embodiment, the C-terminus of the RSV F peptides each comprises a sequence of a foldon domain. In another embodiment, the sequence of the foldon domain comprises SEQ ID NO: 8.

In one embodiment, the linker is eight (8), ten (10), twelve (12), or fourteen (14) amino acids in length. In one embodiment, the linker comprises the amino acid sequence set forth in SEQ ID NO: 46. In another embodiment, the linker has the amino acid sequence as set forth in any of SEQ ID NOS: 1, 2, 3, or 4.

In one embodiment, the RSV F peptide comprises, consists essentially of, or consists of, the mature amino acid sequence as set forth in SEQ ID NO: 22. In one embodiment, the RSV F peptide comprises, consists essentially of, or consists of, the mature amino acid sequence as set forth in SEQ ID NO: 24. In one embodiment, the RSV F peptides comprises, consists essentially of, or consists of, the mature amino acid sequence as set forth in SEQ ID NO 26. In one embodiment, the RSV F peptide comprises, consists essentially of, or consists of, the mature amino acid sequence as set forth in SEQ ID NO 28. In one embodiment, the RSV F peptide comprises, consists essentially of, or consists of, the mature amino acid sequence as set forth in SEQ ID NO: 30. In one embodiment, the RSV F peptide comprises, consists essentially of, or consists of, the mature amino acid sequence as set forth in SEQ ID NO: 44.

In one embodiment, the RSV peptide, when produced recombinantly, forms an RSV F trimer, as described herein.

The present disclosure also provides for an isolated nucleic acid molecule encoding a single chain RSV peptide as described herein. In one embodiment, the isolated nucleic acid molecule is a DNA molecule. The present disclosure further provides for a vector comprising said nucleic acid molecule.

The present disclosure also provides a method of making a recombinant respiratory syncytial virus (RSV) F trimer as described herein, said method comprising (i) expressing the nucleic acid molecule, or the vector, each described above, and (ii) purifying a recombinant RSV F trimer produced therefrom.

The present disclosure also provides antibody molecules, including full length antibodies and antibody derivatives, directed against the RSV F trimer described herein, or against the RSV F peptides described herein.

In some embodiments, the immunogenic composition is formulated with an adjuvant. In one embodiment, the adjuvant is an aluminum adjuvant. In some embodiments, the aluminum adjuvant is MAA or MAPA.

In some embodiments, the recombinant RSV F trimer or RSV F peptides, each described herein, is formulated with a lipid nanoparticle (LNP) comprising a cationic lipid, a PEG-modified lipid, a sterol, and a non-cationic lipid.

Some embodiments of the present disclosure provide methods of an RSV F specific immune response in a subject, comprising administering to the subject any of the immunogenic compositions described herein, or the recombinant RSV F trimers as described herein, in an amount effective to produce an RSV F specific immune response. In some embodiments, the antigen-specific immune response comprises a T cell response or a B cell response.

In some embodiments, the method comprises administering to a subject a single dose (no booster dose) of an immunogenic composition, or an RSV F trimer, as described herein. In another embodiment, the method further comprises administering to the subject a second (booster) dose of an immunogenic composition, or an RSV F trimer, as described herein. In another embodiment, the method further comprises administering at least one booster dose of the RSV F trimer or RSV immunogenic composition. Additional doses may be administered.

In some embodiments, the RSV immunogenic composition, or RSV F trimer, is administered to a subject by intradermal injection, intramuscular injection, or by intranasal administration. In some embodiments, an RSV vaccine is administered to a subject by intramuscular injection. In some embodiments, the RSV F trimer, or immunogenic composition, immunizes the subject against RSV for up to 1 or 2 years. In some embodiments, the RSV F trimer, or immunogenic composition, immunizes the subject against RSV for more than 2 years, more than 3 years, more than 4 years, or for 5-10 years. In one embodiment, the immunogenic composition is administered as a vaccine yearly.

In some embodiments, the subject is about 5 years old or younger. For example, the subject may be between the ages of about 1 year and about 5 years (e.g., about 1, 2, 3, 4 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a vaccine may be administered later in life, for example, at the age of about 6 months to about 5 years, or older.

In some embodiments, the subject is a young adult between the ages of about 20 years and about 50 years (e.g., about 20, 25, 30, 35, 40, 45 or 50 years old). In some embodiments, the subject is an elderly subject about 50-60 years old, 60 years old, about 70 years old, or older, 80 years or older, 90 years or older (e.g., about 60, 65, 70, 75, 80, 85 or 90 years old). In some embodiments, the subject is immunocompromised (e.g., has an immune disorder or autoimmune disorder).

In some embodiments, the subject is pregnant when administered the RSV immunogenic composition. In some embodiments, the subject has a chronic pulmonary disease, such as chronic obstructive pulmonary disease (COPD) or asthma.

In some embodiments, the subject has been exposed to RSV, is infective with (has) RSV, or is at risk of infection by RSV.

The details of various embodiments of the disclosure are set forth in the description below. Other features, objects, and advantages of the disclosure will be apparent from the description and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIGS. 2A, 2B, and 2C, respectively) or those stored at 4° C. for 7 days (FIGS. 2D, 2E, and 2F, respectively) to D25 and Synagis® (palivizumab).

FIG. 16A is high dose immunization. FIG. 16B is low dose immunization. FIG. 16C shows the area under the curve.

FIG. 17A is high dose immunization. FIG. 17B is low dose immunization. FIG. 17C shows the area under the curve.

DETAILED DESCRIPTION

Figure 1A:
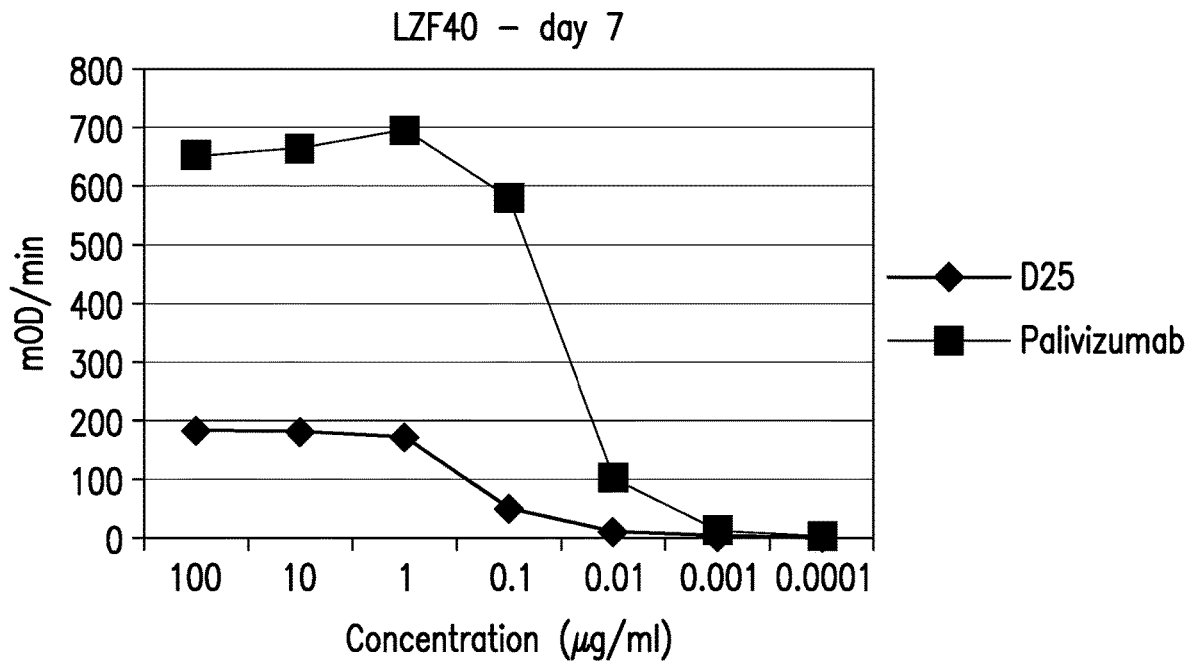
FIGS. 1A and 1B show binding of freshly harvested day 7 post-transfection cell culture supernatants (supe) of LZF40 (DS-Cav1 with an 8 a.a. linker) (FIG. 1A) or those stored at 4° C. for 8 days (FIG. 1B) to D25 and Synagis® (palivizumab) monoclonal antibodies.

RSV F protein is a type I fusion glycoprotein that is well conserved between clinical isolates, including between the RSV-A and RSV-B antigenic subgroups. The F protein transitions between prefusion and more stable postfusion states, thereby facilitating entry into target cells. RSV F glycoprotein is initially synthesized as an $F_0$ precursor protein. RSV $F_0$ folds into a trimer, which is activated by furin cleavage into the mature prefusion protein comprising F1 and F2 subunits (Bolt, et al., *Virus Res.*, 68:25, 2000). RSV F protein stabilized in the prefusion conformation produces a greater neutralizing immune response in animal models than that observed with RSV F protein stabilized in the post fusion conformation (McLellan et al., *Science*, 342: 592-598, 2013). As such, stabilized prefusion RSV F proteins are good candidates for inclusion in an RSV vaccine. Soluble RSV ectodomains stabilized in the prefusion conformation have previously been generated, including the "DS-Cav1" substitutions. See, WO 2014/160463A1 and WO 2017/172890A1, the contents of each of which are hereby incorporated by reference.

It has been previously shown that the prefusion stabilized RSV F construct, DS-Cav1, undergoes conformational changes and forms intermediate structures upon long-term storage at 4° C. (Flynn JA et al., *PLoS ONE* 2016; 11(10): e0164789). Long term stability at 4° C. or higher is a desirable attribute for a RSV F subunit vaccine antigen. Described herein are additional structure-based modifications to further improve the stability of the RSV F trimer in the prefusion conformation. Such constructs have increased stability at 4° C. as compared to DS-Cav1 while retaining immunogenicity.

"RSV Fusion Protein" and "RSV F protein", each as used herein refers to an RSV envelope glycoprotein that facilitates fusion of viral and cellular membranes. In nature, the RSV F protein is synthesized into a single polypeptide precursor designated $F_0$, which includes a signal peptide that directs localization to the endoplasmic reticulum, where the signal peptide is cleaved. The remaining $F_0$ residues oligomerize to form a trimer and are proteolytically processed by a protease at two conserved furin cleavage sequences to generate two disulfide linked fragments, $F_1$ and $F_2$. In nature, three $F_2$-$F_1$ peptides oligomerize into a trimer to form the mature F protein, which adopts a prefusion conformation that is metastable and can undergo a conformation change to a postfusion conformation.

"RSV F transmembrane domain" corresponds to the transmembrane domain of wild type RSV F (i.e., amino acids 525-550 of SEQ ID NO: 10).

"RSV F cytoplasmic domain" or "RSV F cytoplasmic tail" corresponds to the cytoplasmic tail domain of wild type RSV F (i.e., amino acid 551-574 of SEQ ID NO: 10).

"D25" or "D25 antibody" as used herein describes a neutralizing antibody that specifically binds to prefusion RSV F peptides. This antibody is described in U.S. Patent Application Publication No. US 2010/0239593, the entire content of which is hereby incorporated by reference.

"Single chain RSV mutants" refer to an RSV F protein that has been modified so that it does not include the furin cleavage sites such that when a single chain RSV mutant is produced in cells, the $F_0$ peptide is not cleaved into separate $F_1$ and $F_2$ chains. A non-limiting example of a single chain RSV mutant includes position 97 of the $F_2$ polypeptide linked to position 97 to position 147 of the $F_1$ peptide by a flexible linker to generate the single chain RSV mutant.

"DS-Cav1"; "DS-Cav1 substitutions", each as used herein, refer to genetic modifications to the RSV F protein, which contains the "DS" substitutions 155C and 290C so as to introduce a non-native disulfide bond between cysteines introduced by the substitutions (such as S155C and S290C substitutions) and the "Cav1" substitutions, which include 190F and 207L cavity filling amino acid substitutions (such as S190F and V207L). DS-Cav1 is described in WO 2014/160463, the entire contents of which are hereby incorporated by reference.

"Foldon domain" or "foldon", each as used herein, refers to a T4 fibritin trimerization domain that comprises an amino acid sequence that naturally forms a trimeric structure. In some examples, the sequence of the RSV F protein is modified to contain a foldon domain. In other examples, the single chain RSV mutants contain a foldon domain. An example of a foldon trimerization domain comprises the amino acid sequence as set forth in SEQ ID NO: 8.

As used herein, a "signal peptide" or "signal sequence" are short amino acid sequences that direct newly synthesized secretory or membrane proteins to and through membranes, and thus universally control the entry of most proteins both in eukaryotes and prokaryotes to the secretory pathway. Endoplasmic reticulum processing produces mature proteins, wherein the signal peptide is cleaved from the precursor proteins. As referred to herein, the "mature amino acid sequence" does not contain the signal peptide. The mature amino acid sequence of the single chain RSV mutants does not contain a signal peptide. In addition, the RSV trimer which is comprised of three mature single chain RSV mutants does not contain the signal peptide sequence.

As used herein, the term "substitution", "amino acid substitution," "or" "substitutional variant" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule. For example, as used herein, reference to a "155C" substitution in an RSV F protein or single chain RSV F mutant refers to the single chain RSV F protein having a cysteine residue at position 155, which cysteine residue has been substituted for the corresponding native residue at position 155 in the RSV F protein. By way of reference, SEQ ID NO: 10 is a reference sequence with regard to the location of the substitution. For example, a "S155C" substitution is a substitution of the S at position 155 of SEQ ID NO: 10 with ata C.

"Isolated" polypeptides or polynucleotides are at least partially free of other biological molecules from the cells or cell cultures in which they are produced. Such biological molecules include other nucleic acids, proteins, lipids, carbohydrates, or other material such as cellular debris and growth medium. It may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the polypeptides or polynucleotides.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

"Analogs" is meant to include polypeptide variants that differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal end). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue. As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide-based or polynucleotide-based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, 96%, 97%, 98%, 99% or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." I Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins."*J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules) and/or between polypeptide molecules. Polymeric molecules (e.g. nucleic acid molecules (e.g. DNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98% or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, N.J., 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12, 387 (1984)), BLASTP, BLASTN, and FASTA Altschul, S. F. et al., *J. Molec. Biol.,* 215, 403 (1990)).

Lipid Nanoparticles

As used herein, "lipid nanoparticle" or "LNP" refers to any lipid composition that can be used to deliver a product, including, but not limited to, liposomes or vesicles, wherein an aqueous volume is encapsulated by amphipathic lipid bilayers (e.g., single; unilamellar or multiple; multilamellar), or, in other embodiments, wherein the lipids coat an interior comprising a prophylactic product, or lipid aggregates or micelles, wherein the lipid encapsulated therapeutic product is contained within a relatively disordered lipid mixture. Except where noted, the lipid nanoparticle does not need to have the antigenic polypeptide incorporated therein and may be used to deliver a product when in the same formulation.

As used herein, "polyamine" means compounds having two or more amino groups. Examples include putrescine, cadaverine, spermidine, and spermine.

Unless otherwise specified, mole % refers to a mole percent of total lipids. Generally, the LNPs of the compositions of the invention are composed of one or more cationic lipids (including ionizable cationic lipids) and one or more poly(ethyleneglycol)-lipids (PEG-lipids). In certain embodiments, the LNPs further comprise one or more non-cationic lipids. The one or more non-cationic lipids can include a phospholipid, phospholipid derivative, a sterol, a fatty acid, or a combination thereof.

Cationic lipids and ionizable cationic lipids suitable for the LNPs are described herein. Ionizable cationic lipids are characterized by the weak basicity of their lipid head groups, which affects the surface charge of the lipid in a pH-dependent manner, rendering them positively charged at acidic pH but close to charge-neutral at physiologic pH. Cationic lipids are characterized by monovalent or multivalent cationic charge on their headgroups, which renders them positively charged at neutral pH. In certain embodiments, the cationic and ionizable lipid is capable of complexing with hydrophilic bioactive molecules to produce a hydrophobic complex that partitions into the organic phase of a two-phase aqueous/organic system. It is contemplated that both monovalent and polyvalent cationic lipids may be utilized to form hydrophobic complexes with bioactive molecules.

In some embodiments, the cationic and ionizable cationic lipids for use in forming the LNPs include, but are not limited to, N,N-dioleyl-N,N-dimethylammonium chloride ("DODAC"); N-(2,3dioleyloxy)propyl)-N,N,Ntrimethylammonium chloride ("DOTMA");

N,NdistearylN,N-dimethylammonium bromide ("DDAB"); N-(2,3dioleoyloxy)propyl)-N,N,N-trimethyl-amntonium chloride ("DODAP"); 1,2 bis (oleoyloxy)-3-(trimethylammonio) propane (DOTAP); 3-(N-(N,N-dimethylaminoethane)-carbam-oyl)cholesterol ("DC-Chol"); diheptadecylamidoglycylspermidine ("DHGS") and N-(1,2-dimyristyloxyprop-3-yl)-N,N-dimethyl-N-hydoxyethyl ammonium bromide ("DMRIE"). Additionally, a number of commercial preparations of cationic lipids, as well as other components, are available which can be used in the present invention. These include, for example, LIPOFECTIN® (commercially available cationic lipid nanoparticles comprising DOTMA and 1,2dioleoyl-sn-3-phosphoethanolamine ("DOPE"), from GIBCOBRL, Grand Island, N.Y., USA); and LIPOFECTAMINE® (commercially available cationic lipid nanoparticles comprising N-(1-(2,3dioleyloxy)propyl)N-(2-(sperminecarboxamido)ethyl)-N,N-dimethylammonium trifluoroacetate ("DOSPA") and ("DOPE"), from (GIBCOBRL). The following lipids are cationic and have a positive charge at below physiological pH: DODAP, DODMA, DMDMA, 1,2-DiLinoleyloxy-N,N-dimethylaminopropane (DLinDMA), 4-(2,2-diocta-9,12-dienyl-[1,3]dioxolan-4-ylmethyl)-dimethylamine, DLinKDMA (WO 2009/132131 A1), DLin-K-C2-DMA (WO2010/042877), DLin-M-C3-DMA (WO2010/146740 and/or WO2010/105209), DLin-MC3-DMA (heptatriaconta-6,9,28,31-tetraen-19-yl 4-(dimethylamino)butanoate; Jayaraman et al., 2012, Angew. Chem. Int. Ed. Engl. 51:8529-8533), 2-{4-[(3β)-cholest-5-en-3-yloxy]butoxyl}-N,N-dimethyl-3-[(9Z,12Z)-octadeca-9,12-dienlyloxyl]propan-1-amine) (CLinDMA), and the like. Other cationic lipids suitable for use in the invention include, e.g., the cationic lipids described in U.S. Pat. Nos. 5,208,036, 5,264,618, 5,279,833 and 5,283,185, and U.S. Patent Application Publication Nos. 2008/0085870 and 2008/0057080. Other cationic lipids suitable for use in the invention include, e.g., Lipids E0001-E0118 or E0119-E0180 as disclosed in Table 6 (pages 112-139) of International Patent Application Publication No. WO2011/076807 (which also discloses methods of making, and methods of using these cationic lipids).

In some embodiments, the cationic lipid comprises any one of DLinDMA; DlinKC2DMA; DLin-MC3-DMA; CLinDMA; S-Octyl CLinDMA;

(2 S)-1-{7-[(3 β)-cholest-5-en-3-yloxy]heptyloxy}-3-[(4 Z)-dec-4-en-1-yloxy]-N, N-dimethylpropan-2-amine;

(2 R)-1-{4-[(3β)-cholest-5-en-3-yloxy]butoxy}-3-[(4 Z)-dec-4-en-1-yloxy]-N, N-dimethylpropan-2-amine;

1-[(2 R)-1-{7-[(3 β)-cholest-5-en-3-yloxy]butoxy}-3-(octyloxy)propan-2-yl]guanidine;

1-[(2 R)-1-{7-[(3 β)-cholest-5-en-3-yloxy]heptyloxy}-N,N-dimethyl-3-[(9 Z, 12 Z)-octadeca-9,12-dien-1-yl]oxy]propan-2-amine;
1-[(2 R)-1-{4-[(3 β)-cholest-5-en-3-yl]oxy]butoxy}-N,N-dimethyl-3-[(9 Z, 12 Z)-octadeca-9,12-dien-1-yloxy]propan-2-amine;
(2S)-1-({6-[(3 β)-cholest-5-en-3-yloxy]hexyl}oxy)-N,N-dimethyl-3-[(9 Z)-octadec-9-en-1-yloxy]propan-2-amine;
(3β)-3-[6-{[(2S)-3-[(9Z)-octadec-9-en-1-yloxyl]-2-(pyrrolidin-1-yl)propyl]oxy}hexyl)oxy]cholest-5-ene;
(2R)-1-({4-[(3β)-cholest-5-en-3-yloxy]butoxy}-3-(octyloxy)propan-2-amine;
(2R)-1-({8-[(3β)-cholest-5-en-3-yloxy]octyl}oxy)-N,N-dimethyl-3-(pentyloxy)propan-2-amine;
(2R)-1-({8-[(3β)-cholest-5-en-3-yloxyl]octyl}oxy)-3-(heptyloxy)-N,N-dimethylpropan-2-amine;
(2R)-1-({8-[(3β)-cholest-5-en-3-yloxy]octyl}oxy)-N,N-dimethyl-3-[(2Z)-pent-2-en-1-yloxy]propan-2-amine;
(2S)-1-butoxy-3-({8-[(3β)-cholest-5-en-3-yloxy]octyl}oxy)-N,N-dimethylpropan-2-amine;
(2S-1-({8-[(3β)-cholest-5-en-3-yloxy]octyl}oxy)-[2,2,3,3,4,4,5,5,6,6,7,7,8,8,9,9-hexadecafluorononyl)oxy]-N,N-dimethylpropan-2-amine;
2-amino-2-{[(9Z,12Z)-octadeca-9,12-dien-1-yloxy]methyl}propane-1,3-diol;
2-amino-3-((9-(((3S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)nonyl)oxy)-2-((((9Z,12Z)-octadeca-9,12-dien-1-yl)oxy)methyl)propan-1-ol;
2-amino-3-((6-(((3 S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)hexyl)oxy)-2-((((Z)-octadec-9-en-1-yl)oxy)methyl)propan-1-ol;
(20Z,23Z)-N,N-dimethylnonacosa-20,23-dien-10-amine;
(17Z,20Z)-N,N-dimethylhexacosa-17,20-dien-9-amine;
(16Z,19Z)-N,N-dimethylpentacosa-16,19-dien-8-amine;
(13Z,16Z)-N,N-dimethyldocosa-13,16-dien-5-amine;
(12Z,15Z)-N,N-dimethylhenicosa-12,15-dien-4-amine;
(14Z,17Z)-N,N-dimethyltricosa-14,17-dien-6-amine;
(15Z,18Z)-N,N-dimethyltetracosa-15,18-dien-7-amine;
(18Z,21Z)-N,N-dimethylheptacosa-18,21-dien-10-amine;
(15Z,18Z)-N,N-dimethyltetracosa-15,18-dien-5-amine;
(14Z,17Z)-N,N-dimethyltricosa-14,17-dien-4-amine;
(19Z,22Z)-N,N-dimethyloctacosa-19,22-dien-9-amine;
(18Z,21Z)-N,N-dimethylheptacosa-18,21-dien-8-amine;
(17Z,20Z)-N,N-dimethylhexacosa-17,20-dien-7-amine;
(16Z,19Z)-N,N-dimethylpentacosa-16,19-dien-6-amine;
(22Z,25Z)-N,N-dimethylhentriaconta-22,25-dien-10-amine;
(21Z,24Z)-N,N-dimethyltriaconta-21,24-dien-9-amine;
(18Z)-N,N-dimethylheptacos-18-en-10-amine;
(17Z)-N,N-dimethylhexacos-17-en-9-amine;
(19Z,22Z)-N,N-dimethyloctacosa-19,22-dien-7-amine;
N,N-dimethylheptacosan-10-amine;
(20Z,23Z)-N-ethyl-N-methylnonacosa-20,23-dien-10-amine;
1-[(11Z,14Z)-1-nonylicosa-11,14-dien-1-yl]pyrrolidine;
(20Z)-N,N-dimethylheptacos-20-en-10-amine;
(15Z)-N,N-dimethylheptacos-15-en-10-amine;
(14Z)-N,N-dimethylnonacos-14-en-10-amine;
(17Z)-N,N-dimethylnonacos-17-en-10-amine;
(24Z)-N,N-dimethyltritriacont-24-en-10-amine;
(20Z)-N,N-dimethylnonacos-20-en-10-amine;
(22Z)-N,N-dimethylhentriacont-22-en-10-amine;
(16Z)-N,N-dimethylpentacos-16-en-8-amine;
(12Z,15Z)-N,N-dimethyl-2-nonylhenicosa-12,15-dien-1-amine;
(13Z,16Z)-N,N-dimethyl-3-nonyldocosa-13,16-dien-1-amine;
N,N-dimethyl-1-[(1S,2R)-2-octylcyclopropyl]heptadecan-8-amine;
1-[(1S,2R)-2-hexylcyclopropyl]-N,N-dimethylnonadecan-10-amine;
N,N-dimethyl-1-[(1S,2R)-2-octylcyclopropyl]nonadecan-10-amine;
N,N-dimethyl-2-[(1S,2R)-2-octylcyclopropyl]henicosan-10-amine;
N,N-dimethyl-1-[(1S,2S)-2-{[(1R,2R)-2-pentylcyclopropyl]methyl}cyclopropyl]nonadecan-10-amine;
N,N-dimethyl-1-[(1S,2R)-2-octylcyclopropyl]hexadecan-8-amine;
N,N-dimethyl-1-[(1R,2S)-2-undecylcyclopropyl]tetradecan-5-amine;
N,N-dimethyl-3-{7-[(1S,2R)-2-octylcyclopropyl]heptyl}dodecan-1-amine;
1-[(1R,2S)-2-heptylcyclopropyl]-N,N-dimethyloctadecan-9-amine;
1-[(1S ,2R)-2-decylcyclopropyl]-N,N-dimethylpentadecan-6-amine;
N,N-dimethyl-1-[(1S,2R)-2-octylcyclopropyl]pentadecan-8-amine; and
(11E,20Z,23Z)-N,N-dimethylnonacosa-11,20,23-trien-10-amine;
or a pharmaceutically acceptable salt thereof, or a stereoisomer of any of the foregoing.

In certain aspects of this embodiment of the invention, the LNPs comprise one or more of the following ionizable cationic lipids: DLinDMA, DlinKC2DMA DLin-MC3-DMA, CLinDMA, or S-Octyl CLinDMA (See International Patent Application Publication No. WO2010/021865). In other aspects of this embodiment of the invention, the LNPs comprise one or more of the following ionizable and cationic lipids: (13Z,16Z)-N,N-dimethyl-3-nonyldocosa-13,16-dien-1-amine or N,N-dimethyl-1-[(1S,2R)-2-octylcyclopropyl]hexadecan-8-amine, each of which are described in PCT/US2011/0523238, published as WO 2012/040184, the entire contents of which are hereby incorporated by reference.

In certain aspects of this embodiment of the invention, the ionizable and cationic lipid may comprise a lipid described in WO 2017/049245, the entire contents of which are hereby incorporated by reference.

In certain aspects of this embodiment of the invention, LNPs comprise one or more ionizable cationic lipids described in International Patent Application Publication No. WO2011/022460 A1, or any pharmaceutically acceptable salt thereof, or a stereoisomer of any of the compounds or salts therein.

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified plane in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the cationic lipids described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the cationic lipids of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the cationic lipids described herein is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a cationic lipid described herein has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The LNPs described herein includes each diastereoisomer of such cationic lipids and mixtures thereof.

The LNPs may also comprise any combination of two or more of the cationic lipids described herein. In certain aspects, the cationic lipid typically comprises from about 0.1 to about 99.9 mole % of the total lipid present in said particle. In certain aspects, the cationic lipid can comprise from about 80 to about 99.9% mole %. In other aspects, the cationic lipid comprises from about 2% to about 70%, from about 5% to about 50%, from about 10% to about 45%, from about 20% to about 99.8%, from about 30% to about 70%, from about 34% to about 59%, from about 20% to about 40%, or from about 30% to about 40% (mole %) of the total lipid present in said particle.

The LNPs described herein can further comprise a non-cationic lipid, which can be any of a variety of neutral uncharged, zwitterionic or anionic lipids capable of producing a stable complex. They are preferably neutral, although they can be negatively charged. Examples of noncationic lipids useful in the present invention include phospholipid-related materials, such as natural phospholipids, synthetic phospholipid derivatives, fatty acids, sterols, and combinations thereof. Natural phospholipids include phosphatidylcholine (PC), phosphatidylethanolamine (PE), and phosphatidylglycerol (PG), phosphatidylserine (PS), phosphatidylinositol (PI), Phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-Acyl-PE, phosphoinositides, and phosphosphingolipids. Phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). Fatty acids include C14:0, palmitic acid (C16:0), stearic acid (C18:0), oleic acid (C18:1), linoleic acid (C18:2), linolenic acid (C18:3), and arachidonic acid (C20:4), C20:0, C22:0 and lethicin.

In certain embodiments of the LNP described herein, the non-cationic lipid is selected from lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidyletha-nolamine (POPE) and dioleoyl-phosphatidylethanolamine 4-(N-maleimidomethyl)-cyclohexane-1-carboxylate (DOPE-mal). Noncationic lipids also include sterols such as cholesterol, stigmasterol or stigmastanol. Cholesterol is known in the art. See U.S. Patent Application Publication Nos: U.S. 2006/0240554 and U.S. 2008/0020058. In certain embodiments, the LNP comprise a combination of a phospholipid and a sterol.

Where present, the non-cationic lipid typically comprises from about 0.1% to about 65%, about 2% to about 65%, about 10% to about 65%, or about 25% to about 65% expressed as mole percent of the total lipid present in the LNP. The LNPs described herein further include a polyethyleneglycol (PEG) lipid conjugate ("PEG-lipid") which may aid as a bilayer stabilizing component. The lipid component of the PEG lipid may be any non-cationic lipid described above including natural phospholipids, synthetic phospholipid derivatives, fatty acids, sterols, and combinations thereof. In certain embodiments of the LNPs described herein, the PEG-lipids include, PEG coupled to dialkyloxypropyls (PEG-DAA) as described in, e.g., International Patent Application Publication No. WO 05/026372, PEG coupled to diacylglycerol (PEG-DAG) as described in, e.g., U.S. Patent Publication Nos. 20030077829 and 2005008689; PEG coupled to phosphatidylethanolamine (PE) (PEG-PE), or PEG conjugated to 1,2-Di-O-hexadecyl-sn-glyceride (PEG-DSG), or any mixture thereof (see, e.g., U.S. Pat. No. 5,885,613).

In one embodiment, the PEG-DAG conjugate is a dilaurylglycerol (C 12)-PEG conjugate, a PEG dimyristylglycerol (C14)conjugate, a PEG-dipalmitoylglycerol (C16) conjugate, a PEG-dilaurylglycamide (C12) conjugate, a PEG-dimyristylglycamide (C14) conjugate, a PEG-dipalmitoylglycamide (C16) conjugate, or a PEG-disterylglycamide (C18). Those of skill in the art will readily appreciate that other diacylglycerols can be used in the PEG-DAG conjugates.

In certain embodiments, PEG-lipids include, but are not limited to, PEG-dimyristolglycerol (PEG-DMG), PEG-disteryl glycerol (PEG-DSG), PEG-dipalmetoleyl, PEG-dioleyl, PEG-distearyl, PEG-diacylglycamide (PEG-DAG), PEG- dipalmitoyl phosphatidylethanolamine (PEG-DPPE), and PEG-1,2-dimyristyloxlpropyl-3-amine (PEG-c-DMA).

In certain embodiments, the PEG-lipid is PEG coupled to dimyristoylglycerol (PEG-DMG), e.g., as described in Abrams et al., 2010, Molecular Therapy 18(1):171, and U.S. Patent Application Publication Nos. US 2006/0240554 and US 2008/0020058, including for example, 2KPEG/PEG200-DMG.

In certain embodiments, the PEG-lipid, such as a PEG-DAG, PEG-cholesterol, PEG-DMB, comprises a polyethylene glycol having an average molecular weight ranging of about 500 daltons to about 10,000 daltons, of about 750 daltons to about 5,000 daltons, of about 1,000 daltons to about 5,000 daltons, of about 1,500 daltons to about 3,000 daltons or of about 2,000 daltons. In certain embodiments, the PEG-lipid comprises PEG400, PEG1500, PEG2000 or PEG5000.

The acyl groups in any of the lipids described above are preferably acyl groups derived from fatty acids having about C10 to about C24 carbon chains. In one embodiment, the acyl group is lauroyl, myristoyl, palmitoyl, stearoyl or oleoyl.

The PEG-lipid conjugate typically comprises from about 0.1% to about 15%, from about 0.5% to about 20%, from about 1.5% to about 18%, from about 4% to about 15%, from about 5% to about 12%, from about 1% to about 4%, or about 2% expressed as a mole % of the total lipid present in said particle.

In certain embodiments of the invention, the LNPs comprise one or more cationic lipids, cholesterol and 1,2-Dimyristoyl-sn-glycerol methoxypolyethylene glycol (PEG-DMG). In certain embodiments the invention, the LNPs comprise one or more cationic lipids, cholesterol, 1,2-Distearoyl-sn-glycero-3-phosphocholine (DSPC), and 1,2-Dimyristoyl-sn-glycerol methoxypolyethylene glycol (PEG-DMG).

In certain embodiments of the invention, the LNPs comprise lipid compounds assembled within the following molar ratios:

Cationic Lipid (20-99.8 mole %)
Non-cationic lipid (0.1-65 mole %) and
PEG-DMG (0.1-20 mole %).

In certain embodiments of the invention, the LNPs comprise lipid compounds assembled within the following molar ratios:

Cationic Lipid (30-70 mole %)
Non-cationic lipid (20-65 mole %) and
PEG-DMG (1-15 mole %).

In certain aspects of this embodiment, the non-cationic lipid is cholesterol. Exemplary LNPs may include cationic lipid/cholesterol/PEG-DMG at about the following molar ratios: 58/30/10.

In certain aspects of this embodiment, the non-cationic lipid is cholesterol and DSPC. Exemplary LNPs may include cationic lipid/cholesterol/DSPC/PEG-DMG at about the following molar ratios: 59/30/10/1; 58/30/10/2; 43/41/15/1; 42/41/15/2; 40/48/10/2; 39/41/19/1; 38/41/19/2; 34/41/24/1; and 33/41/24/2.

Preparation of LNPs

LNPs can be formed, for example, by a rapid precipitation process which entails micro-mixing the lipid components dissolved in ethanol with an aqueous solution using a confined volume mixing apparatus such as a confined volume T-mixer, a multi-inlet vortex mixer (MIVM), or a microfluidics mixer device as described below. The lipid solution contains one or more cationic lipids, one or more noncationic lipids (e.g., DSPC), PEG-DMG, and optionally cholesterol, at specific molar ratios in ethanol. The aqueous solution consists of a sodium citrate or sodium acetate buffered salt solution with pH in the range of 2-6, preferably 3.5-5.5. The two solutions are heated to a temperature in the range of 25° C.-45° C., preferably 30° C.-40° C., and then mixed in a confined volume mixer thereby instantly forming the LNP. When a confined volume T-mixer is used, the T-mixer has an internal diameter (ID) range from 0.25 to 1.0 mm. The alcohol and aqueous solutions are delivered to the inlet of the T-mixer using programmable syringe pumps, and with a total flow rate from 10-600 mL/minute. The alcohol and aqueous solutions are combined in the confined-volume mixer with a ratio in the range of 1:1 to 1:3 vol:vol, but targeting 1:1.1 to 1:2.3. The combination of ethanol volume fraction, reagent solution flow rates and t-mixer tubing ID utilized at this mixing stage has the effect of controlling the particle size of the LNPs between 30 and 300 nm. The resulting LNP suspension is twice diluted into higher pH buffers in the range of 6-8 in a sequential, multi-stage in-line mixing process. For the first dilution, the LNP suspension is mixed with a buffered solution at a higher pH (pH 6-7.5) with a mixing ratio in the range of 1:1 to 1:3 vol:vol, but targeting 1:2 vol:vol. This buffered solution is at a temperature in the range of 15-40° C., targeting 30-40° C. The resulting LNP suspension is further mixed with a buffered solution at a higher pH, e.g., 6-8 and with a mixing ratio in the range of 1:1 to 1:3 vol:vol, but targeting 1:2 vol:vol. This later buffered solution is at a temperature in the range of 15-40° C., targeting 16-25° C. The mixed LNPs are held from 30 minutes to 2 hours prior to an anion exchange filtration step. The temperature during incubation period is in the range of 15-40° C., targeting 30-40° C. After incubation, the LNP suspension is filtered through a 0.8 µm filter containing an anion exchange separation step. This process uses tubing IDs ranging from 1 mm ID to 5 mm ID and a flow rate from 10 to 2000 mL/minute. The LNPs are concentrated and diafiltered via an ultrafiltration process where the alcohol is removed and the buffer is exchanged for the final buffer solution such as phosphate buffered saline or a buffer system suitable for cryopreservation (for example containing sucrose, trehalose or combinations thereof). The ultrafiltration process uses a tangential flow filtration format (TFF). This process uses a membrane nominal molecular weight cutoff range from 30-500 KD, targeting 100 KD. The membrane format can be hollow fiber or flat sheet cassette. The TFF processes with the proper molecular weight cutoff retains the LNP in the retentate and the filtrate or permeate contains the alcohol and final buffer wastes. The TFF process is a multiple step process with an initial concentration to a lipid concentration of 20-30 mg/mL. Following concentration, the LNP suspension is diafiltered against the final buffer (for example, phosphate buffered saline (PBS) with pH 7-8, 10 mM Tris, 140 mM NaCl with pH 7-8, or 10 mM Tris, 70 mM NaCl, 5 wt % sucrose, with pH 7-8) for 5-20 volumes to remove the alcohol and perform buffer exchange. The material is then concentrated an additional 1-3 fold via ultrafiltration. The final steps of the LNP manufacturing process are to sterile filter the concentrated LNP solution into a suitable container under aseptic conditions. Sterile filtration is accomplished by passing the LNP solution through a pre-filter (Acropak 500 PES 0.45/0.8 µm capsule) and a bioburden reduction filter (Acropak 500 PES 0.2/0.8 µm capsule). Following filtration, the vialed LNP product is stored under suitable storage conditions (2° C.-8° C., or −20° C. if frozen formulation).

In some embodiments, the LNPs of the compositions provided herein have a mean geometric diameter that is less than 1000 nm. In some embodiments, the LNPs have mean geometric diameter that is greater than 50 nm but less than 500 nm. In some embodiments, the mean geometric diameter of a population of LNPs is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm. In some embodiments, 30%, 40%, 50%, 60%, 70%, 80%, 90%, or more of the LNPs of a population of LNPs have a diameter that is less than 500 nm. In some embodiments, 10%, 20%, 30%, 40%, 50%, 60%, 70%, 80%, 90%, or more of the LNPs of a population of LNPs have a diameter that is greater than 50 nm but less than 500 nm. In some embodiments, 10%, 20%, 30%, 40%, 50%, 60%, 70%, 80%, 90%, or more of the LNPs of a population of LNPs have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the LNPs of a population of LNPs have a diameter that is between 100-400 nm, 100-300 nm, 100-250 nm, or 100-200 nm. In some embodiments, 10%, 20%, 30%, 40%, 50%, 60%, 70%, 80%, 90%, or more of the LNPs of a population of LNPs have a diameter that is between 60-400 nm, 60-350 nm, 60-300 nm, 60-250 nm, or 60-200 nm.

In a particular embodiment, the size of the LNPs ranges between about 1 and 1000 nm, preferably between about 10 and 500 nm, more preferably between about 100 to 300 nm, and preferably 100 nm.

Nucleic Acids/Polynucleotides

DNA of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally-occurring or wild-type sequence.

In some embodiments, a codon-optimized sequence shares between 65% and 85% (e.g., between about 67% and about 85%, or between about 67% and about 80%) sequence identity to a naturally-occurring sequence or a wild-type sequence. In some embodiments, a codon-optimized sequence shares between 65% and 75%, or about 80% sequence identity to a naturally-occurring sequence or wild-type sequence.

Methods of Treatment

Provided herein are compositions (e.g., pharmaceutical compositions), methods, kits and reagents for prevention and/or treatment of RSV in humans and other mammals. RSV virus vaccines can be used as therapeutic or prophylactic agents. They may be used in medicine to prevent and/or treat infectious disease. In exemplary aspects, the RSV immunogenic compositions of the present disclosure are used as vaccines to provide prophylactic protection from RSV virus. Prophylactic protection from RSV virus can be achieved following administration of an RSV vaccine of the present disclosure. Vaccines can be administered once, twice, three times, four times or more. It is possible, although less desirable, to administer the vaccine to an infected individual to achieve a therapeutic response. Dosing may need to be adjusted accordingly.

In some embodiments, the RSV immunogenic compositions of the present disclosure can be used as a method of preventing an RSV infection in a subject, the method comprising administering to said subject at least one RSV immunogenic composition as provided herein. In some embodiments, the RSV immunogenic compositions of the present disclosure can be used as a method of treating an RSV infection in a subject, the method comprising administering to said subject at least one RSV immunogenic composition as provided herein.

In some embodiments, the RSV immunogenic compositions of the present disclosure can be used as a method of reducing an incidence of RSV in a subject, the method comprising administering to said subject at least one RSV immunogenic composition as provided herein. In some embodiments, the RSV immunogenic composition of the present disclosure can be used as a method of inhibiting spread of RSV from a first subject infected with RSV to a second subject not infected with RSV, the method comprising administering to at least one of said first subject and said second subject at least one RSV immunogenic composition as provided herein.

A method of eliciting an immune response in a subject against RSV is provided in aspects of the invention. The method involves administering to the subject an RSV immunogenic composition described herein, thereby inducing in the subject an immune response specific to RSV.

A prophylactically effective dose is a therapeutically effective dose that prevents infection with the virus at a clinically acceptable level. In some embodiments the therapeutically effective dose is a dose listed in a package insert for the vaccine.

Therapeutic and Prophylactic Compositions

Provided herein are compositions (e.g., pharmaceutical compositions), methods, kits and reagents for prevention, treatment or diagnosis of RSV in humans and other mammals, for example. The RSV immunogenic compositions, including vaccines, can be used as therapeutic or prophylactic agents. They may be used in medicine to prevent and/or treat infectious disease. In some embodiments, the RSV immunogenic compositions in accordance with the present disclosure may be used for treatment of RSV.

RSV immunogenic compositions, including RSV vaccines, may be administered prophylactically or therapeutically as part of an active immunization scheme to healthy individuals or early in infection during the incubation phase or during active infection after onset of symptoms. In some embodiments, the amount of vaccine of the present disclosure provided to a cell, a tissue or a subject may be an amount effective for immune prophylaxis.

RSV immunogenic compositions, including RSV vaccines, may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, RSV immunogenic compositions, including RSV vaccines, may be administered intramuscularly, intradermally, or intranasally, similarly to the administration of inactivated vaccines known in the art. In some embodiments, RSV immunogenic compositions, including RSV vaccines, are administered intramuscularly.

RSV immunogenic compositions, including RSV vaccines, may be utilized in various settings depending on the prevalence of the infection or the degree or level of unmet medical need. Vaccines have superior properties in that they produce much larger antibody titers and produce responses early than commercially available anti-viral agents/compositions.

Provided herein are pharmaceutical compositions including RSV immunogenic compositions optionally in combination with one or more pharmaceutically acceptable excipients.

RSV immunogenic compositions, which include RSV vaccines, may be formulated or administered alone or in conjunction with one or more other components. For instance, such compositions may comprise other components including, but not limited to, adjuvants.

In some embodiments, the RSV immunogenic compositions do not include an adjuvant (they are adjuvant free).

Aluminium has long been shown to stimulate the immune response against co-administered antigens, primarily by stimulating a TH2 response. It is preferred that the aluminium adjuvant of the compositions provided herein is not in the form of an aluminium precipitate. Aluminium-precipitated vaccines may increase the immune response to a target antigen, but have been shown to be highly heterogeneous preparations and have had inconsistent results see Lindblad E. B. Immunology and Cell Biology 82: 497-505 (2004)). Aluminium-adsorbed vaccines, in contrast, can be preformed in a standardized manner, which is an essential characteristic of vaccine preparations for administration into humans. Moreover, it is thought that physical adsorption of a desired antigen onto the aluminium adjuvant has an important role in adjuvant function, perhaps in part by allowing a slower clearing from the injection site or by allowing a more efficient uptake of antigen by antigen presenting cells.

The aluminium adjuvant of the present invention may be in the form of aluminium hydroxide ($Al(OH)_3$), aluminium phosphate ($AlPO_4$), aluminium hydroxyphosphate, amorphous aluminium hydroxyphosphate sulfate (AAHS) or so-called "alum" ($KAl(SO4)-12H2O$) see Klein et al, Analysis of aluminium hydroxyphosphate vaccine adjuvants by (27) Al MAS NMR., J. Pharm. Sci. 89(3): 311-21 (2000)). In exemplary embodiments of the invention provided herein, the aluminium adjuvant is aluminium hydroxyphosphate or AAHS. The ratio of phosphate to aluminium in the aluminium adjuvant can range from 0 to 1.3. In preferred embodiments of this aspect of the invention, the phosphate to aluminium ratio is within the range of 0.1 to 0.70. In particularly preferred embodiments, the phosphate to aluminium ratio is within the range of 0.2 to 0.50. MAPA is an aqueous suspension of aluminum hydroxyphosphate. MAPA is manufactured by blending aluminum chloride and sodium phosphate in a 1:1 volumetric ratio to precipitate aluminum hydroxyphosphate. After the blending process, the material is size-reduced with a high-shear mixer to achieve a target aggregate particle size in the range of 2-8 µm. The product is then diafiltered against physiological saline and steam sterilized. See, e.g., International Patent Application Publication No. WO2013/078102.

In some embodiments of the invention, the aluminium adjuvant is in the form of AAHS (referred to interchangeably herein as Merck aluminium adjuvant (MAA)). MAA carries zero charge at neutral pH, while AlOH carries a net positive charge and $AlPO_4$ typically carries a net negative charge at neutral pH.

One of skill in the art will be able to determine an optimal dosage of aluminium adjuvant that is both safe and effective at increasing the immune response to the targeted antigenic polypeptides. For a discussion of the safety profile of aluminium, as well as amounts of aluminium included in FDA-licensed vaccines, see Baylor et al., Vaccine 20: S18-S23 (2002). Generally, an effective and safe dose of aluminium adjuvant varies from 150 to 600 µg/dose (300 to 1200 µg/mL concentration). In specific embodiments of the formulations and compositions of the present invention, there is between 200 and 300 µg aluminium adjuvant per dose of vaccine. In alternative embodiments of the formulations and compositions of the present invention, there is between 300 and 500 µg aluminium adjuvant per dose of vaccine.

RSV immunogenic compositions, including RSV vaccines, may be formulated or administered in combination with one or more pharmaceutically-acceptable excipients. In some embodiments, the compositions comprise at least one additional active substances, such as, for example, a therapeutically-active substance, a prophylactically-active substance, or a combination of both. The compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety). In some embodiments, the RSV immunogenic compositions, including RSV vaccines, are administered to humans, human patients or subjects.

Formulations of the RSV immunogenic compositions described herein may be prepared by any method known or hereafter developed in the art of pharmacology. In general, such preparatory methods include the step of bringing the active ingredient (e.g.,polypeptide or polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Modes of Vaccine Administration

RSV immunogenic compositions, including RSV vaccines, may be administered by any route which results in a therapeutically effective outcome. These include, but are not limited, to intradermal, intramuscular, intranasal and/or subcutaneous administration. The present disclosure provides methods comprising administering compositions to a subject in need thereof. The exact amount required will vary from subject to subject, depending on the species, age, and general condition of the subject, the severity of the disease, the particular composition, its mode of administration, its mode of activity, and the like. RSV immunogenic compositions are typically formulated in dosage unit form for ease of administration and uniformity of dosage. It will be understood, however, that the total daily usage of vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, RSV immunogenic compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect. In exemplary embodiments, RSV immunogenic compositions vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, the RSV immunogenic compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

An RSV immunogenic pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, intranasal and subcutaneous).

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Generation of Single Chain Mutants Having $F_1$ and $F_2$ Fragments Joined by a Peptide Linker Wildtype RSV F polypeptide is cleaved into $F_1$ and $F_2$ fragments by host furin protease post translation. To evaluate single chain RSV mutants which are not cleaved by furin and which remain as a single polypeptide, amino acids 98-146 of WT RSV (which amino acids include the furin cleavage sites, the p27 peptide and part of the fusion peptide) were replaced with a flexible amino acid linker of various lengths (8-14 a.a.), in the background of prefusion stabilizing DS-Cav1 mutations (S155C, S190F, V207L, and S290C) (McLellan et al. 2013). In these mutants, the T4 phage fibritin trimerization domain (foldon) was appended to the C-terminus of the RSV F ectodomain, followed by a protease cleavage site and purification tags. Mutant RSV F sequences were codon optimized for mammalian codon usage, cloned into an expression vector, and transiently transfected into Expi293 suspension cells (Life Technologies). Cell culture supernatants were harvested day 3 to 7 post-plasmid transfection to assess binding of these mutants to different antibodies against RSV F. Briefly, 96-well Ni-NTA coated plates (Thermo Scientific) were coated with cell culture supernatants for 1 hour at room temperature. Unbound sites were blocked by addition of 2% (v/v) bovine serum albumin (BSA) in PBS and incubation for 1 hour at room temperature. Plates were washed with PBS containing 0.05% (v/v) Tween™ 20 (polysorbate 20) (PBS-T) and incubated with serial dilutions of antibodies (D25 or Synagis® (palivizumab)) at room temperature for 1 hour. Plates were washed again with PBS-T and incubated for 1 hour at room temperature with goat anti-human IgG HRP-conjugated secondary antibody (Thermo Fisher) diluted 1:2,000. Following an additional wash with PBS-T and brief rinse with ddH$_2$O, Super AquaBlue ELISA substrate (eBiosience) was added, and the plate was immediately read at 405 nm for 5 min. mOD/min was calculated for each well.

Figure 1B:
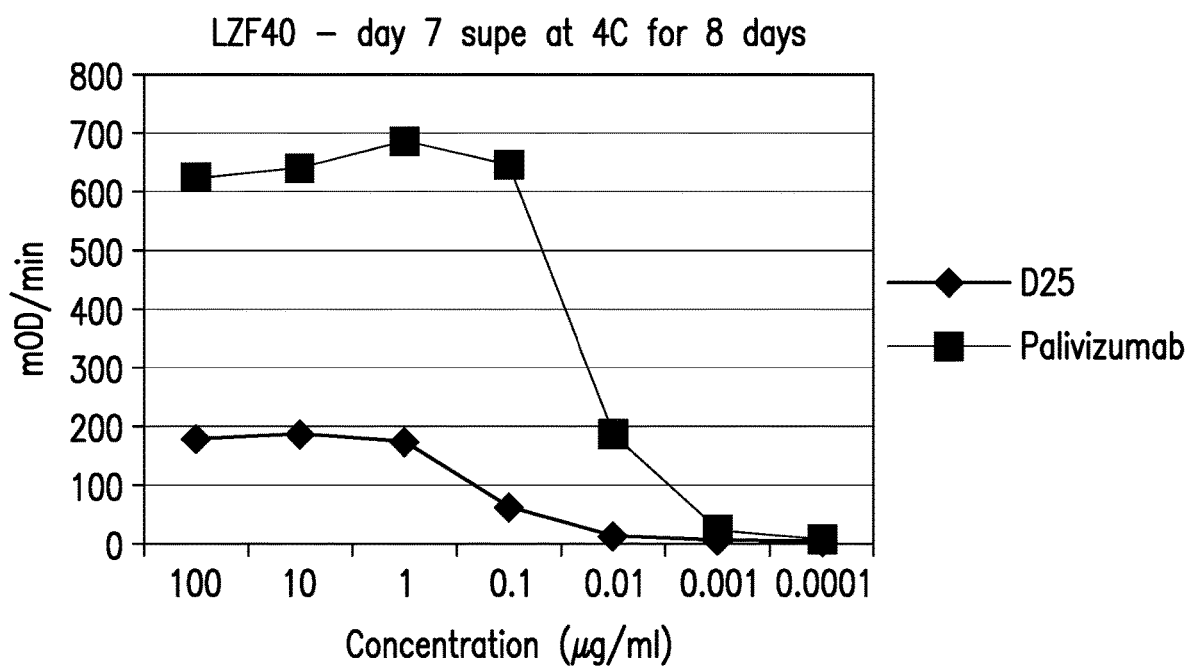
Figure 2A:
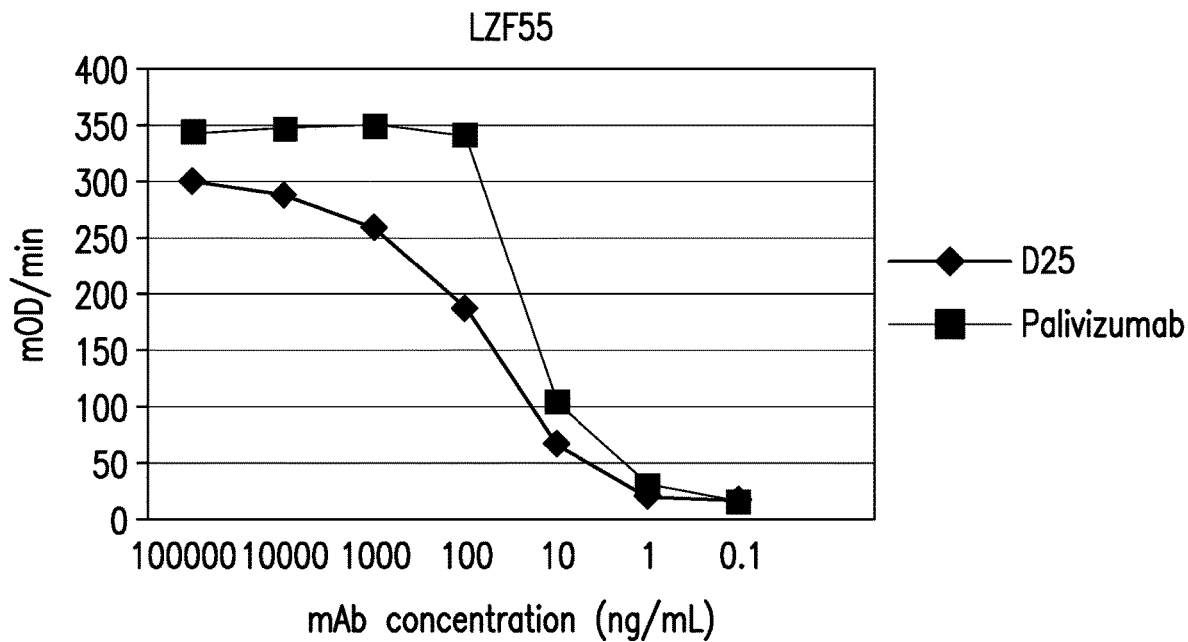
FIGS. 2A-2F show binding of freshly harvested day 3 post-transfection cell culture supernatants (supe) of LZF55 (F55), LZF 56 (F56) and LZF57 (F57) (DS-Cav1 with 10, 12 or 14 a.a. linker, respectively.
Figure 2B:
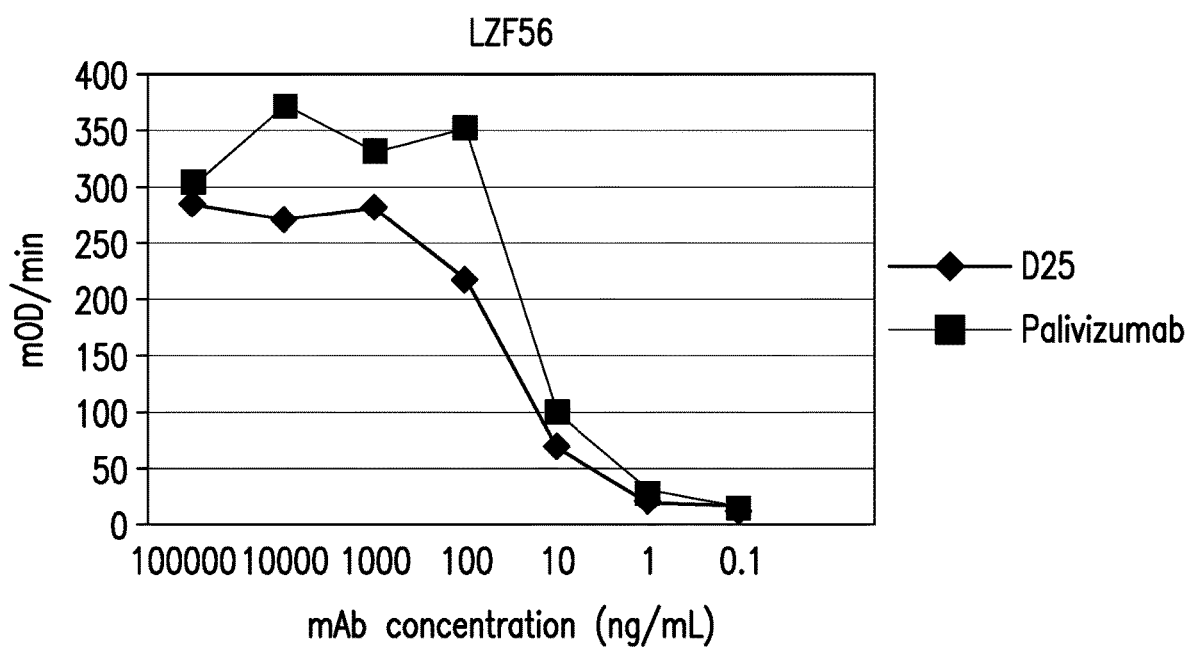
Figure 2C:
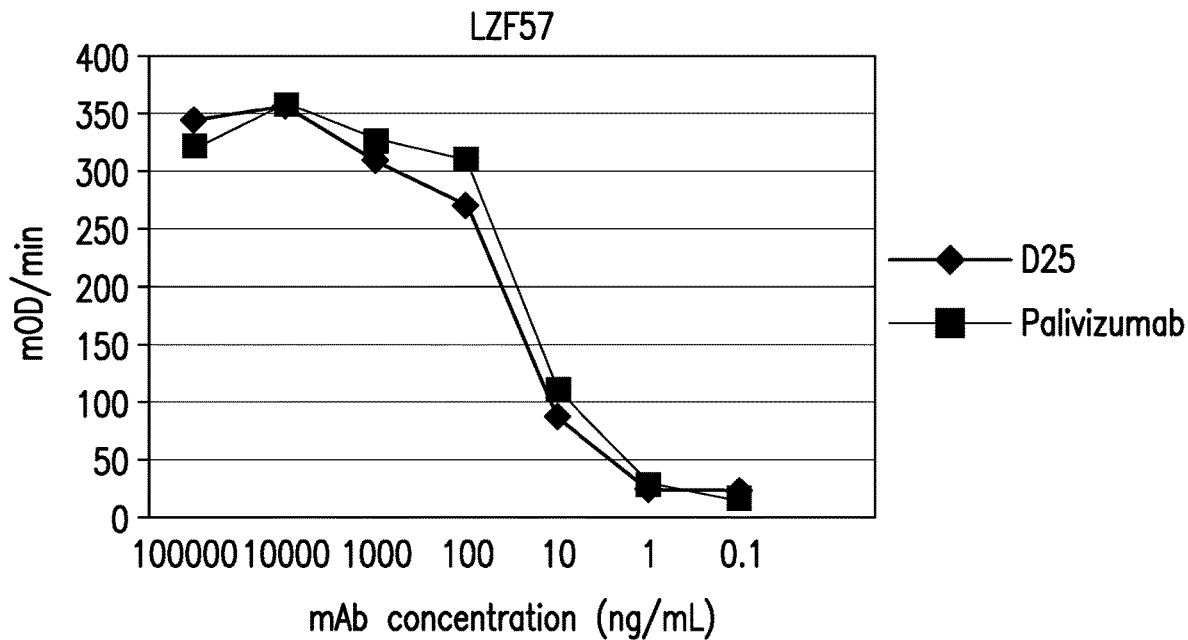
Figure 2D:
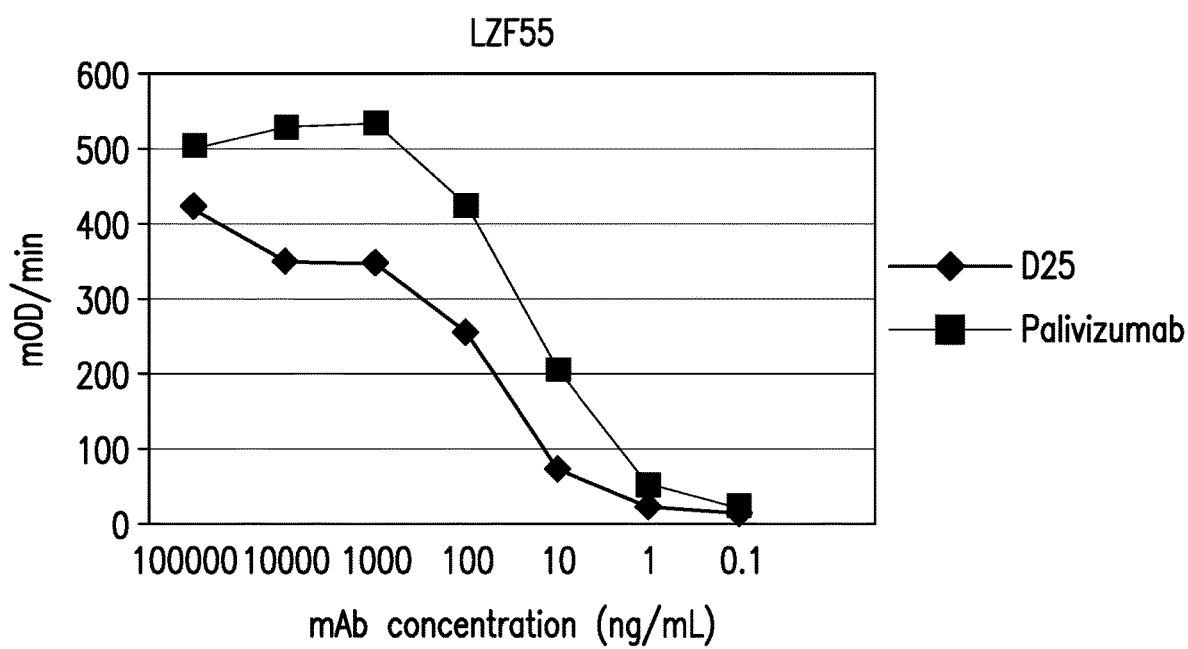
Figure 2E:
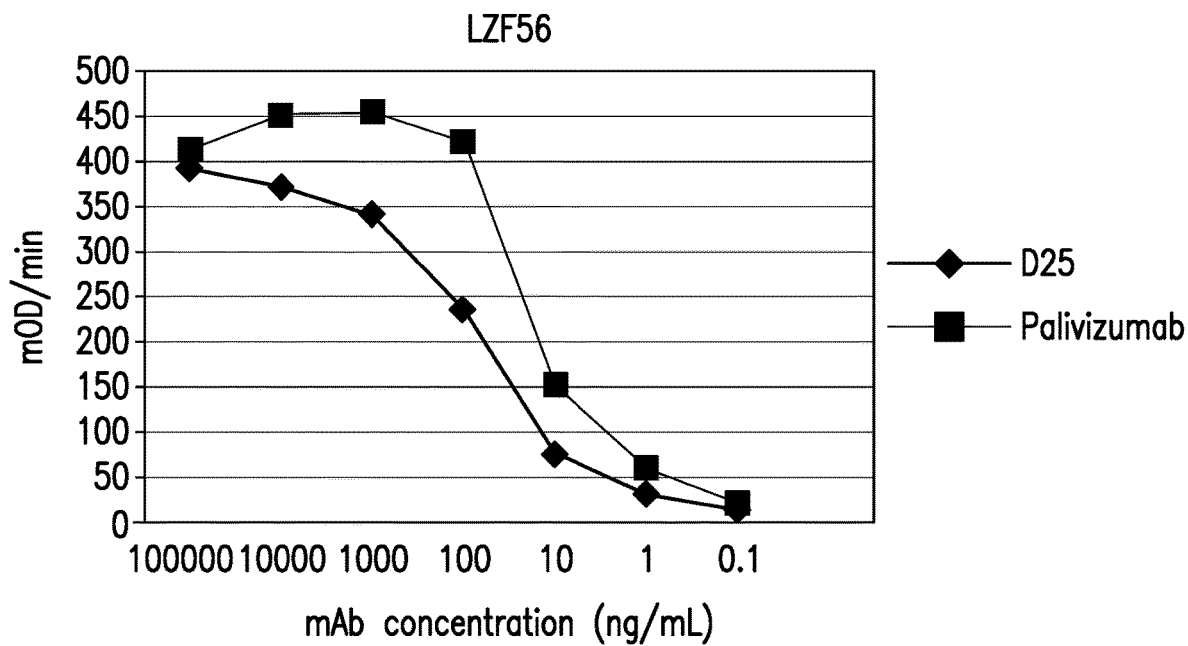
Figure 2F:
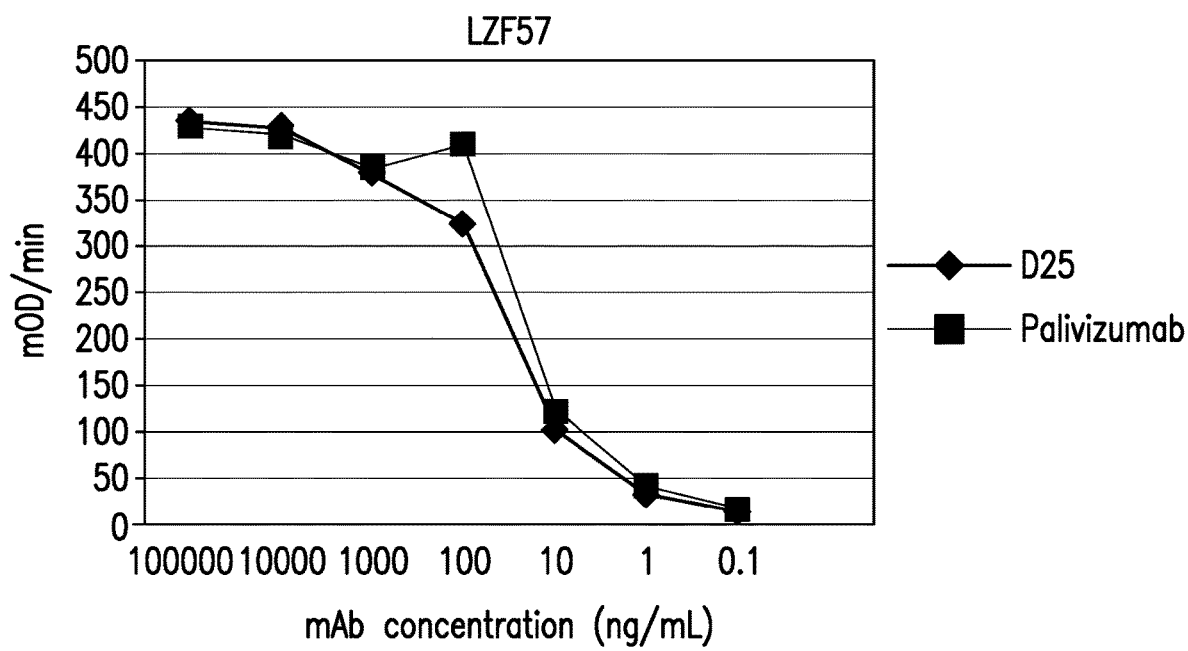

FIGS. 1A and 1B show binding of freshly harvested day 7 post-transfection cell culture supernatants of construct 40a (DS-Cav1 with an 8 a.a. linker) (FIG. 1A) or those stored at 4° C. for 8 days (FIG. 1B) to D25 and Synagis® (palivizumab) monoclonal antibodies. The LZF40a mutant exhibited low prefusion-specific mAb D25 binding. Binding to palivizumab (which reacts to both prefusion and postfusion F) was high, suggesting that the mutant was expressed well. FIGS. 2A and 2B show binding of freshly harvested day 3 post-transfection cell culture supernatants of LZF55a, LZF56a, and LZF57a (DS-Cav1 with 10, 12 or 14 amino acid linker, respectively; FIGS. 2A, 2B, 2C, respectively) or those stored at 4° C. for 7 days (FIGS. 2D, 2E, and 2F, respectively) to D25 and palivizumab. All of the three mutants expressed well, based on the reactivity to palivizumab. Among these mutants, LZF57a (DS-Cav1 with a 14 amino acid linker) exhibited the highest prefusion-specific mAb D25 binding and retained D25 binding after 7 days of storage at 4° C.

Figure 3:
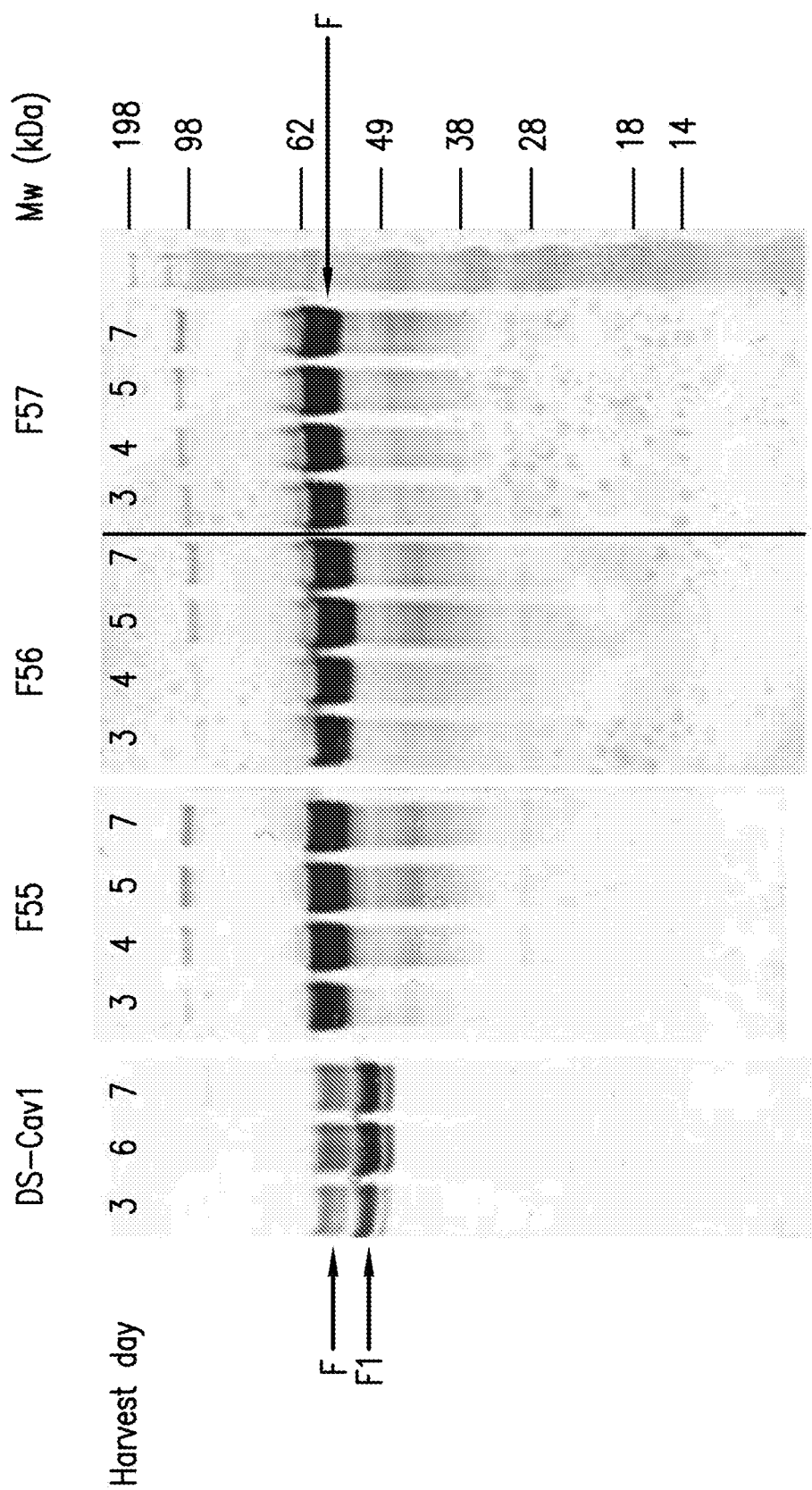
FIG. 3 shows the results of a western blot with anti-RSV F sera for single chain RSV mutants LZF55, LZF56 and LZF57 compared to DS-Cav1.

In addition to ELISA, cell culture supernatants harvested at different post-transfection time points were analyzed on a western blot with anti-RSV F sera. Supernatants were treated with SDS loading buffer with reducing agent (Life Technologies), applied to gel electrophoresis and then electro-transferred onto nitrocellulose membranes (Life Technologies). The membranes were blocked overnight at 4° C. in blotting grade blocker (BioRad) made in 1× TBST (Tris Buffered saline+tween). The membranes were incubated with polyclonal guinea pig sera against ectodomain of wildtype RSV F protein (Sino Biological) followed by an AP-conjugated goat anti-guinea pig IgG secondary antibody (Santa Cruz Biotechnology). Single chain RSV mutants LZF55a, LZF56a, and LZF57a showed significantly improved expression levels compared to the original DS-Cav1 (FIG. 3). DS-Cav1 appeared as two bands on the gel: an upper band represents the uncleaved F protein, and a lower band represents the furin cleaved $F_1$ fragment. The single chain RSV mutants LZF55, LZF56, and LZF57 appeared as a single predominant band on the gel, representing uncleaved F.

Example 2

Additional Stabilizing Mutations

Figure 4A:
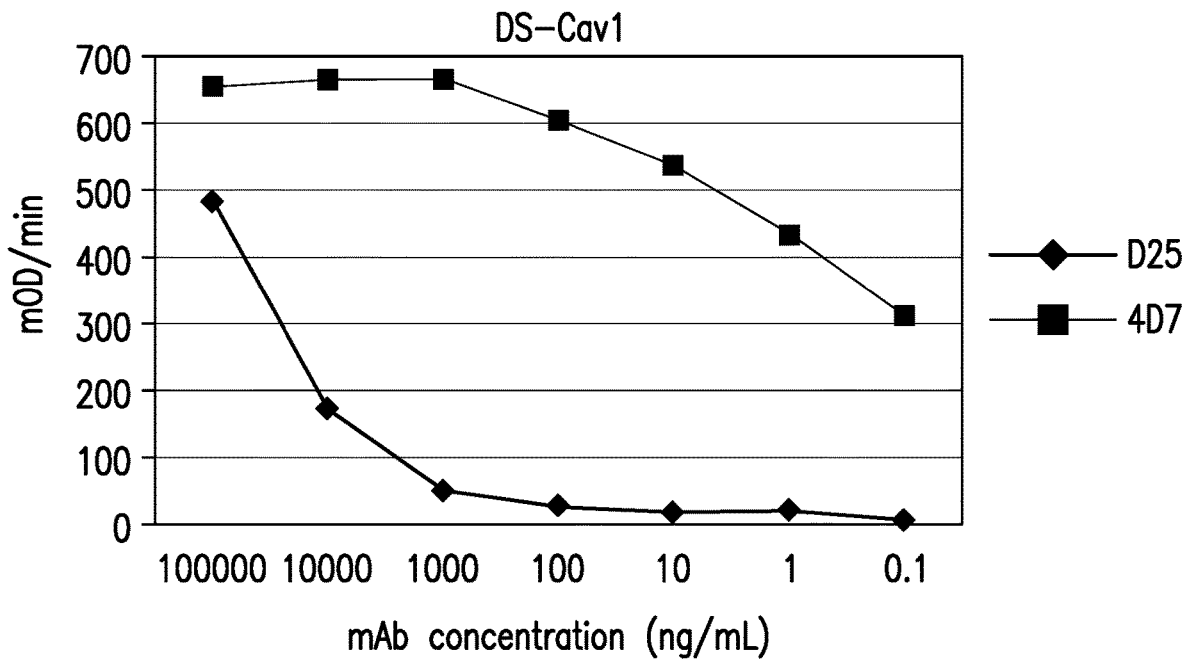
FIGS. 4A-4C show binding of freshly harvested cell culture supernatants of DS-Cav1 (FIG. 4A), LZF57 (FIG. 4B) or LZF111 (FIG. 4C) to D25 and 4D7 monoclonal antibodies as determined by ELISA.
Figure 4B:
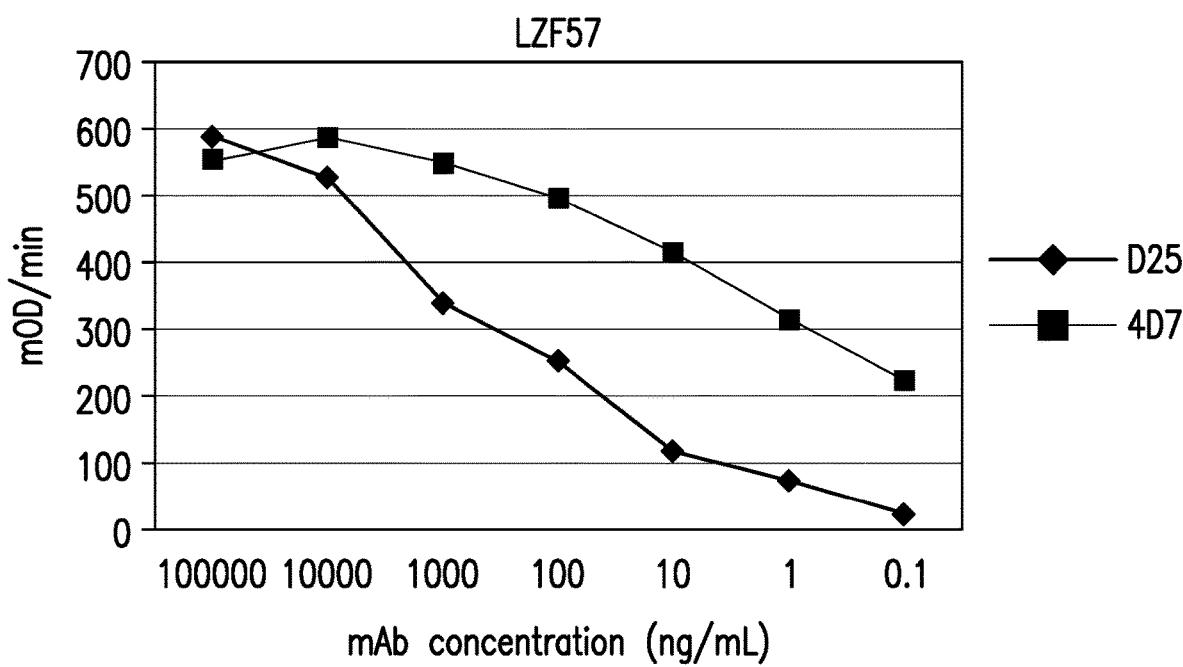
Figure 4C:
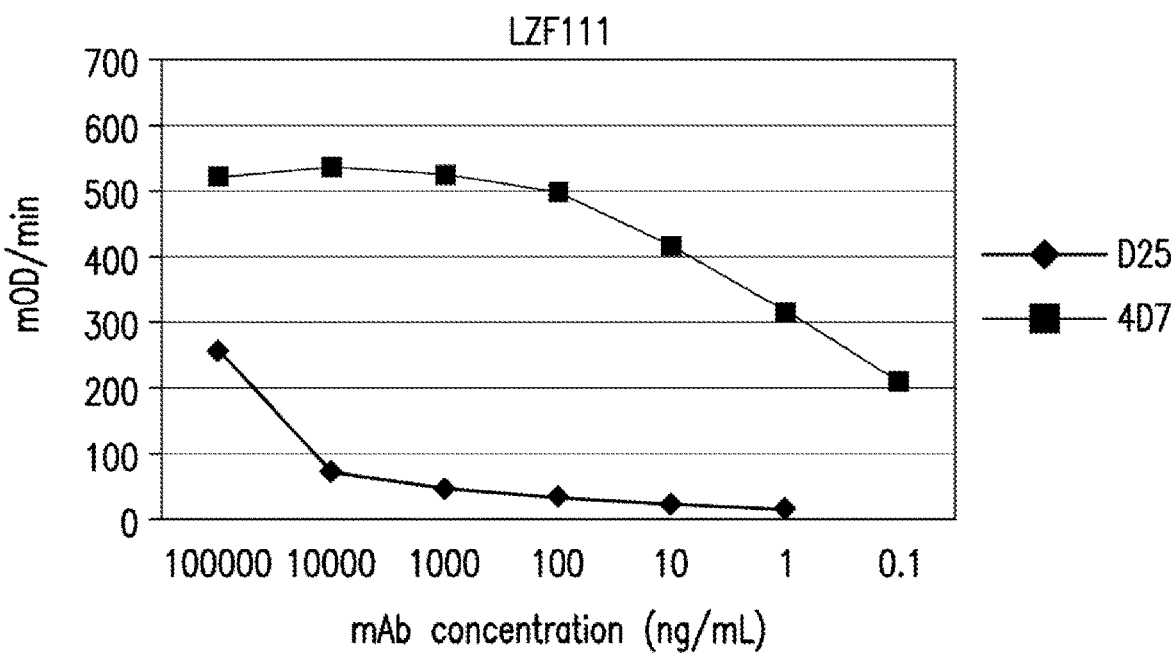

Monoclonal antibody, 4D7, which reacts to antigenic site I on the RSV postfusion F protein and can be used to assess the stability of the prefusion F structure (Flynn et al. 2016). Freshly harvested cell culture supernatants of DS-Cav1 or construct LZF57a were assessed by ELISA for D25 and 4D7 binding (FIG. 4C). Although construct LZF57a retained D25 binding, indicating its prefusion conformation, it appeared to exhibit increased 4D7 binding compared to the original DS-Cav1 construct, suggesting that there might be subtle conformational change when the single chain linker was introduced. To further stabilize the LZF57a single chain RSV mutant construct, structure-based design was performed to generate variants with disulfide bond mutations; cavity filling mutations; and/or postfusion-destabilization mutations. Especially, model of a disulfide mutant D486C/D489C based on crystal structure of the prefusion F protein suggested that an inter-molecular disulfide bond within 3.8 Å might help to further stabilize the prefusion conformation (data not shown).

Figure 4D:
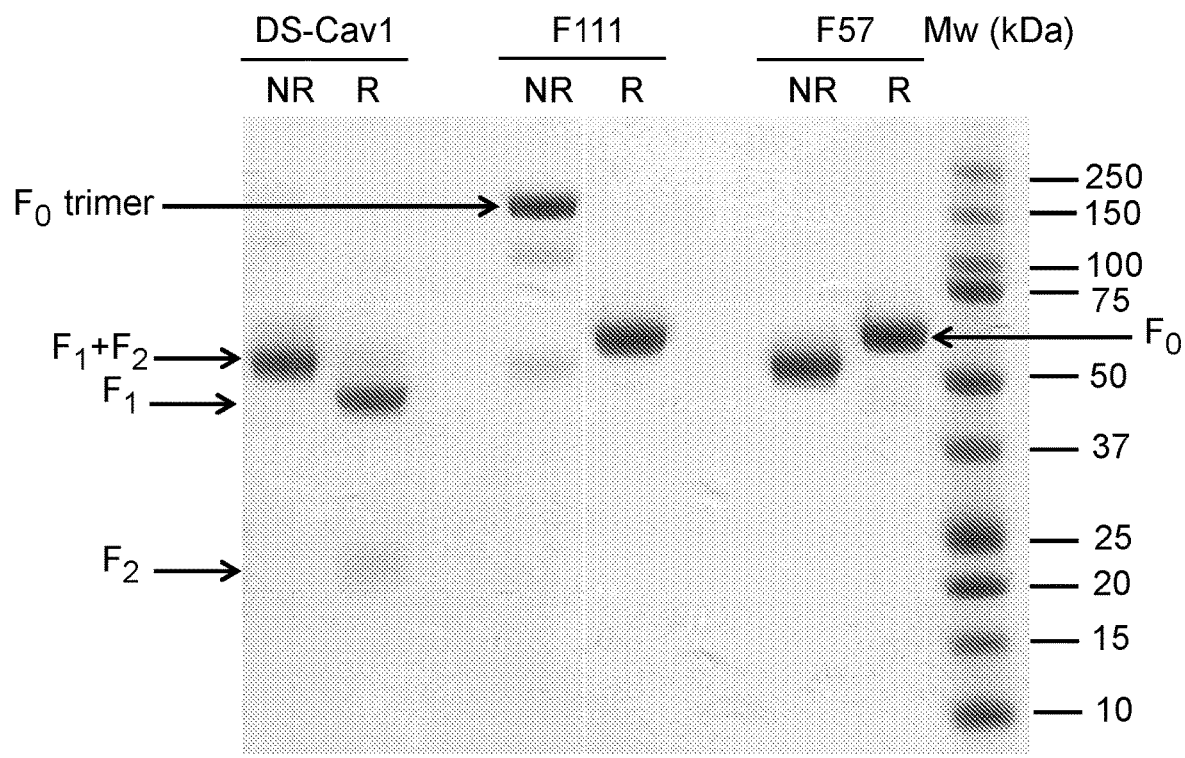
FIG. 4D shows purified DS-Cav1, F57 and F111 analyzed by SDS-PAGE under reducing (R) or non-reducing (N FIG. 12 sets forth serum antibody competition ELISA titers ($IT_{50}$ Individual and GMT with 95% Confidence intervals) against D25 (site 0), palivizumab (site II), and 4D7 (site I) measured at Day 56 (4 weeks PD2).
Figure 10:
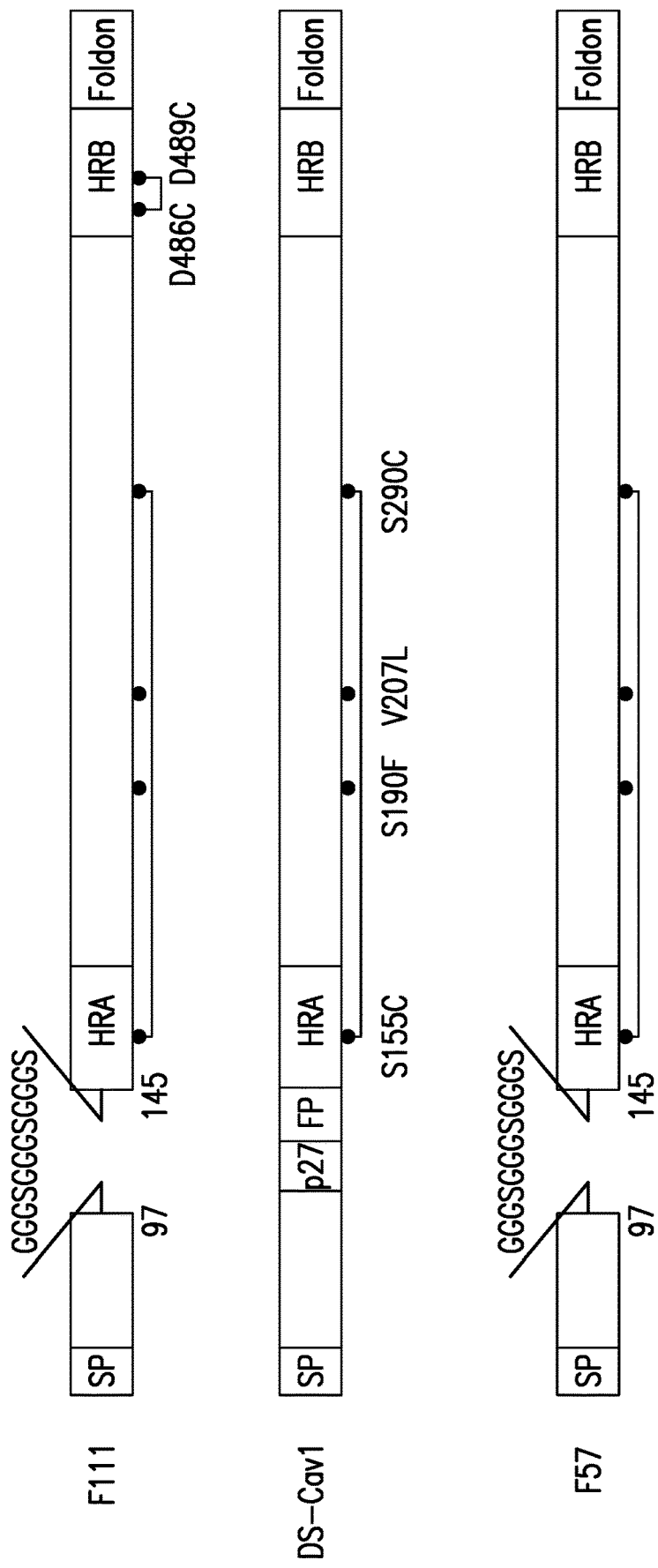

Selected mutations were combined with the LZF57a mutations, and evaluated with prefusion specific mAb D25 and 4D7 as described above. Mutant LZF 111a (which corresponds to LZF57a with D486C/D489C mutation) exhibited decreased 4D7 binding compared to construct LZF57a, suggesting that it might adopt a more prefusion-like conformation (FIGS. 4B, 4C, and 4D). FIG. 10 sets forth the schematic of the LZF111 and LZF57 constructs.

To further characterize the LZF111 mutant, RSV F proteins (DS-Cavi and LZF111a) were purified from culture supernatants with a modified method adopted from previously described (McLellan 2013). Briefly, his tagged proteins were purified using Ni-Sepharose chromatography (GE Healthcare). Tags were removed by overnight digestion with thrombin. Digestion was performed during dialysis to reduce imidazole concentration. To remove co-eluting contaminants and uncleaved F protein, samples were subjected to a second Ni-Sepharose chromatography step. F proteins were further purified by gel filtration chromatography (Superdex 200, GE Healthcare) and were stored in a buffer of 50 mM HEPES pH 7.5, 300 mM NaCl. SDS-PAGE analysis was performed under reducing and non-reducing conditions to assess the disulfide bond formations (FIG. 4D). In brief, purified protein samples were treated with SDS loading buffer with or without reducing agent (Life Technologies), heated at 95° C. for 2-3 minutes, and applied to NuPAGE (Invitrogen) gel electrophoresis. Gels were stained with Gel Code Blue staining solution (Pierce) and distained with water. Under reducing conditions, DS-Cavi appeared as two bands on the gel, representing the cleaved $F_1$ and $F_2$ fragments, as expected. Under non-reducing conditions, DS-Cav1 appeared primarily as a band near 50 kDa, representing one cleaved $F_1$ fragment and one $F_2$ fragment held together by native disulfide bonds. As expected, single chain RSV mutant LZF57 appeared primarily as an uncleaved monomeric $F_0$ band on the gel, under either condition. The change in mobility for LZF57 under reducing and non-reducing conditions is most likely caused by a loss of compactness under reducing conditions, leading to an increased apparent molecular weight. Single chain RSV mutant LZF111 also appeared primarily as an uncleaved monomeric FO band on the gel, under reducing conditions. Under non-reducing conditions, although there are two subdominant lower bands at 50 kDa and 100 kDa consistent with monomeric and dimeric forms, the dominant band for LZF111 is shifted up near 150 kDa, consistent with the molecular weight of a trimer. As the D486C/D489C mutations were the only difference between the LZF57 and LZF111 constructs, this data suggested that the designed inter-molecular disulfide bond indeed forms in the majority of LZF111 molecules.

Example 3

LZF111 Stability Studies

Figure 5A:
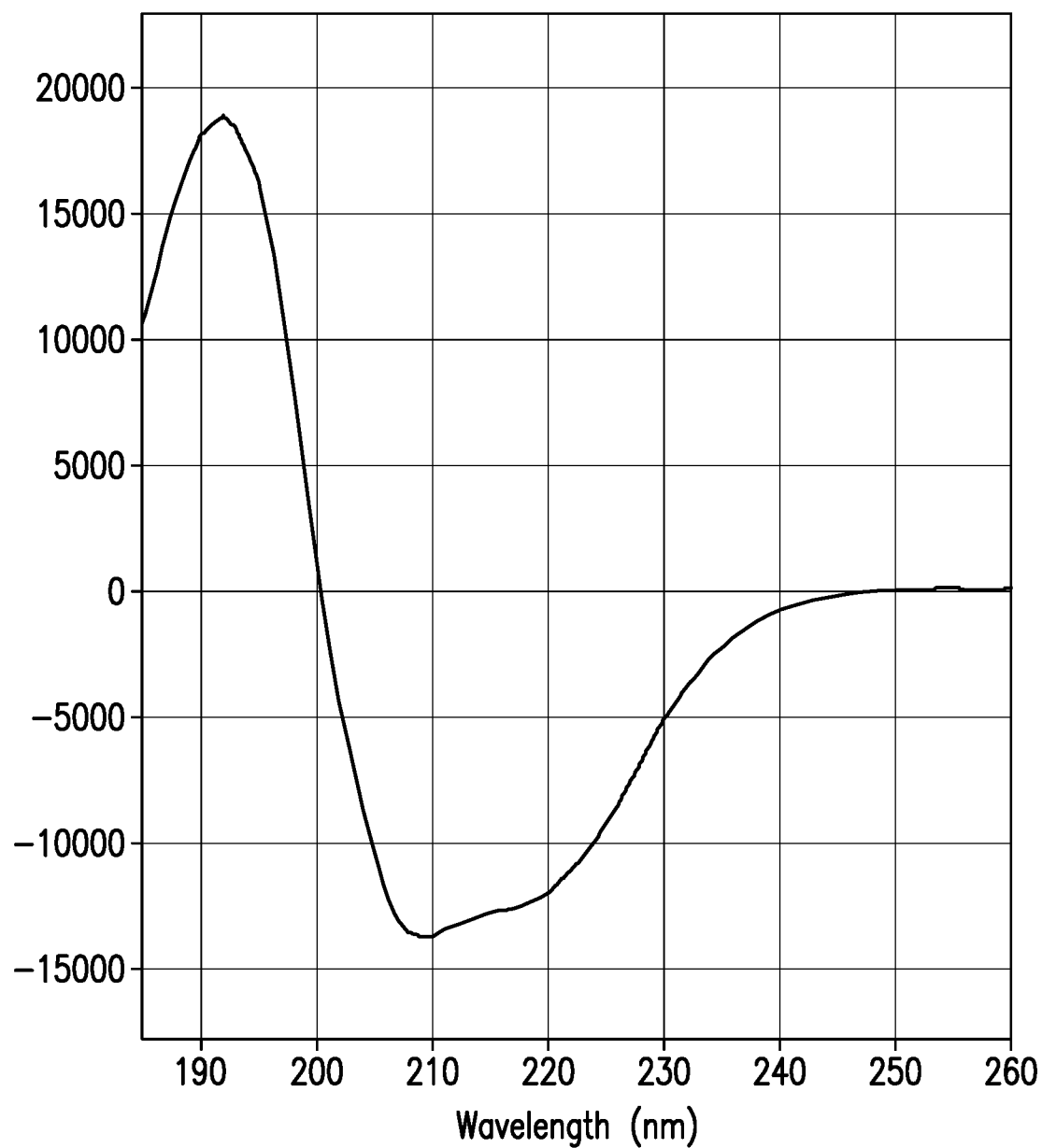
Figure 5B:
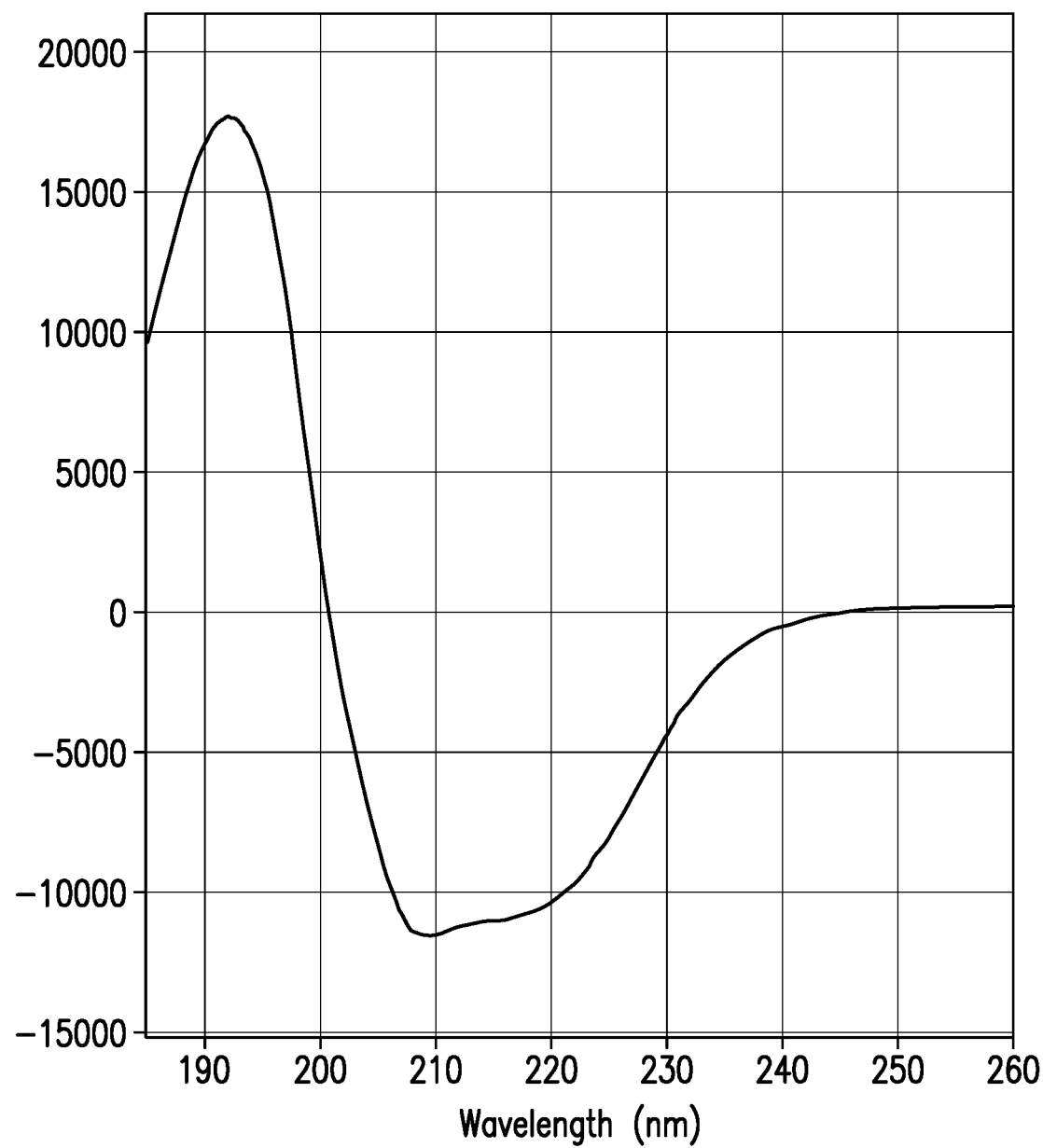
Figure 6:
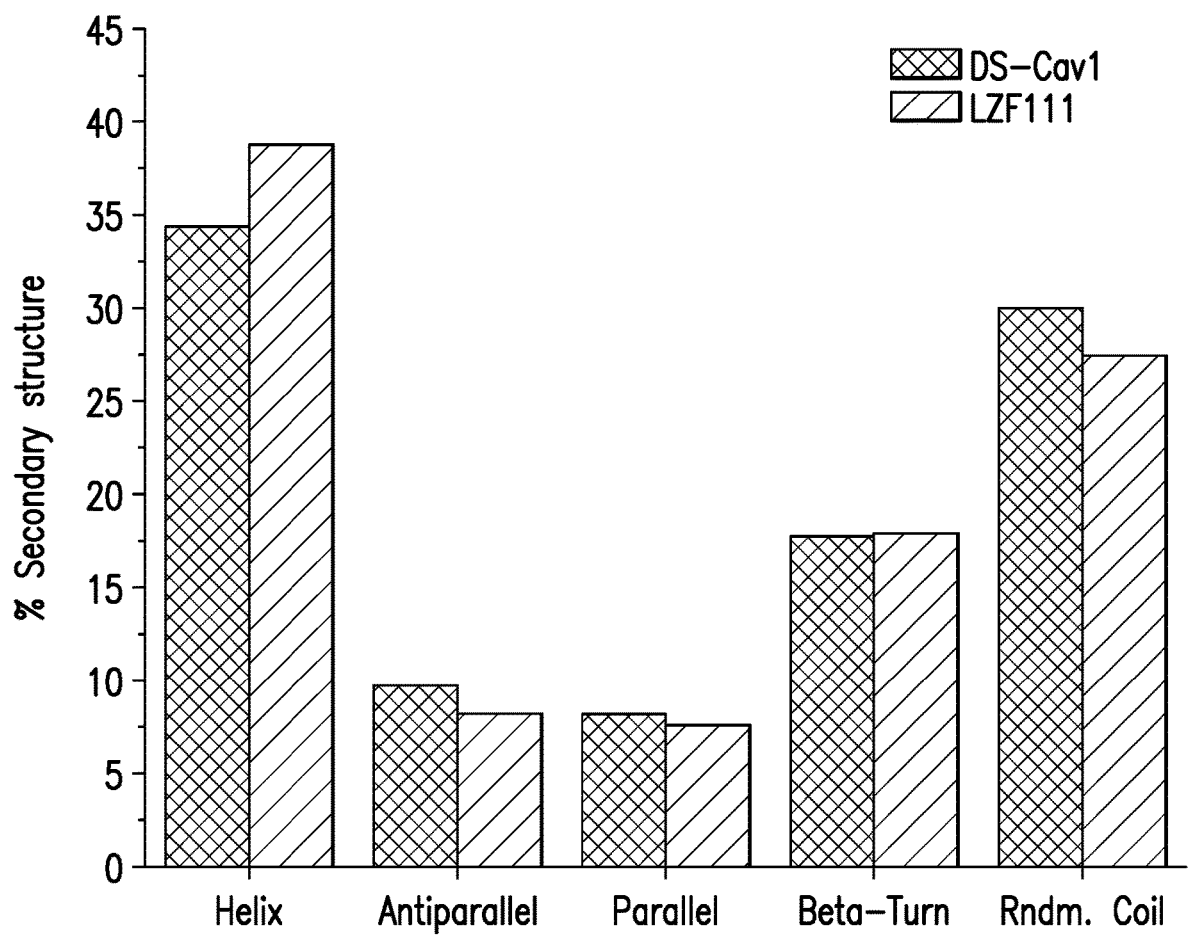

To analyze the secondary structures of purified RSV F proteins, circular dichroism ("CD") spectra were acquired on a Chirascan spectrometer (Applied Photophysics LtD, UK). Samples were analyzed after buffer exchange into 10 mM $Na_2HPO_4$ using Zeba spin columns (Pierce) and subsequent 1:2 dilution into 10 mM $Na_2HPO4$ yielding a final protein concentration of 3.9 µM and 4.4 µM for DsCav-1 and LZF111, respectively. CD spectra were recorded in undiluted using a quartz cuvette with 0.5 mm path length. The temperature control was set to 20° C. The bandwidth was set to 1 nm. Data points between 185 nm and 260 nm were acquired in 1 nm intervals with 5 s sampling time per time point. Sample and buffer spectra were acquired after 10 minutes of temperature equilibration applying three technical replicates, respectively. Average buffer spectra were subtracted from sample spectra. Resulting data points were smoothed with the Savitzky-Golay algorithm (polynomial order 2, two data points to left and right) using the Origin Pro 7.5 SR7 software package (Origin Lab Corporation). The CD spectra of DS-Cav1 and LZF 111 were almost identical (FIGS. 5A and 5B). Secondary structures were further analyzed by reconstruction of the CD spectra (185 nm to 260 nm) using a neural network that was trained on CD spectra of proteins with resolved 3D structure (software CDNN: Circular Dichroism Neuronal Network) (FIG. 6), indicating that the modifications of LZF111 did not lead to significant changes in secondary structures of the prefusion F protein.

Figure 7:
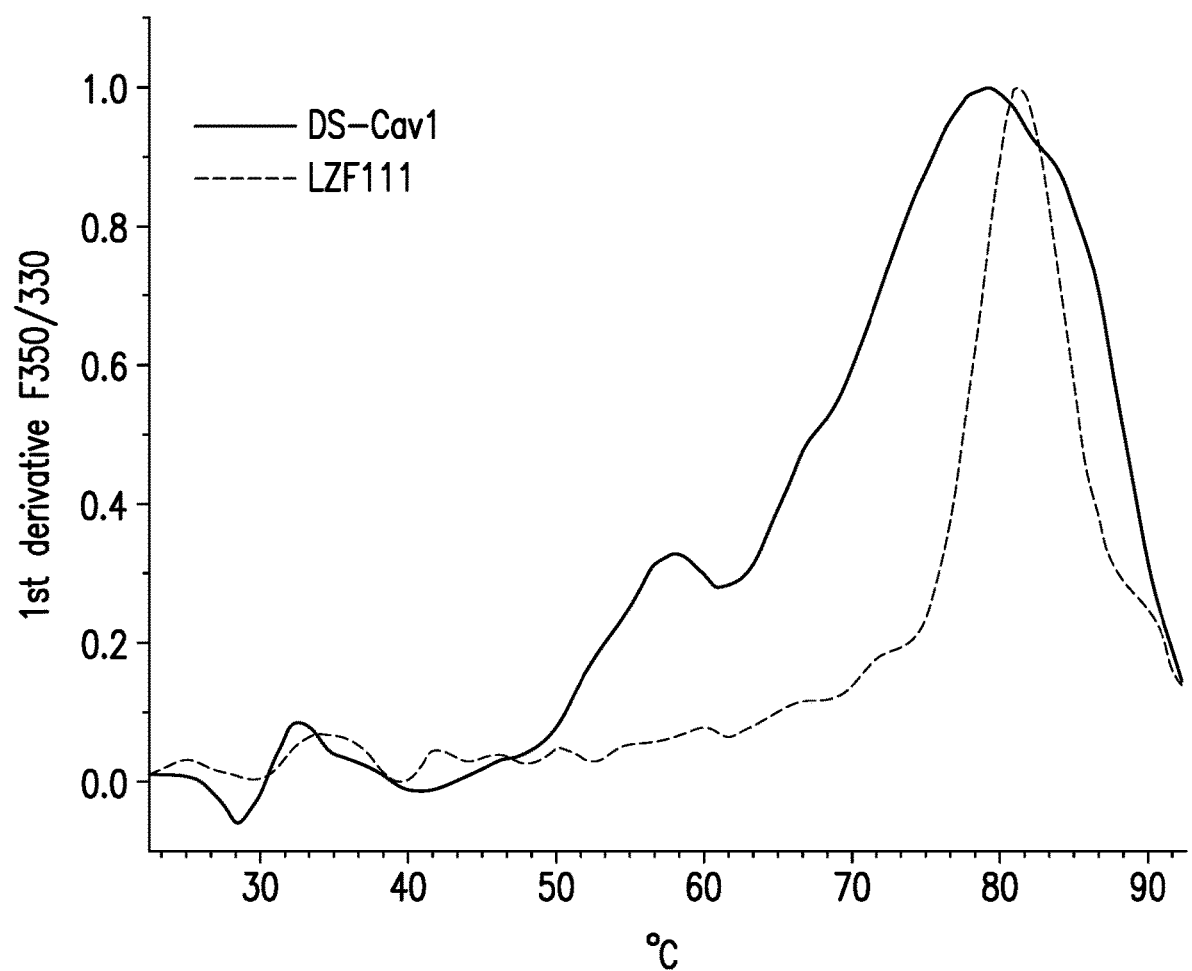

Differential scanning fluorimetry (DSF) analyses were performed with DS-Cav1 and LZF111 proteins to evaluate their stability. Solutions of DS-Cav1 protein (0.27-35 µM) in 50 mM HEPES, 300 mM NaCl at pH 7.5 were prepared by serial dilution. The fluorescence signal of each 85 µL protein sample in a micro quartz cuvette with an optical path length of 3 mm×3 mm (Thermo Fisher) was detected using a Cary Eclipse fluorimeter equipped with a Cary temperature controller (Agilent Technologies, Calif.). The intrinsic protein fluorescence was recorded at 330 nm and 350 nm. The excitation wavelength was set to 280 nm with a slit width of 10 nm. The emission slit width was set to 2.5 nm. The photo multiplier voltage was adjusted before each measurement to values between 500V and 800V to maximize the fluorescence signal. Thermal unfolding experiments were performed using a temperature ramp of 1° C./min from 20° C. to 95° C. in 0.5° C. increments. The sample was equilibrated at the starting temperature for 1 min and fluorescence signals were averaged for each data point for 1.5 s. A multi-cell holder allowed analysis of up to 4 samples simultaneously. Raw data was exported for further processing with Origin Pro®7.5 SR7 to obtain melting curves of fluorescence intensity as a function of temperature. The melting curves were smoothed (polynomial order=1, number of points=12), and peak centers of the first derivative of the ratio between 350 nm and 330 nm were used as melting temperatures (Tm). Data was normalized by the highest signal intensity in order to aid the comparison of different protein samples or protein concentrations. DS-Cav1 has two transition midpoints (60.85±1.98° C. and 80.7±0.93° C.), which were presented as the mean obtained from all protein concentrations analyzed for the same sample type (Flynn et al. 2016) (FIG. 7). For LZF111, the Tm presented (~81° C.) was obtained from a single concentration of 15 µM (FIG. 7). The absence of the lower Tm at 60.85° C. and the narrower peak for the higher Tm at ~81° C. suggested that LZF111 has improved stability compared to DS-Cav1.

Figure 8A:
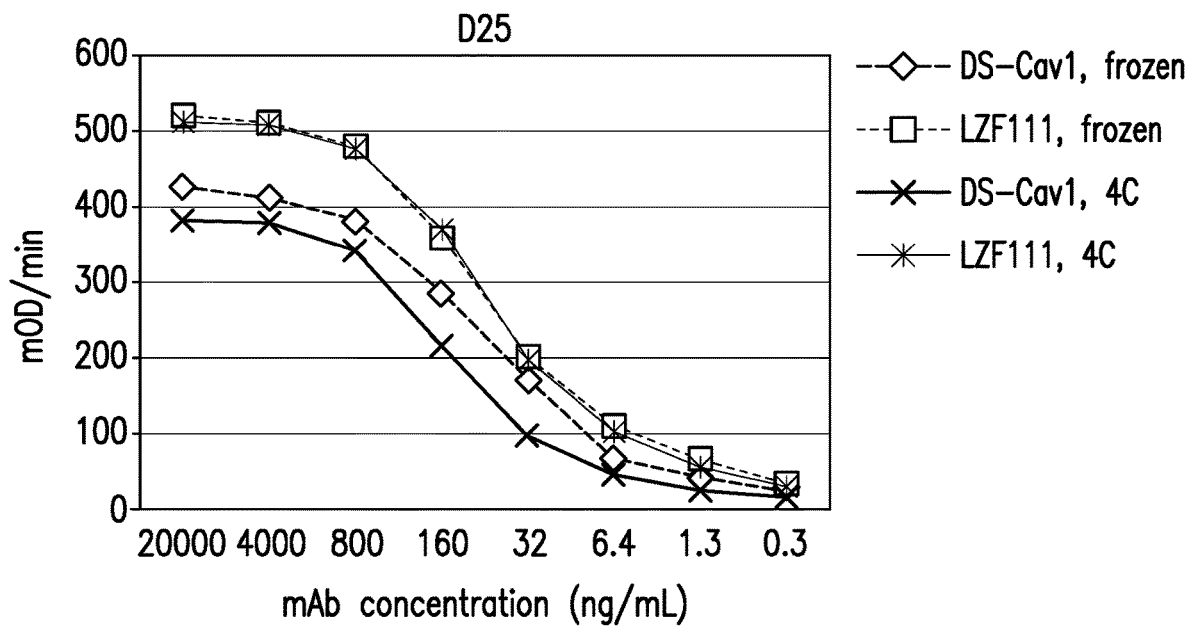
Figure 8B:
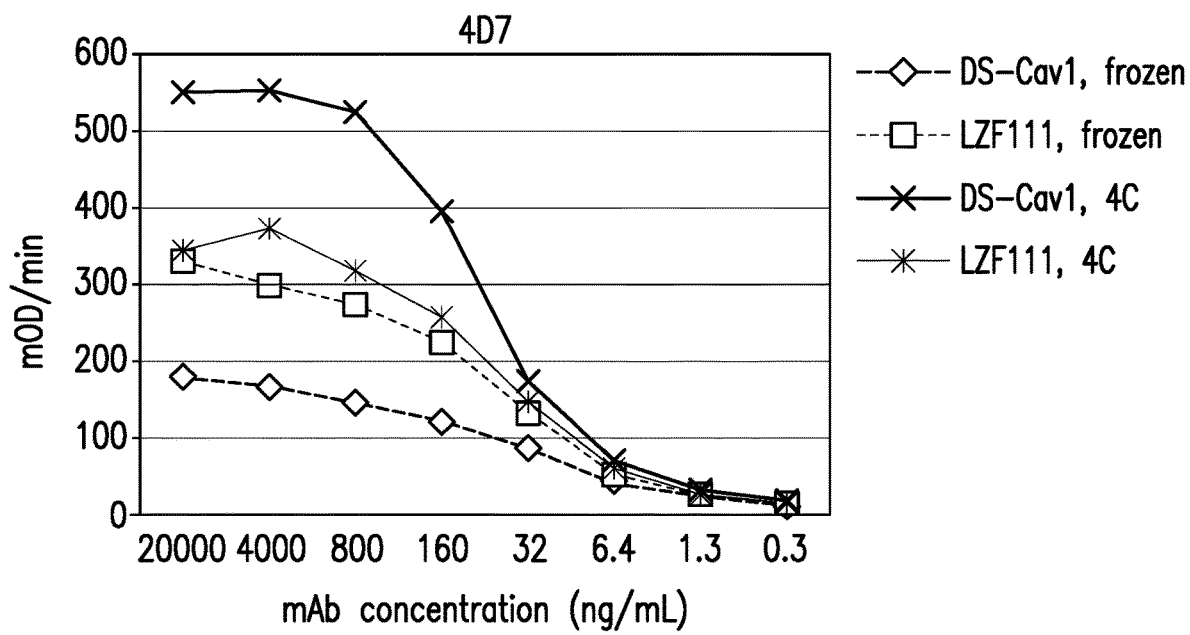
Figure 8C:
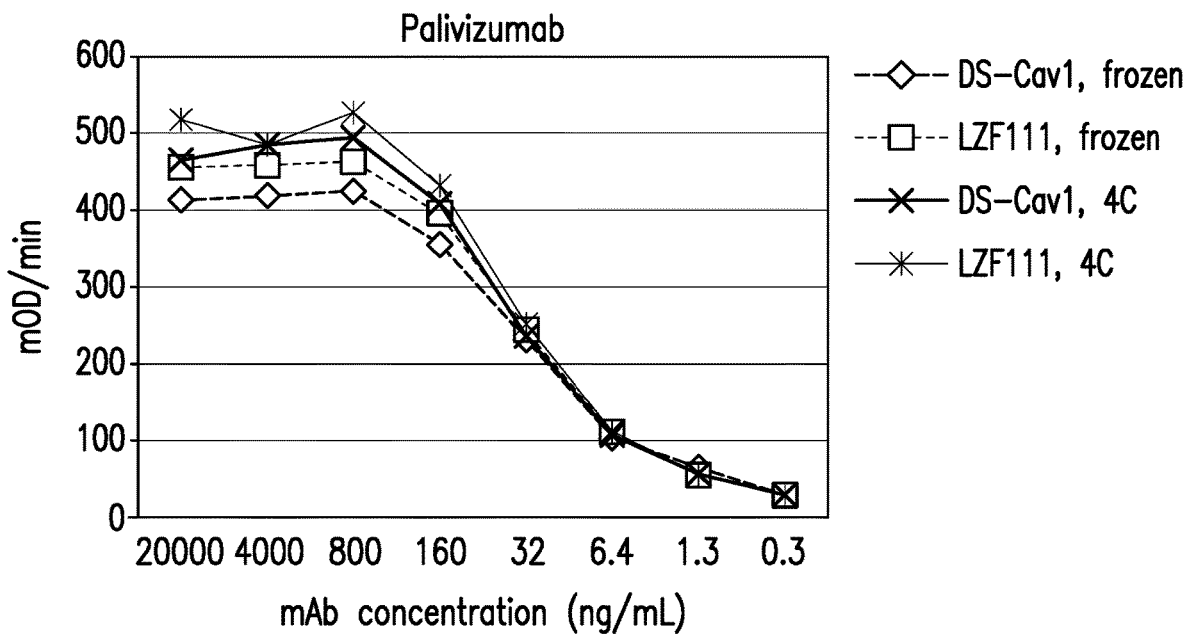
Figure 8D:
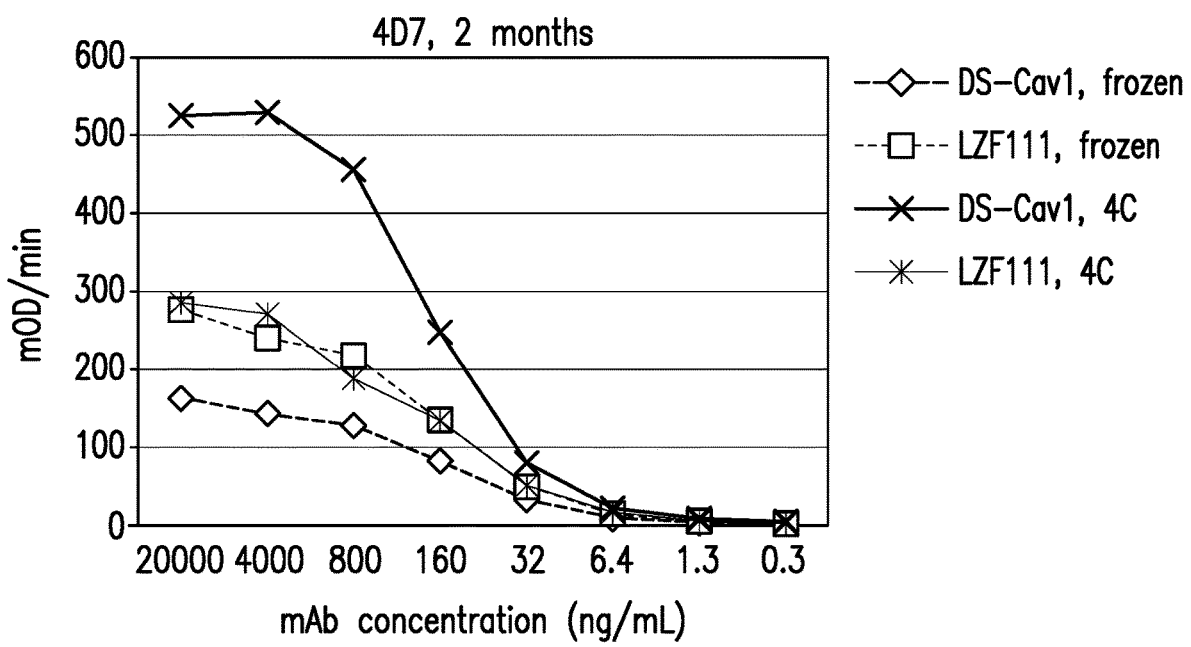
Figure 8E:
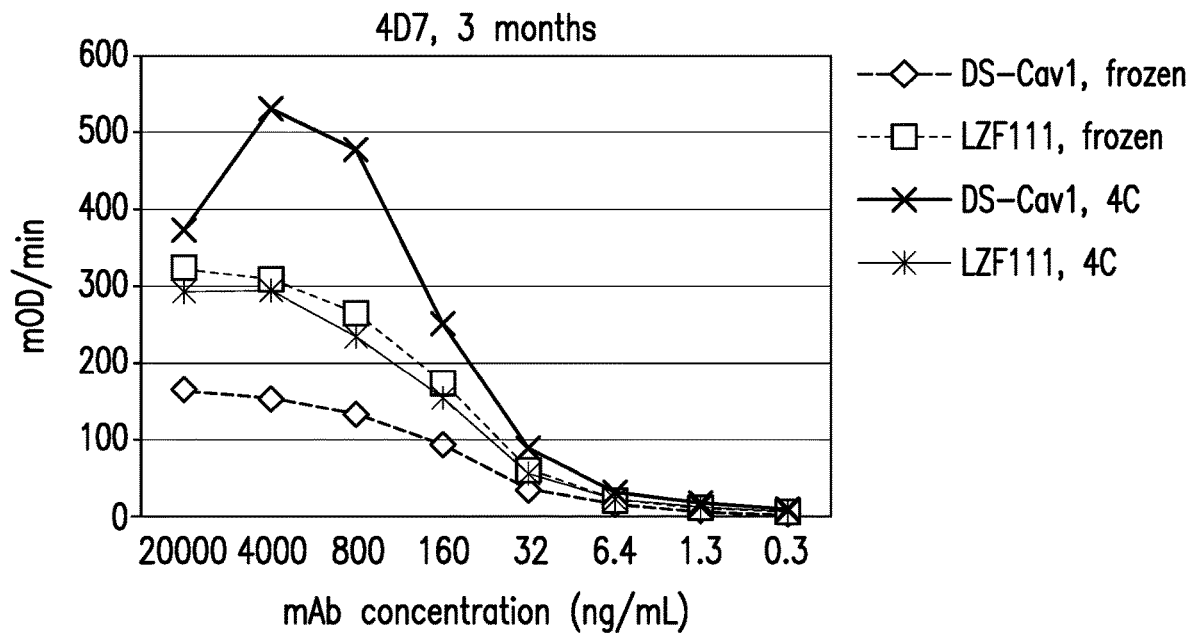

Long-term stability at 4° C. or higher is a desirable attribute for a subunit vaccine antigen. To assess the long term stability of DS-Cav1, we have previously used antibody binding assays with D25 and 4D7, as well as biophysical analyses. Our data demonstrated that upon long-term storage at 4° C., DS-Cav1 undergoes a conformational change, adopting alternate structures that gain the ability to bind 4D7 (Flynn et al. 2016). To evaluate the long-term stability of LZF111, purified DS-Cav1 protein or construct LZF111 was stored frozen or at 4° C. for 1, 2, or 3 months, and evaluated with D25, 4D7 and palivizumab in an ELISA binding assay. Briefly, purified proteins were diluted to 1 µg/mL with PBS and coated on 96-well ELISA plate (NUNC) overnight at 4° C. Unbound sites were blocked by addition of 2% (v/v) bovine serum albumin (BSA) in PBS and incubation for 1 hour at room temperature. Plates were washed with PBS containing 0.05% (v/v) Tween® 20 (polysorbate 20) (PBS-T) and incubated with serial dilutions of antibodies (D25 or palivizumab) at room temperature for 1 hour. Plates were washed again with PBS-T and incubated for 1 hour at room temperature with goat anti-human (for D25 and palivizumab) or anti-mouse (for 4D7) IgG HRP-conjugated secondary antibody (Thermo Fisher) diluted 1:2,000. Following an additional wash with PBS-T and brief rinse with dd$H_2O$, Super AquaBlue ELISA substrate (eBiosience) was added, and the plate was immediately read at 405 nm for 5 min. mOD/min was calculated for each well. FIGS. 8A, 8B and 8C show that after 1 month storage at 4° C., while D25 and palivizumab relativities were maintained for both constructs, a significant increase in 4D7 binding was detected with DS-Cav1, but not with the improved LZF111. Furthermore, no increased 4D7 binding was observed with LZF111 after 2 and 3 months storage at 4° C. (FIGS. 8D and 8E), suggesting that long term stability of LZF111 is superior to DS-Cavi.

Example 4

Immunogenicity Studies

Figure 9A:
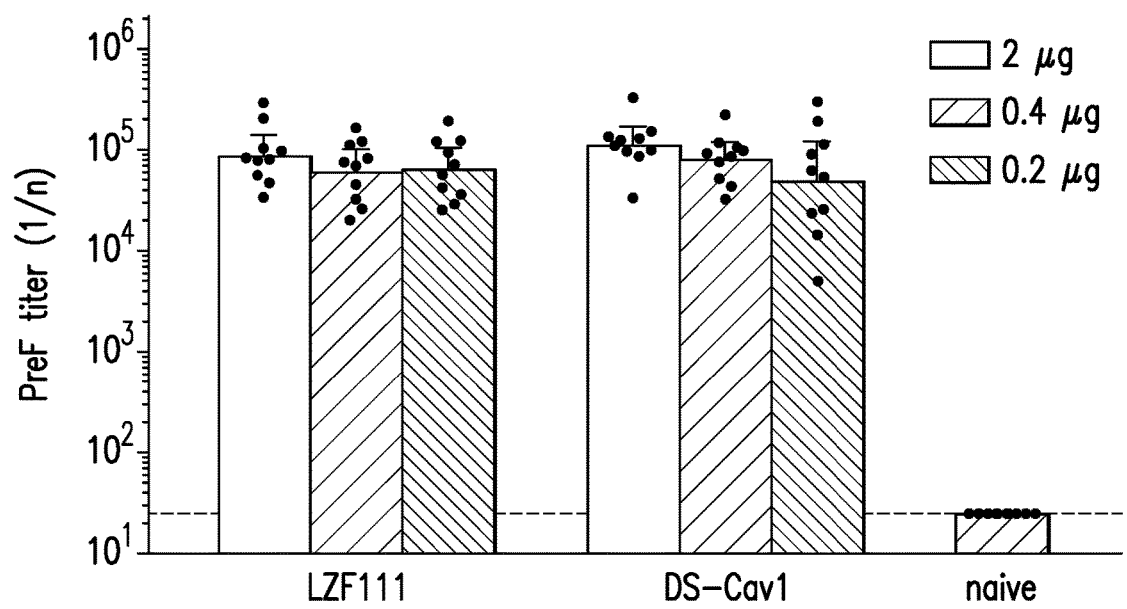

A mouse immunogenicity study was designed to compare the immunogenicity of DS-Cav1 and LZF111 subunit vaccines. Animals tested were female BALB/c mice obtained from Charles River Laboratories. 10 mice per group were immunized twice with three different doses (2 µg, 0.4 µg and 0.2 µg) of either purified DS-Cav1 or LZF 111a proteins with aluminum adjuvants at weeks 0 and 3. Bleeds were collected 2 weeks after each immunization and sera were analyzed. To assess binding antibody titers against prefusion F protein, immulonl2HB microtiter plates (NUNC) were coated with 2 µg/mL purified recombinant RSV F protein DS-Cavi, and incubated at 4° C. overnight. The plates were then washed and blocked for 1 hour with PBS-T containing 3% non-fat milk (blocking buffer) at room temperature. Test samples were serially diluted 4-fold in blocking buffer (starting at 1:50 dilution), transferred to the RSV F coated plates, and incubated for 2 hours at room temperature. Following three washes with PBS-T, HRP conjugated anti-mouse IgG secondary antibody (Invitrogen) diluted 1:3,000 in blocking buffer was added to the plates and incubated for an additional 1 hour. Plates were washed again and developed with SuperBlu Turbo TMB (Virolabs) in the dark. The reaction was stopped after 5 minutes and absorbance was read at 450 nm on a VersaMax ELISA microplate reader (Molecular Devices). ED10 ELISA titers, which indicated the effective dilution of the serum sample that gives 10% of the maximum signal, were determined by four parameter curve fit in GraphPad Prism 7 software. FIG. 9A shows the ED10 ELISA titers against prefusion F protein of post dose 2 sera. The bottom horizontal dashed line indicates limit of detection. Data showed that LZF111 induced similar anti-prefusion F antibody levels compared to DS-Cavi across different doses.

Neutralization assay was also performed on mouse sera that were treated at 56° C. for 30 min to inactivate complement prior to testing. Two-fold serial dilutions of serum samples were prepared in EMEM containing 2% FBS starting at 1:4 dilution. Diluted serum was added in duplicate to 96-well plates and mixed with RSV Long strain (100 pfu/mL) in 100 pl total volume. The mixture of virus and serum samples was incubated for 1 hour at 37° C. with 5% $CO_2$. Following incubation, Hep-2 cells at a concentration of 1.5 x $10^4$ cells per well were added. The plates were incubated for 3 days at 37° C. with 5% $CO_2$. The cells were then washed and fixed with 80% acetone for 15 minutes. RSV infected cells were then immunostained. Briefly, RSV F- and N-specific monoclonal antibodies were added to the test plates with fixed cells and incubated for 1 hour at room temperature. After washing, biotinylated goat anti-mouse IgG was added and incubated for 1 hour. The plates were washed again and developed by a dual channel near infrared detection (NID) system.

Figure 9B:
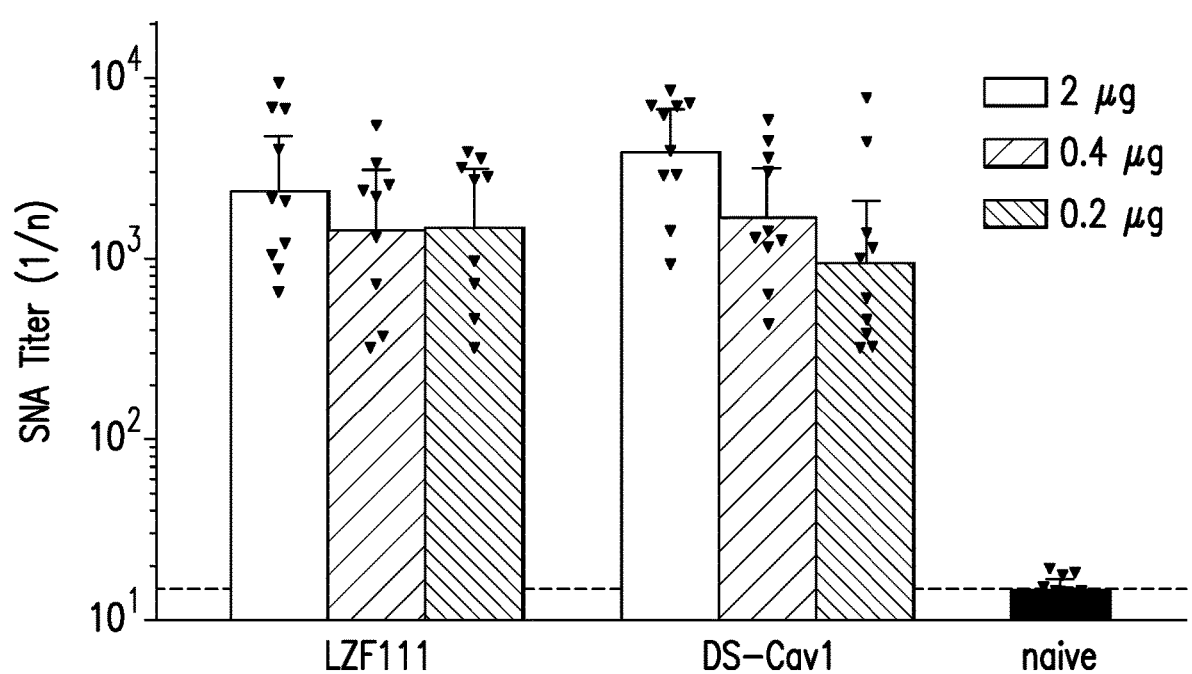

Infrared dye-Streptavidin to detect RSV specific signal and two cell stains for assay normalization were added to the 96-well plates and incubated for 1 hour in the dark. Plates were washed, dried in the dark for 20 minutes, and read on the Licor Aerius 1 Automated Imaging System utilizing a 700 channel laser for cell normalization and an 800 channel laser for detection of RSV specific signal. The 800/700 ratios were calculated and serum neutralizing titers (IC50) were determined by four parameter curve fit in GraphPad Prism 7 software. Serum neutralization titers of PD2 sera against RSV Long strain were shown in FIG. 9B. The bottom horizontal dashed line indicates limit of detection. Data showed that LZF111 induced similar levels of neutralizing antibodies compared to DS-Cav1 across different doses.

Example 5

Cotton Rat Immunogenicity Study

In this example, assays were carried out to test the immunogenicity and efficacy of mRNA/LNP vaccines in the cotton rat RSV challenge model. More specifically, female Sigmodon hispidus cotton rats were used and immunizations began at 6-7 weeks of age. The mRNA vaccines used were generated and formulated in lipid nanoparticles. The mRNA vaccines evaluated in this study included:
  MRK-04 membrane-bound DS-Cav1 (stabilized prefusion F protein)
  MRK-04_nopolyA_3mut membrane-bound DS-Cav1 (stabilized prefusion F protein)
  mVRC-1 (v2) membrane-bound single chain sc9 mDS-Cav1, A149C, Y458C (stabilized prefusion F protein)
  mLZF-111 membrane-bound single chain mDS-Cav1, D486C, D489C (stabilized prefusion F protein)

Groups of 8 cotton rats were immunized intramuscularly with 100 4 of vaccine, delivered with 50 4 injections into each quadriceps. The groups were vaccinated with the following vaccines:

| Group | Vaccine | Conc (µg/ml) | Dose (µg) |
| --- | --- | --- | --- |
| 1 | None | NA | NA |
| 2 | MRK-04, I.M. | 250 | 25 |
| 3 | MRK-04_nopolyA_3mut, I.M. | 250 | 25 |
| 4 | MRK-04_nopolyA_3mut, I.M. | 50 | 5 |
| 5 | MRK-04_nopolyA_3mut, I.M. | 10 | 1 |
| 6 | mVRC-1 (v2), I.M. | 250 | 25 |
| 7 | mVRC-1 (v2), I.M. | 50 | 5 |
| 8 | mVRC-1 (v2), I.M. | 10 | 1 |
| 9 | mLZF-111, I.M. | 250 | 25 |
| 10 | mLZF-111, I.M. | 50 | 5 |
| 11 | mLZF-111, I.M. | 10 | 1 |

The animals were immunized on day 0 and day 28 of the experiment. On days 28 and 56, blood was drawn from each animal and used for serological assays. On day 56, the cotton rats were challenged intranasally with $1 \times 10^{5.5}$ PFU RSV A2. Four days post inoculation, animals were sacrificed by $CO_2$ inhalation and lung (left lobes) and nasal turbinates were removed and homogenized in 10 volumes of Hanks Balanced Salt Solution (Lonza) containing SPG on wet ice. The samples were clarified by centrifugation at 2000 rpm for 10 minutes, aliquoted, flash frozen, and immediately stored frozen at −70° C.

RSV Neutralization Assay:

Cotton rat sera from each animal was evaluated for neutralization of RSV-A (Long strain) using the following procedures:
1. All sera samples were heat inactivated by placing in dry bath incubator set at 56° C. for 30 minutes. Samples and control sera were then diluted 1:3 in virus diluent (2% FBS in EMEM) and duplicate samples were added to an assay plate and serially diluted.
2. RSV-Long stock virus was removed from the freezer and quickly thawed in 37° C. water bath. Viruses were diluted to 2000 pfu/mL in virus diluent
3. 50 µL of diluted virus was added to each well of the 96-well plate, with the exception of one column of cells, which used as a "no-virus" control
4. HEp-2 cells were trypsinized, washed, resuspended at $1.5 \times 10^5$ cells/ml in virus diluent, and 100 mL of the suspended cells were added to each well of the 96-well plate. The plates were then incubated for 72 hours at 37° C., 5% $CO_2$.
5. Following the 72 hour incubation, the cells were washed with PBS, and fixed using 80% acetone dissolved in PBS for 10-20 minutes at 16-24° C. The fixative was removed and the plates were allowed to air-dry.
6. Plates were then washed thoroughly with PBS+0.05% Tween. The detections monoclonal antibodies, 143-F3-1B8 and 34C9 were diluted to 2.5 □g/mL in assay diluent (1% BSA-PBS-0.1% Tween), and 50 µL of the diluted antibodies were added to each well of the 96-well plate. The plates were then incubated in a humid chamber at 16-24° C. for 60-75 minutes on rocker
7. Following the incubation, the plates were thoroughly washed.
8. Biotinylated horse anti-mouse IgG was diluted 1:200 in assay diluent and added to each well of the 96-well plate. Plates were incubated as above and washed.
9. A cocktail of IRDye 800CW Streptavidin (1:1000 final dilution), Sapphire 700 (1:1000 dilution) and 5 mM DRAQS solution (1:10,000 dilution) was prepared in assay diluent and 50 mL of the cocktail was added to each well of the 96-well plate. Plates were incubated as above in the dark, washed, and allowed to air dry.
10. Plates were then read using an Aerius Imager. Serum neutralizing titers were then calculated using a 4 parameter curve fit in Graphpad Prism.

Figure 11:
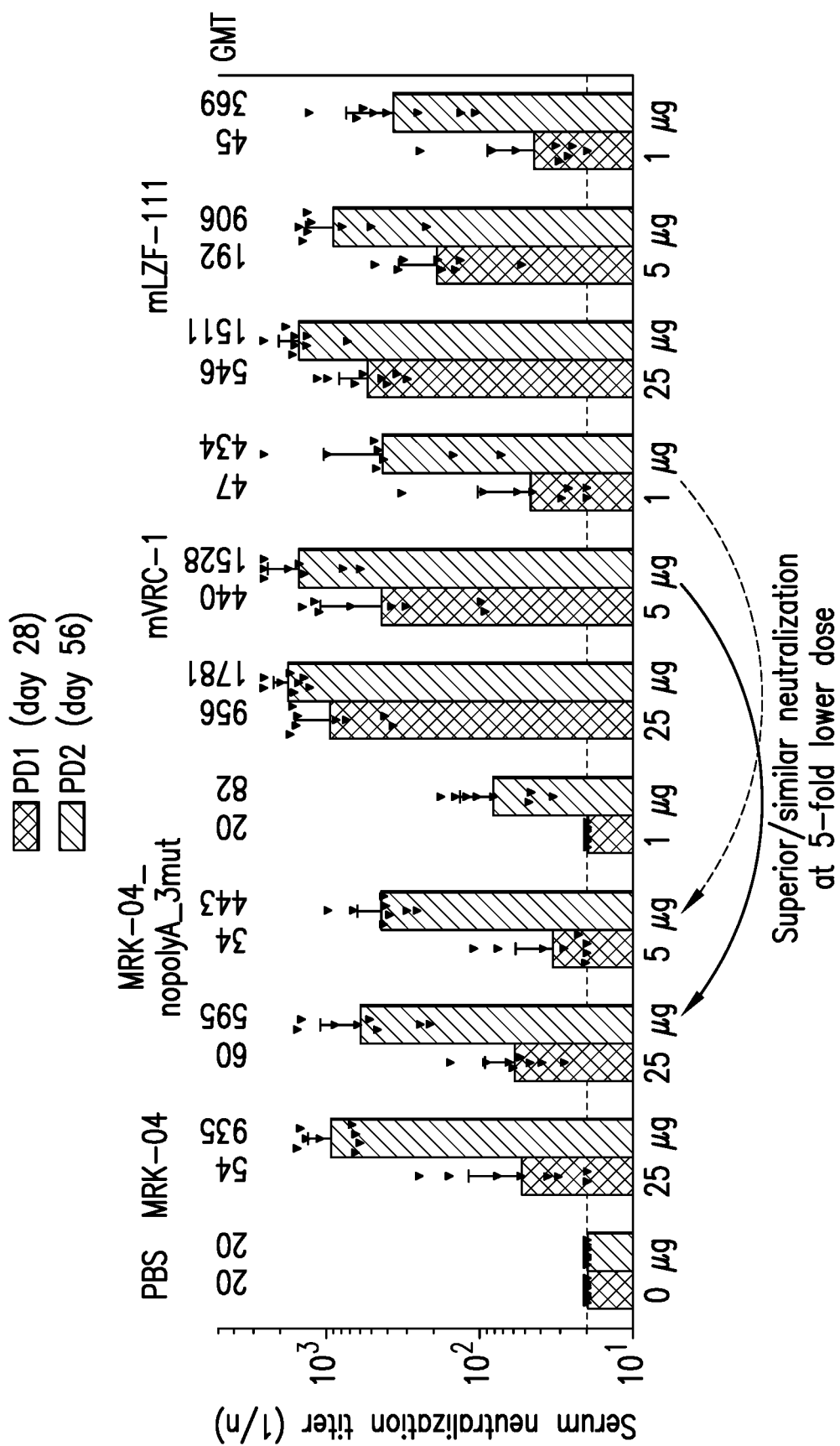

The titers determined post dose 1 (day 28) and post dose 2 (day 56) are shown in FIG. 11. It was found that the neutralizing titers were elicited in a dose dependent manner for all mRNA vaccines. All mRNA vaccines resulted in increased titers after a second dose regardless of the dose evaluated. Both mVRC-1 (v2) and mLZF111 induced higher titers then MRK-04 and MRK-04_nopolyA_3mut demonstrating superior or similar serum neutralizing titers at a 5-fold lower dose.

Competition alphaLISA

The immune response to specific epitopes on RSV F-protein for neutralizing antibodies was characterized. The antigenic site II is the binding site for palivizumab, a monoclonal antibody developed for the prevention of lower respiratory infection with RSV in at risk infants and toddlers. Antigenic site 0 is a binding site for more potent neutralizing antibodies that are elicited by natural infection with RSV. Additionally, we have generated an antibody (4D7) that targets site I, an epitope not presented in the prefusion conformation. Therefore, in contrast to D25, elicitation of 4D7-competing antibodies would suggest the in vivo generation of postF-like proteins. A competition alphaLISA was developed to characterize the antigenic site 0, antigenic site I and antigenic site II response to the various mRNA-based vaccines.

To measure competing antibody titers, 10 ul of samples serially diluted in HiBlock buffer (PerkinElmer) are placed in a 384 well alphaLISA plate. Diluted samples are mixed with 5 µl of AlphaLISA acceptor beads (100 ug/ml) that has been previously conjugated to a prefusion-stabilized RSV F protein (DS-Cav1) or a postfusion RSV F protein (RSV F wt).

After 30 min incubation at room temperature, 10 ul of biotinylated D25, palivizumab, or 4D7 antibody diluted in Hiblock buffer is added to every well. After additional 30 min incubation, 25 ul of streptavidin-donor beads (20 µg/ml) in HiBlock buffer is added to each well and incubated for 30 min in the dark. Plate is then read on an EnVision Alpha Reader (615 nm detection).

Figure 12:
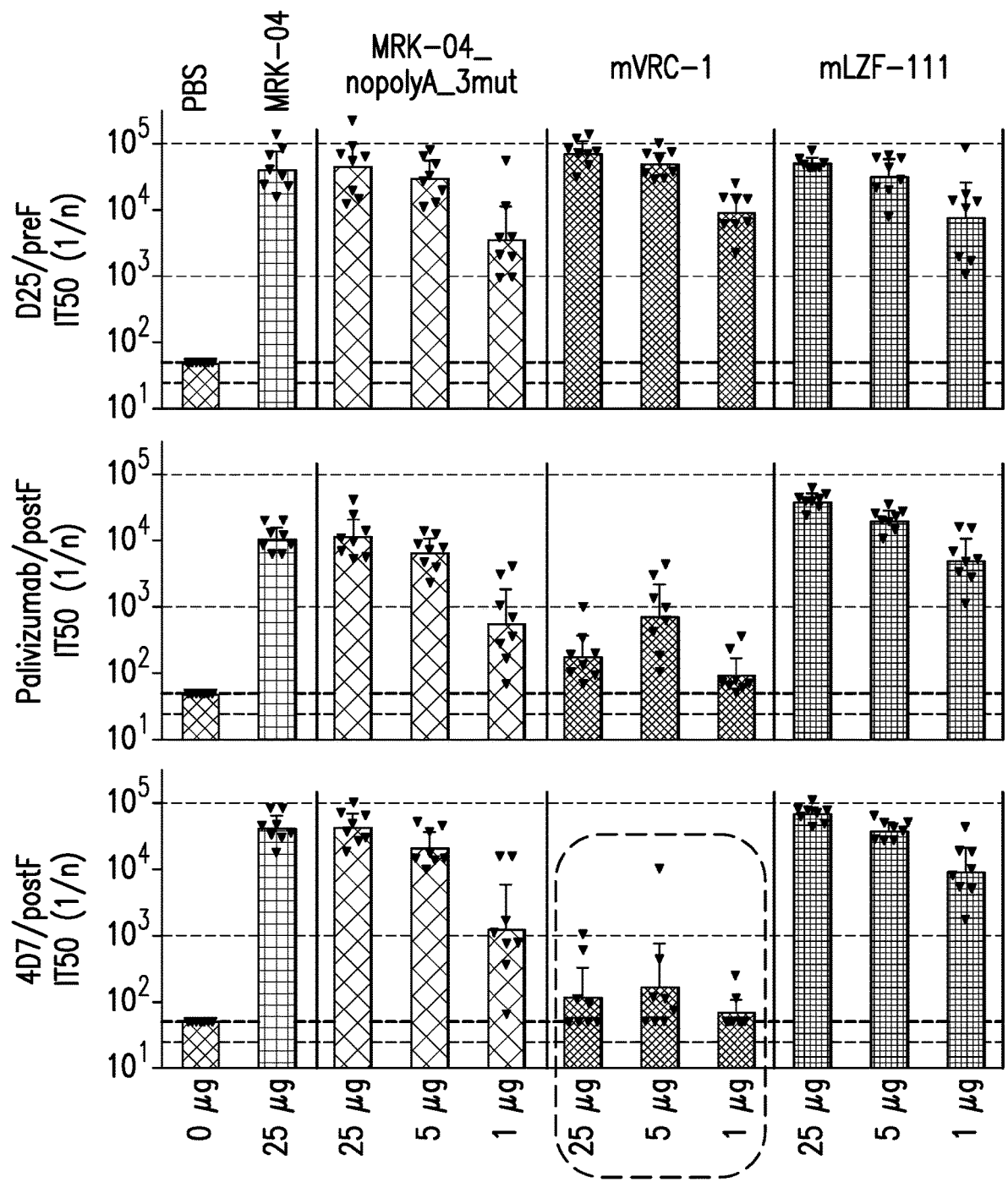

The palivizumab, D25, and 4D7 competing antibody titers measured on Day 56 (4 weeks PD2) are presented in FIG. 12. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein than MRK-04_nopolyA_3mut and mLZF-111.

C. Cotton Rat Challenge Results

Procedures for measuring RSV titers in the cotton rat lung and nose homogenates are described below. Lung and nose homogenates were clarified by centrifugation and diluted 1:10 and 1:100 in EMEM. Confluent HEp-2 monolayers were infected in duplicates with 50 µl per well starting with undiluted (neat) samples followed by diluted homogenates in 24-well plates. After one hour incubation at 37° C. in a 5% $CO_2$ incubator, wells were overlaid with 0.75% methylcellulose medium and plates restored into the 37° C. incubator. After 4 days of incubation the overlay was removed and the cells were fixed with 0.1% crystal violet stain for one hour, then rinsed, and air-dried. Plaques were counted and virus titers were expressed as plaque forming units per gram of tissue.

Figure 13:
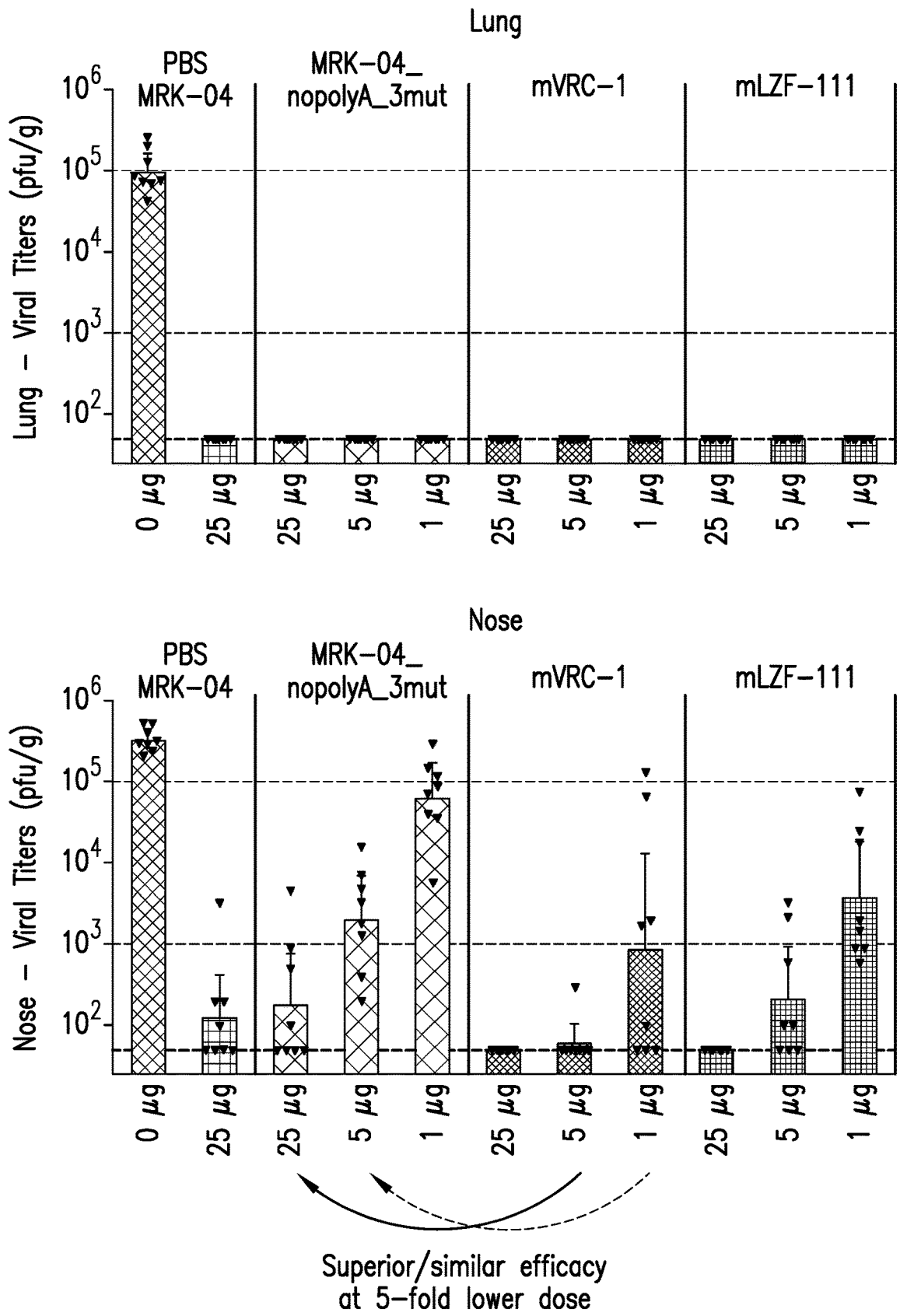
FIG. 13 sets forth RSV content in Lung and Nose after challenge of Cotton rats with RSV A.

To assess vaccine-mediated protection, viral titers were measured in lung and nose 5 days after challenge. All mRNA vaccines achieved total protection in the lung, but mVRC-1 (v2) and mLZF111 showed improved protection in the nose, demonstrating superior or similar efficacy to MRK-04 and MRK-04 nopolyA 3mut, at a 5-fold lower dose (FIG. 13).

Example 6

African Green Monkey Immunogenicity and Efficacy

In this example, assays were carried out to test the immunogenicity and efficacy of mRNA/LNP vaccines in the African Green Monkey RSV challenge model.

More specifically, male and female adult African Green Monkeys with body weights ranging from 1.6 to 2.65 kg, which were confirmed to be RSV-negative by neutralizing antibody titer, were used. The mRNA vaccines used were generated and formulated in lipid nanoparticles. The mRNA vaccines evaluated in this study included:

MRK-04_nopolyA_3mut membrane-bound DS-Cav1 (stabilized prefusion F protein)

mVRC-1 (v2) membrane-bound single chain sc9 mDS-Cav1, A149C, Y458C (stabilized prefusion F protein)

mLZF-111 membrane-bound single chain mDS-Cav1, D486C, D489C (stabilized prefusion F protein)

Groups of 4 African Green Monkeys were immunized intramuscularly with 500 µL of vaccine into one deltoid. The groups were vaccinated with the following vaccines as out in Table 1.

TABLE 1

Vaccine Formulations Tested for Immunogenicity in African Green Monkeys

| Group | Vaccine | Conc (µg/ml) | Dose (µg) |
|---|---|---|---|
| 1 | MRK-04_nopolyA_3mut, I.M. | 50 | 25 |
| 2 | MRK-04_nopolyA_3mut, I.M. | 10 | 5 |
| 3 | mVRC-1 (v2) | 50 | 25 |
| 4 | mVRC-1 (v2) | 10 | 5 |
| 5 | mLZF-111 | 50 | 25 |

TABLE 1-continued

Vaccine Formulations Tested for Immunogenicity in African Green Monkeys

| Group | Vaccine | Conc (μg/ml) | Dose (μg) |
|-------|---------|--------------|-----------|
| 6 | mLZF-111 | 10 | 5 |
| 7 | RSV A2 5.5log10pfu, I.N. | NA | NA |
| 8 | None | NA | NA |

The animals were immunized on day 0, day 28, and day 56 of the experiment. On days 0, 14, 28, 42, 56, and 70, blood was drawn from each animal and used for serological assays. On day 70, the African Green Monkeys were challenged intranasally with $1 \times 10^{5.5}$ PFU RSV A2. Nasopharyngeal swabs were collected on days 1-14 post challenge, and lung lavage samples were collected on days 3, 5, 7, 9, 12 and 14 post challenge to test for viral replication.

Figure 14:
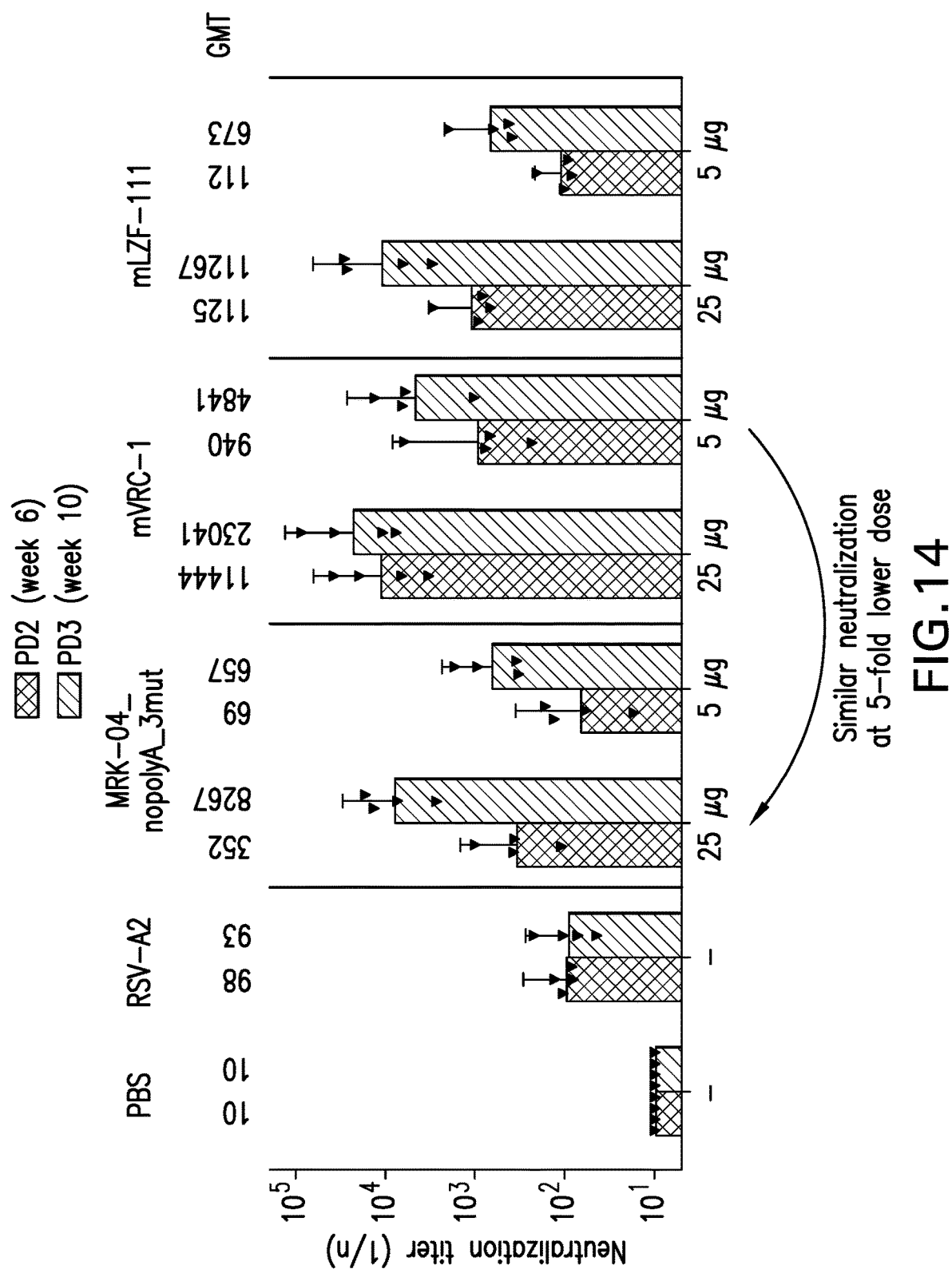
FIG. 14 sets forth serum neutralizing antibody titers ($NT_{50}$ Individual and GMT with 95% Confidence Intervals) to RSV A induced in African Green Monkeys by mRNA vaccines and control formulations.

A. RSV Neutralization Assay:

Monkey sera from each animal were evaluated for neutralization of RSV-A (Long strain) as described above. The $NT_{50}$ titers determined post dose 1 and post dose 2 are shown in FIG. 14. Titers were seen to increase after each dose all groups receiving mRNA vaccines. The GMTs obtained with mRNA vaccines at week 10 (2 weeks post-dose 3) were 1 to 2 orders of magnitude higher than in the animals that received RSV A2 depending on the dose and mRNA being tested. Serum samples from mVRC-1 (v2) immunized animals exhibited the highest neutralization titers, demonstrating a five-fold higher potency relative to MRK-04_nopolyA_3mut.

B. Competition ELISA

Competition ELISA titers were determined for palivizumab, D25 and 4D7 to characterize the antigenic site ϕ, antigenic site I and antigenic site II response to the various mRNA-based vaccines as described above.

Figure 15:
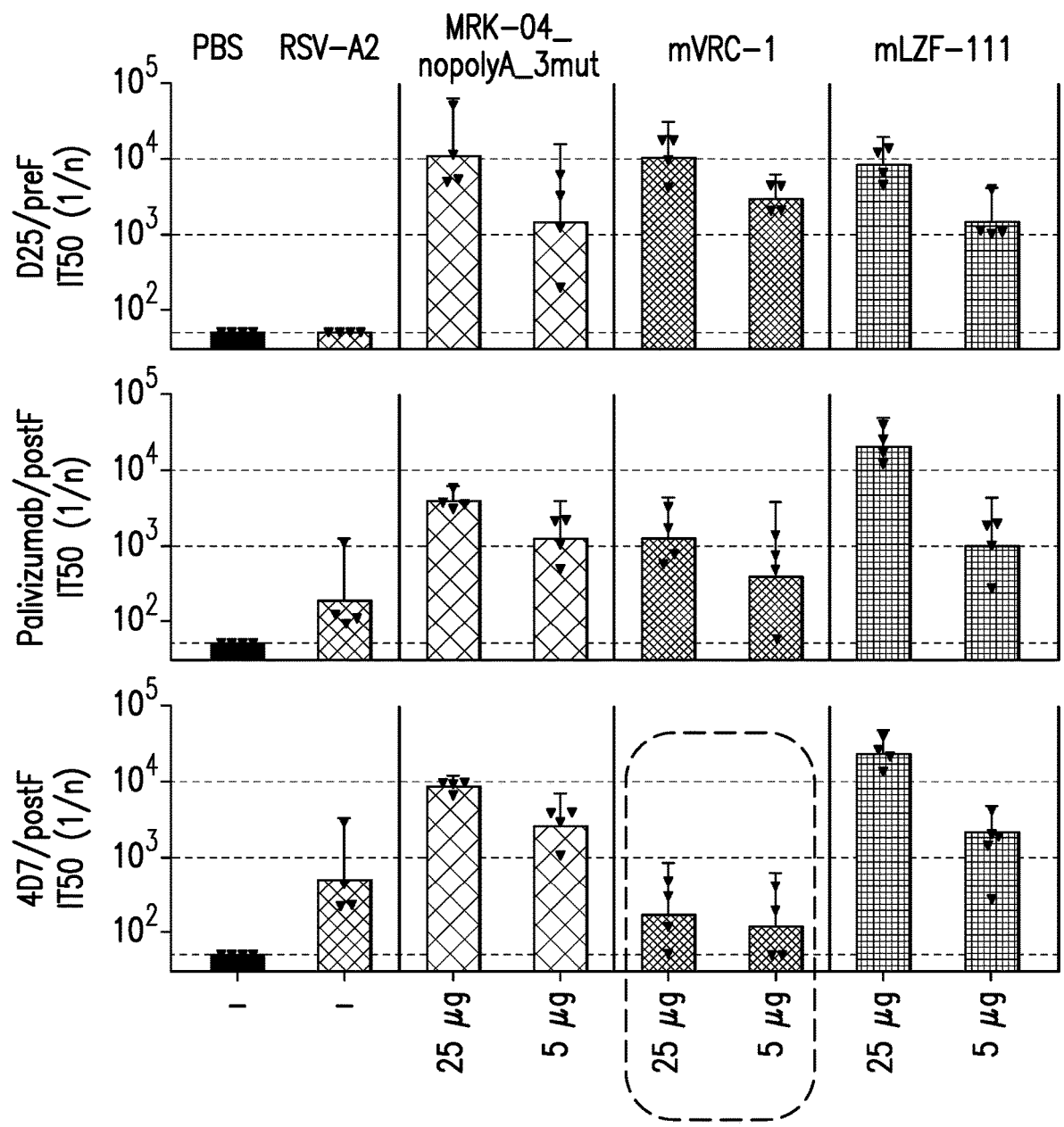
FIG. 15 sets forth serum antibody competition ELISA titers ($IT_{50}$ Individual and GMT with 95% Confidence intervals) against D25 (site 0), palivizumab (site II), and 4D7 (site I) measured at week 10 (2 weeks PD3).

The palivizumab, D25 and 4D7 competing antibody titers measured at week 10 (2 weeks PD3) are presented in FIG. 15. The competition data revealed that mVRC-1 (v2) induced lower levels of 4D7-postfusion F competing antibodies, while D25-prefusion titers and palivizumab titers are not affected. This different competition profile correlates with mVRC-1 (v2) mRNA expressing a more prefusion stabilized protein then MRK-04_nopolyA_3mut and mLZF-111.

C. African Green Monkey Challenge Results

As mentioned above, in order to evaluate vaccine efficacy African Green Monkeys were challenged intranasally with $1 \times 10^{5.5}$ PFU RSV A2 on day 70 post vaccination and nasopharyngeal swabs and lung lavage samples were collected post challenge to test for the presence of virus.

Figure 16A:
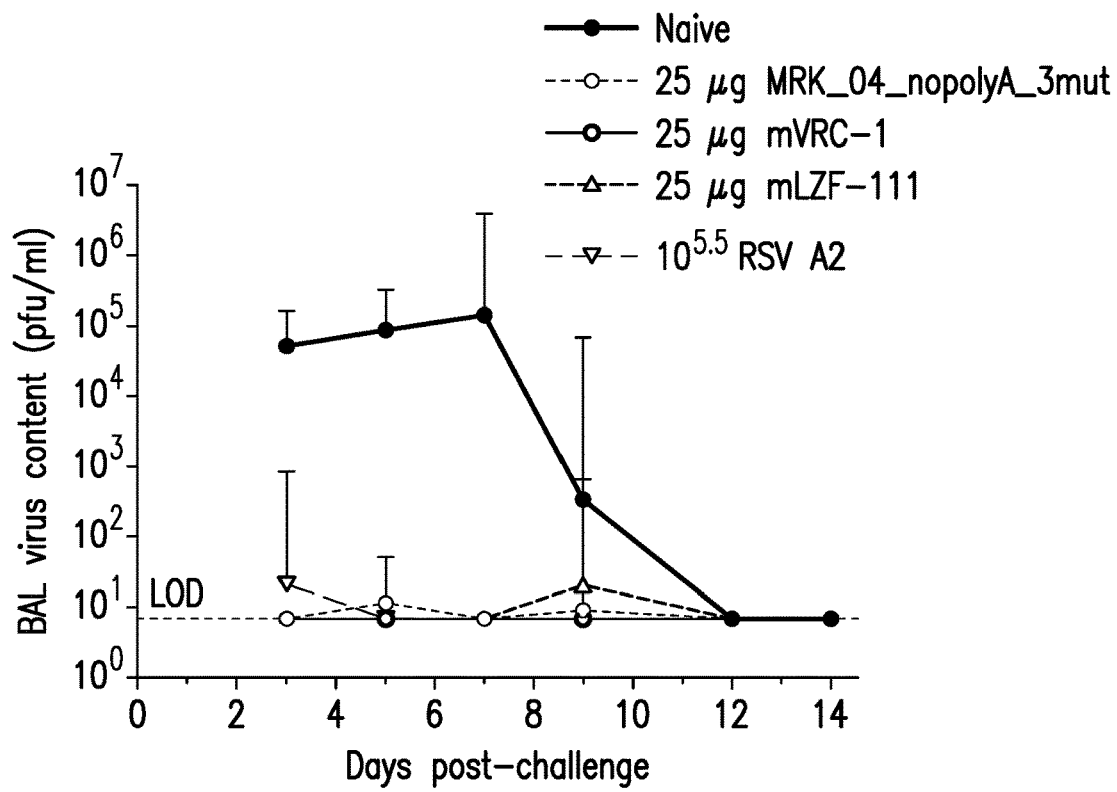
FIGS. 16A-16C sets forth RSV content in bronchoalveolar (BAL) fluid after challenge of AGMs.
Figure 16B:
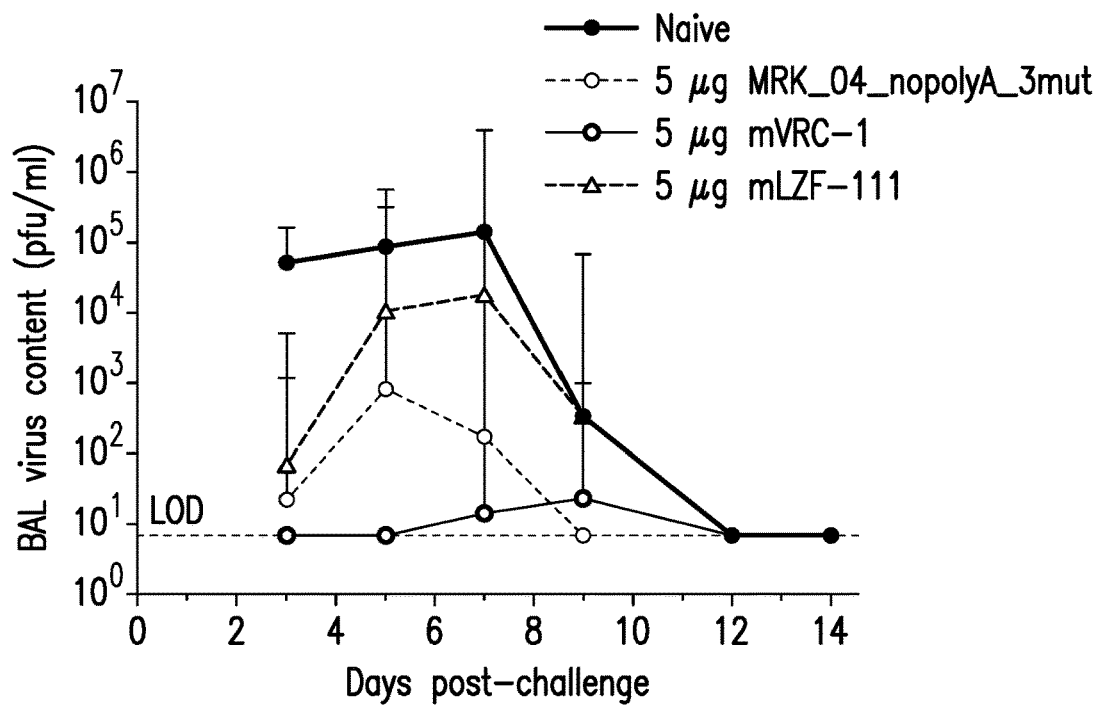
Figure 16C:
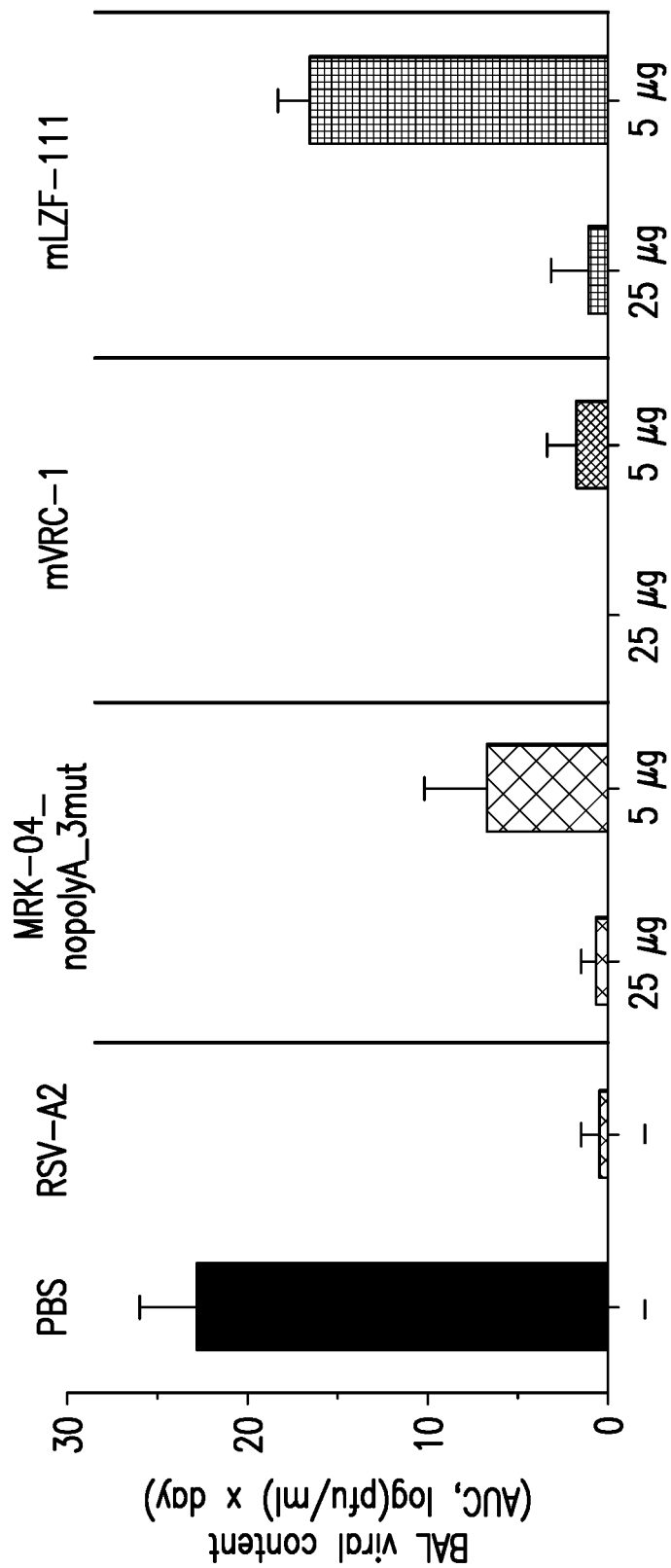

In order to measure RSV titers in the African Green Monkey lung lavage samples a viral plaque assay procedure for measuring viral titers was followed as outlined below. Briefly, samples were diluted and added in duplicate to 24-well plates containing confluent HEp-2 cell monolayers. The plates were incubated at 37° C. for one hour. Following the one hour incubation, sample inoculum was aspirated and 1 ml of overlay containing 0.75% methylcellulose was added. The plates were incubated at 37° C. for 5 days. Following the 5 day incubation, the cells were fixed and stained with crystal violet/ glutaraldehyde solution. Plaques were counted and titers were expressed as pfu/ml. Analysis of viral content in bronchoalveolar lavage (BAL) fluid (FIGS. 16A-16C) revealed that only mVRC-1 (v2) (25 μg) conferred total protection in the lung, and it afforded the best protection at a lower dose (5 μg).

In order to measure RSV titers in the African Green Monkey nasopharyngeal swabs an RSV RT-qPCR assay to detect RSV A was carried out as follows:

1) Equipment and Materials:
   A. Equipment
   1. Stratagene Mx3005P Real Time PCR system and MxPro Software
   2. Jouan GR422 centrifuge or equivalent
   3. Jouan Plate carriers or equivalent
   B. Reagents
   1. Quantitect® Probe Rt-PCR kit (1000) catalog #204445
   2. Water, Molecular Biology Grade DNAase-free and Protease free, 5 Prime, catalog #2900136
   3. TE buffer, 10 mM Tris 1 mM EDTA ph 8.0, Fisher Bioreagents, catalog #BP2473-100
   4. Viral primers: RSV A Forward and Reverse primers, Sigma custom, HPLC purified. Primer stocks are reconstituted to 100 uM in Molecular grade water and stored at −20° C.
   5. RSV dual labeled probe, Sigma custom, HPLC purified. Probe stocks are reconstituted to 100 uM in TE buffer and stored at −20° C. protected from light.
   6. RSV A standard were generated in-house and stored at −20° C. Standards for the assay were generated by designing primer pairs to the N gene of RSV A. The product length for the RSV A standard is 885 bp. QIAGEN OneStep RT-PCR was used to generate this standard.

| Primers | Sequences |
|---------|-----------|
| RSV A F N gene | 5' CTC AAT TTC CTC ACT TCT CCA GTG T (SEQ ID NO: 46) |
| RSV A R N gene | 5' CTT GAT TCC TCG GTG TAC CTC TGT (SEQ ID NO: 47) |
| RSV A FAM N gene | 5'FAM-TCC CAT TAT GCC TAG GCC AGC AGC A (BHQ1) (SEQ ID NO: 48) |

7. Promega, Maxwell® 16 Viral Total Nucleic Acid Purification Kit (Product #AS1150
   C. Supplies
   1. Stratagene Optical cap 8× strip, catalog #401425
   2. Stratagene Mx3000P 96 well plates, skirted, catalog #401334
   3. ART filtered pipet tips
2) RT-PCR Reactions and set up
   A. Preparation of Complete Master Mix
   1. Prepare complete Master Mix following the set up below for a final reaction volume of 50 μL. The following table is volume per well. Final primer concentration is 300 nM and final probe concentration is 200 nM.

| Reagent | μL |
|---------|-----|
| 2X Master Mix | 25 |
| RSV A F 100uM | 0.2 |
| RSV A R 100uM | 0.2 |
| RSV A FAM 100uM | 0.1 |
| RT enzyme mix | 0.5 |
| Water | 19 |

2. Add 45 µL of complete master mix to each well. Cover plate with plate cover and wrap in aluminum foil to protect from light.
B. Preparation of Standard curve
  1. Remove standard from −20° C.
  2. Dilute standards to final concentrations of 1e6 copy/5 µL to 1copy/5 µL using 10-fold dilutions.
C. Sample preparation
  1. Nasopharyngeal swab and lung lavage samples are prepared for the RT-PCR reaction using the Maxwell® 16 Viral Total Nucleic Acid Purification Kit (Promega, product #AS1150)
  2. 200 µL of sample is extracted following the manufactures protocol and eluted into 50 µL to be used in PCR reactions.
D. Additions of Samples
  1. Add 5 µL of extracted samples to appropriate wells. After addition of samples, carefully cap sample wells before adding standard curves.
  2. Add 5 µL of diluted standard to appropriate wells and cap.
  3. Add 5 µL of molecular grade water to No Template Control (NTC) wells.
  4. Wrap plates in aluminum foil and transfer plates to centrifuge.
  5. Spin plates for 2 mins at 100 rpm to pull down any samples or master mix that may be on the sides of well.
  6. Wrap plates in aluminum foil and transfer to Stratagene instrument.
E. Thermo cycler: Stratagene MX 3005P
  1. Place plates in Stratagene Mx3005P and set thermal profile conditions to:

| Step | Time | Temperature |
| --- | --- | --- |
| Reverse Transcription | 30 min | 50 |
| PCR intial activation step 2-step cycling: | 15 min | 95 |
| Denaturation | 16 sec | 94 |
| Combined annealing/extension | 60 sec | 62 |
| Number of cycles | 40 | |

2. Analyze results using the Stratagene Mx3005p software

Figure 17A:
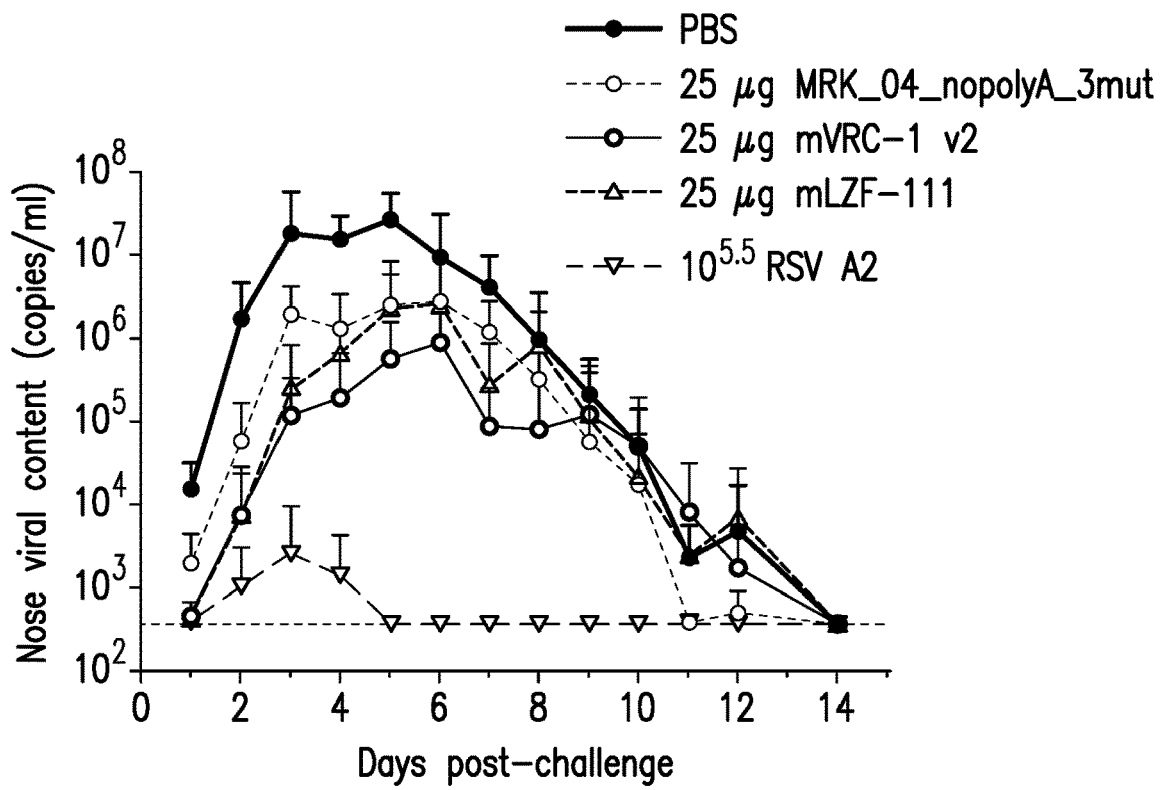
FIGS. 17A-17C sets forth the RSV content in nose swabs after challenge of AGMs.
Figure 17B:
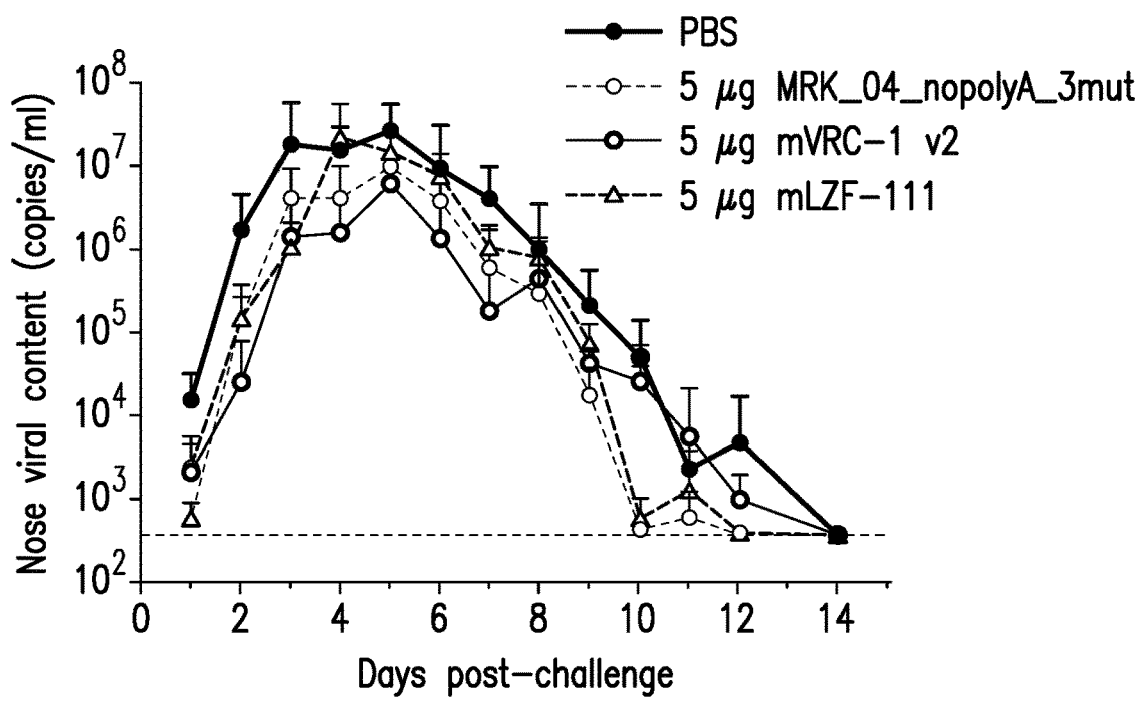
Figure 17C:
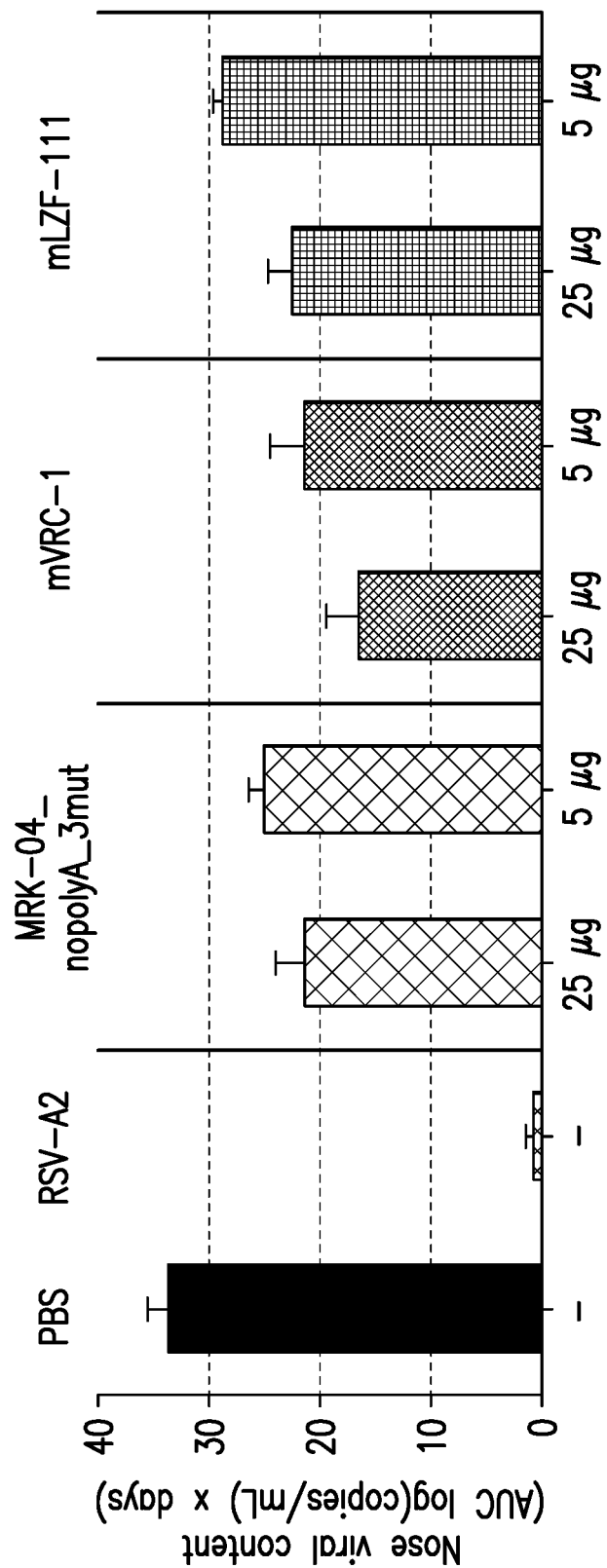

The mean RNA copy number detected in the nose samples are presented in FIGS. 17A-17C. The protective effect of all mRNA-based vaccines was less apparent in the nose, but again mVRC-1 (v2) demonstrated a 5-fold higher efficacy over MRK-04_nopolyA_3mut.

Example 6

Immunogenicity in RSV-Experienced African Green Monkeys

The immunogenicity of mRNA vaccines formulated in LNP was tested in RSV-experienced African Green Monkeys.

Healthy adult, African Green Monkeys of either sex (n=4 or 5/group), with body weights ranging from 2.85 to 4.65 kg, that were confirmed to be RSV seropositive by ELISA and neutralizing antibody titers, were selected for the study. The pool of animals selected for this study had been experimentally infected with RSV in previous studies and were distributed across study groups based on their pre study RSV neutralization titers so that all groups would have similar group GMTs at study start. RSV experienced animals provide a model of immune memory recall response to vaccination that may reflect the responses that can be anticipated in seropositive human adults, with the caveat that the antibody response in AGMs following RSV exposure is more biased towards postfusion F protein epitopes than the human immune repertoire.

A single vaccine dose was administered to each animal at week 0 by the intramuscular (IM) route. A control group receiving only PBS was also included in the study design.

Vaccines were administered as described in Table 2. After vaccination, the animals were observed daily for any changes at the inoculation site or other changes in activity or feeding habits that might indicate an adverse reaction to the vaccine but none were noted. Serum samples were collected for assessment of RSV neutralizing antibody titers, as well as palivizumab (site II), D25 (site $\phi$) and 4D7 (site I) competing antibody titers.

TABLE 2

Vaccine Formulations Tested for Immunogenicity in RSV Seropositive African Green Monkeys

| Group | Vaccine | Conc (µg/ml) | Dose (µg) |
| --- | --- | --- | --- |
| 1 | MRK-04_nopolyA_3mut, I.M. | 10 | 5 |
| 2 | mVRC-1 (v2), I.M. | 10 | 5 |
| 3 | mVRC-1 (v2), I.M | 2 | 1 |
| 4 | mLZF-111 | 10 | 5 |
| 5 | mLZF-111 | 2 | 1 |
| 6 | None (PBS) | NA | NA |

Figure 18:
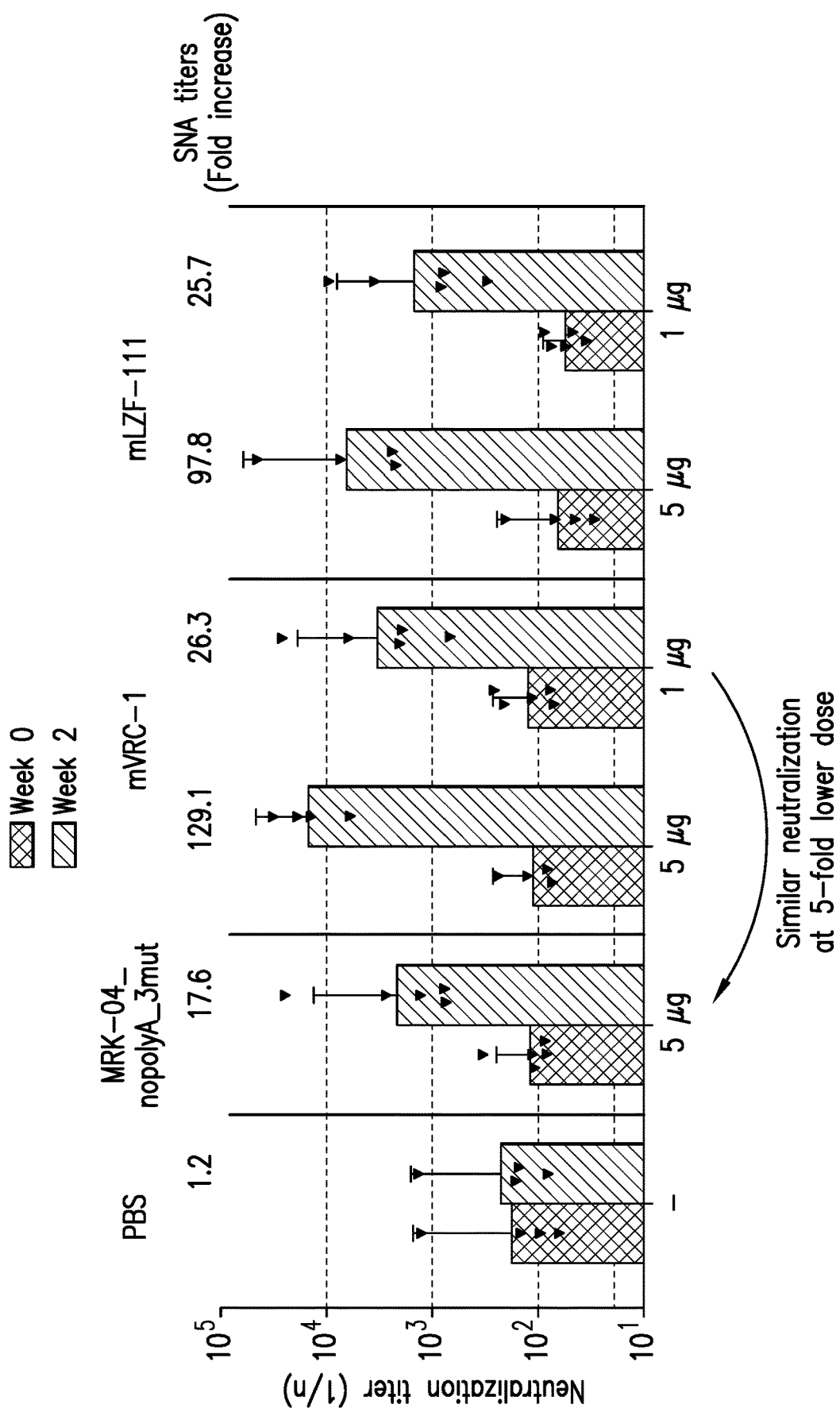
FIG. 18 sets forth serum neutralizing antibody titers ($NT_{50}$ Individual and GMT with 95% Confidence Intervals) to RSV A Experienced African Green Monkeys by mRNA vaccines and control formulations.

Individual animal $NT_{50}$ titers were measured in serum samples collected at baseline and 2 weeks post vaccination using methods described above and the results are shown in FIG. 18. All vaccines were found to be highly immunogenic as demonstrated by the increase in levels of serum antibodies binding RSV F proteins (both prefusion and postfusion RSV F, data not shown) and increases in serum neutralizing antibody levels. mVRC-1 (v2) induced the highest boost in neutralizing titers (>100 fold at the highest dose), and exhibited similar potency at a 5-fold lower dose relative to MRK-04_nopolyA_3mut. Similarly, mLZF-111 also demonstrated increased potency relative to MRK-04_nopolyA_3mut. No increase in titers was observed in the PBS control group.

Figure 19:
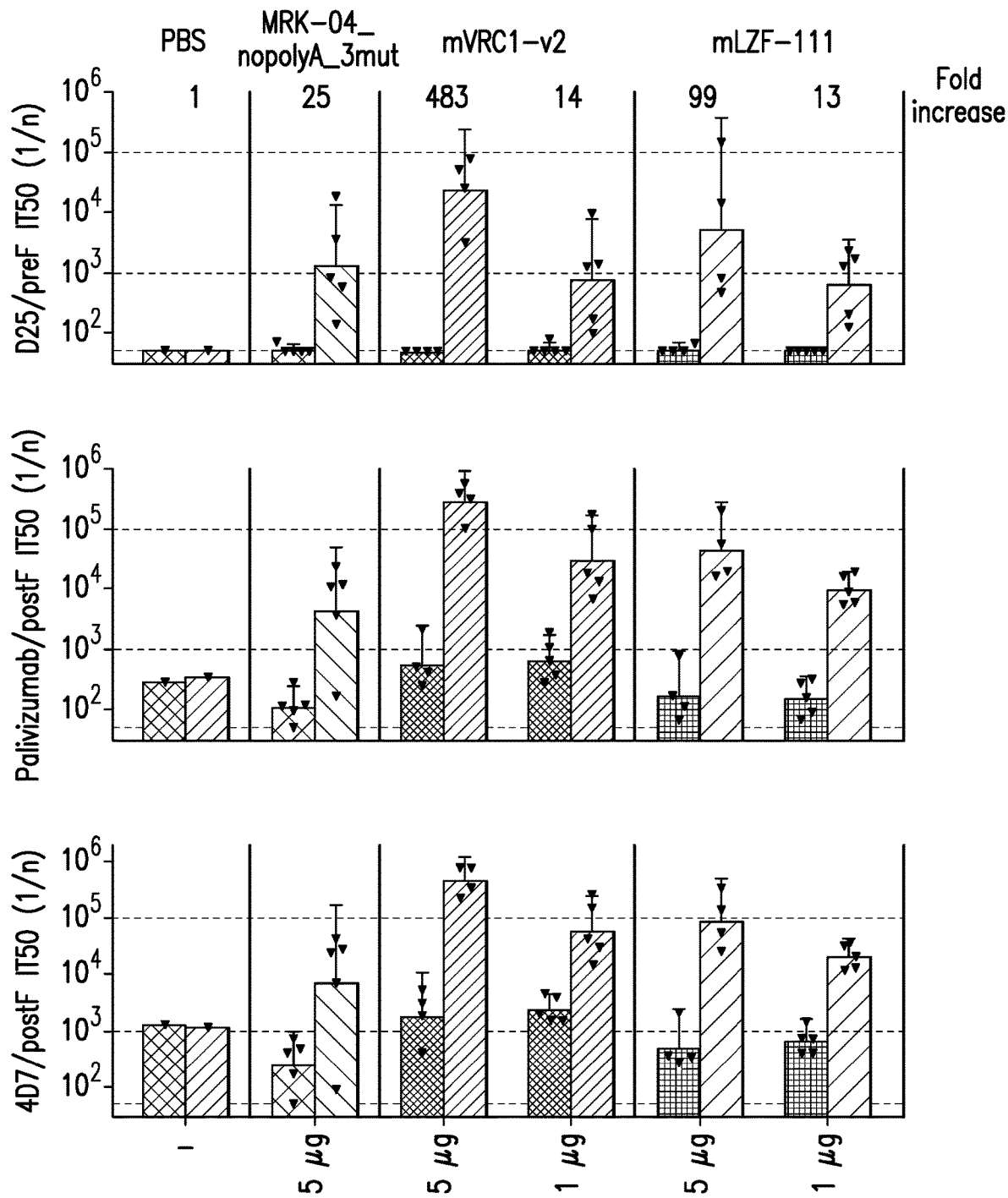
FIG. 19 sets forth serum antibody competition ELISA titers ($IT_{50}$ Individual and GMT with 95% Confidence intervals) against D25 (site φ), palivizumab (site II), and 4D7 (site I) measured at week 10 (2 weeks PD3).

To evaluate the quality of the boosted responses in the vaccinated animals, palivizumab (site II), D25 (site $\phi$) and 4D7 (site I) competing antibody titers were determined in serum collected at 2 weeks post vaccination (FIG. 19). As described above, antigenic site II is a neutralization epitope found on both the prefusion and the postfusion conformation of the F protein, site $\phi$ is a prefusion specific neutralization epitope and 4D7 is a postfusion specific epitope. Due to the baseline immune bias to the postfusion conformation, RSV-experienced AGMs do not have detectable D25-competing antibody titers prior to immunization. However, all three mRNA antigens induced high D25 competing antibodies titers, demonstrating that AGMs do mount an antigenic site $\phi$ immune response after RSV infection that can be boosted by immunization. The boost in D25 competing antibody titers following mVRC-1 (v2) immunization were the highest (>450 fold), and demonstrating again similar potency at a 5-fold lower dose than the MRK-04_nopolyA_3mut. In contrast to naive animals (cotton rats and AGMs) we observed a high boost of 4D7/post-F specific antibodies in RSV-experienced AGMs in the mVRC-1 (v2) group, demonstrating that the baseline antibody pool can determine the outcome of the epitope-specific antibody profile after immunization. Since the B cell memory pool from natural RSV infection in humans is thought to be strongly biased towards the prefusion conformation, we speculate mVRC-1 (v2) immunization in humans will boost preferentially antibodies against these epitopes, known to have more potent neutralizing activity, leading to increased efficacy over MRK-04_nopolyA_3mut.

TABLE 3

Sequence of amino acid linkers, TEV cleavage site, Thrombin Cleavage Site and Strep Tag

| Name | Sequence | SEQ ID NO: |
|---|---|---|
| 8 amino acid linker | GGGS GGGS | 1 |
| 10 amino acid linker | GGGS GGGS GG | 2 |
| 12 amino acid linker | GGGS GGGS GGGS | 3 |
| 14 amino acid linker | GGGS GGGS GGGS GS | 4 |
| Amino acid linker | GGGS | 49 |
| TEV Cleavage Site | ENLYFQS | 5 |
| Strep Tag | WSHPQFEK | 6 |
| Thrombin Cleavage Site | LVPRGS | 7 |
| Foldon | SAIGGYIPEAPRDGQAYVRKDGEWVLLSTFL | 8 |
| Signal Sequence | MELLILKANAITTILTAVTFCFASG | 9 |

TABLE 4

Antigenic Polypeptide Sequences

| Name | Sequence | SEQ ID NO: |
|---|---|---|
| RSV F protein reference sequence | MELLILKANAITTILTAVTFCFASGQNITEEFYQSTCSAVSKGYLSALRTGWYTSVITIELSNIKENKCNGTDAKVKLIKQELDKYKNAVTELQLLMQSTPPTNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEINLCNVDIFNPKYDCKIMTSKTDVSSSVITSLGAIVSCYGKTKCTASNKNRGIIKTFSNGCDYVSNKGMDTVSVGNTLYYVNKQEGKSLYVKGEPIINFYDPLVFPSDEFDASISQVNEKINQSLAFIRKSDELLHNVNAGKSTTNIMITTIIIVIIVILLSLIAVGLLLYCKARSTPVTLSKDQLSGINNIAFSN | 10 |
| RSV F WT Reference Sequence with a foldon domain (bold) replacing amino acids 514-574 of RSV F WT | MELLILKANAITTILTAVTFCFASGQNITEEFYQSTCSAVSKGYLSALRTGWYTSVITIELSNIKENKCNGTDAKVKLIKQELDKYKNAVTELQLLMQSTPATNNRARRELPRFMNYTLNNAKKTNVTLSKKRKRRFLGFLLGVGSAIASGVAVSKVLHLEGEVNKIKSALLSTNKAVVSLSNGVSVLTSKVLDLKNYIDKQLLPIVNKQSCSISNIETVIEFQQKNNRLLEITREFSVNAGVTTPVSTYMLTNSELLSLINDMPITNDQKKLMSNNVQIVRQQSYSIMSIIKEEVLAYVVQLPLYGVIDTPCWKLHTSPLCTTNTKEGSNICLTRTDRGWYCDNAGSVSFFPQAETCKVQSNRVFCDTMNSLTLPSEVNLCNVDIFNPKYDCKIMTSKTDVSSSVITSLGAIVSCYGKTKCTASNKNRGIIKTFSNGCDYVSNKGVDTVSVGNTLYYVNKQEGKSLYVKGEPIINFYDPLVFPSDEFDASISQVNEKINQSLAFIRKSDELLHNVNAGKSTTNIMITTGYIPEAPRDGQAYVRICDGEWVLLSTFL | 11 |

TABLE 4-continued

Antigenic Polypeptide Sequences

| Name | Sequence | SEQ ID NO: |
|---|---|---|
| RSV F WT ectodomain sequence (The sequence contains Foldon in bold, followed by a TEV cleavage site, a strep tag, a linker (underlined), a strep tag, another linker (underlined) and a His tag (italicized)) | MELLILKANAITTILTAVTFCFASGQNITEEFYQ STCSAVSKGYLSALRTGWYTSVITIELSNIKEN KCNGTDAKVKLIKQELDKYKNAVTELQLLMQ STPATNNRARRELPRFMNYTLNNAKKTNVTL SKKRKRRFLGFLLGVGSAIASGVAVSKVLHLE GEVNKIKSALLSTNKAVVSLSNGVSVLTSKVL DLKNYIDKQLLPIVNKQSCSISNIETVIEFQQKN NRLLEITREFSVNAGVTTPVSTYMLTNSELLSL INDMPITNDQKKLMSNNVQIVRQQSYSIMSIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLHNVNA GKSTTNIMITTGYIPEAPRDGQAYVRICDGEW VLLSTFLENLYFQSWSHPQFEKGGGSGGGSG GGSWSHPQFEKGSGSGS*HHHHHHHH* | 12 |
| DS-Cav1 peptide sequence (foldon sequence in bold) | MELLILKANAITTILTAVTFCFASGQNITEEFYQ STCSAVSKGYLSALRTGWYTSVITIELSNIKEN KCNGTDAKVKLIKQELDKYKNAVTELQLLMQ STPATNNRARRELPRFMNYTLNNAKKTNVTL SKKRKRRFLGFLLGVGSAIASGVAVCKVLHLE GEVNKIKSALLSTNKAVVSLSNGVSVLTFKVL DLKNYIDKQLLPILNKQSCSISNIETVIEFQQKN NRLLEITREFSVNAGVTTPVSTYMLTNSELLSL INDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLSAIGG YIPEAPRDGQAYVRICDGEWVLLSTFL | 13 |
| LZF 40: Sequence contains an 8 amino acid linker (bold and underlined), DS-Cav1 substitutions (S155C, S290C, S190F and V207L) and a c-terminal foldon (bold). | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSAIASGVAVCKVLHLEGEVNKIKS ALLSTNKAVVSLSNGVSVLTFKVLDLKNYIDK QLLPILNKQSCSISNIETVIEFQQKNNRLLEITR EFSVNAGVTTPVSTYMLTNSELLSLINDMPITN DQKKLMSNNVQIVRQQSYSIMCIIKEEVLAYV VQLPLYGVIDTPCWKLHTSPLCTTNTKEGSNI CLTRTDRGWYCDNAGSVSFFPQAETCKVQSN RVFCDTMNSLTLPSEVNLCNVDIFNPKYDCKI MTSKTDVSSSVITSLGAIVSCYGKTKCTASNK NRGIIKTFSNGCDYVSNKGVDTVSVGNTLYY VNKQEGKSLYVKGEPIINFYDPLVFPSDEFDAS ISQVNEKINQSLAFIRKSDELLSAIGGYIPEAP RDGQAYVRKDGEWVLLSTFL | 14 |
| LZF 40(a): Sequence contains an 8 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSAIASGVAVCKVLHLEGEVNKIKS ALLSTNKAVVSLSNGVSVLTFKVLDLKNYIDK QLLPILNKQSCSISNIETVIEFQQKNNRLLEITR EFSVNAGVTTPVSTYMLTNSELLSLINDMPITN DQKKLMSNNVQIVRQQSYSIMCIIKEEVLAYV VQLPLYGVIDTPCWKLHTSPLCTTNTKEGSNI CLTRTDRGWYCDNAGSVSFFPQAETCKVQSN RVFCDTMNSLTLPSEVNLCNVDIFNPKYDCKI MTSKTDVSSSVITSLGAIVSCYGKTKCTASNK NRGIIKTFSNGCDYVSNKGVDTVSVGNTLYY VNKQEGKSLYVKGEPIINFYDPLVFPSDEFDAS ISQVNEKINQSLAFIRKSDELLSAIGGYIPEAP RDGQAYVRKDGEWVLLSTFLGGLVPRGSH HHHHSAWSHPQFEK | 15 |

TABLE 4-continued

Antigenic Polypeptide Sequences

| Name | Sequence | SEQ ID NO: |
|---|---|---|
| LZF 55: Sequence contains a10 amino acid linker (bold and underlined), DS-Cav1 substitutions (S155C, S290C, S190F and V207L) and a c-terminal foldon (bold). | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGAIASGVAVCKVLHLEGEVNKI KSALLSTNKAVVSLSNGVSVLTFKVLDLKNYI DKQLLPILNKQSCSISNIETVIEFQQKNNRLLEI TREFSVNAGVTTPVSTYMLTNSELLSLINDMPI TNDQKKLMSNNVQIVRQQSYSIMCIIKEEVLA YVVQLPLYGVIDTPCWKLHTSPLCTTNTKEGS NICLTRTDRGWYCDNAGSVSFFPQAETCKVQ SNRVFCDTMNSLTLPSEVNLCNVDIFNPKYDC KIMTSKTDVSSSVITSLGAIVSCYGKTKCTASN KNRGIIKTFSNGCDYVSNKGVDTVSVGNTLY YVNKQEGKSLYVKGEPIINFYDPLVFPSDEFD ASISQVNEKINQSLAFIRKSDELLSAIGGYIPEA PRDGQAVVRICDGEWVLLSTFL | 16 |
| LZF 55a: Sequence contains a 10 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGAIASGVAVCKVLHLEGEVNKI KSALLSTNKAVVSLSNGVSVLTFKVLDLKNYI DKQLLPILNKQSCSISNIETVIEFQQKNNRLLEI TREFSVNAGVTTPVSTYMLTNSELLSLINDMPI TNDQKKLMSNNVQIVRQQSYSIMCIIKEEVLA YVVQLPLYGVIDTPCWKLHTSPLCTTNTKEGS NICLTRTDRGWYCDNAGSVSFFPQAETCKVQ SNRVFCDTMNSLTLPSEVNLCNVDIFNPKYDC KIMTSKTDVSSSVITSLGAIVSCYGKTKCTASN KNRGIIKTFSNGCDYVSNKGVDTVSVGNTLY YVNKQEGKSLYVKGEPIINFYDPLVFPSDEFD ASISQVNEKINQSLAFIRKSDELLSAIGGYIPEA PRDGQAYVRICDGEWVLLSTFLGGLVPRGSH HHHHHSAWSHPQFEK | 17 |
| LZF 56: Sequence contains a 12 amino acid linker (bold and underlined), DS-Cav1 substitutions (S155C, S290C, S190F and V207L), and a c-terminal foldon (bold). | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSAIASGVAVCKVLHLEGEV NKIKSALLSTNKAVVSLSNGVSVLTFKVLDLK NYIDKQLLPILNKQSCSISNIETVIEFQQKNNRL LEITREFSVNAGVTTPVSTYMLTNSELLSLIND MPITNDQKKLMSNNVQIVRQQSYSIMCIIKEE VLAYVVQLPLYGVIDTPCWKLHTSPLCTTNTK EGSNICLTRTDRGWYCDNAGSVSFFPQAETCK VQSNRVFCDTMNSLTLPSEVNLCNVDIFNPKY DCKIMTSKTDVSSSVITSLGAIVSCYGKTKCTA SNKNRGIIKTFSNGCDYVSNKGVDTVSVGNTL YYVNKQEGKSLYVKGEPIINFYDPLVFPSDEF DASISQVNEKINQSLAFIRKSDELLSAIGGYIPE APRDGQAYVRICDGEWVLLSTFL | 18 |
| LZF 56a Sequence contains a12 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSAIASGVAVCKVLHLEGEV NKIKSALLSTNKAVVSLSNGVSVLTFKVLDLK NYIDKQLLPILNKQSCSISNIETVIEFQQKNNRL LEITREFSVNAGVTTPVSTYMLTNSELLSLIND MPITNDQKKLMSNNVQIVRQQSYSIMCIIKEE VLAYVVQLPLYGVIDTPCWKLHTSPLCTTNTK EGSNICLTRTDRGWYCDNAGSVSFFPQAETCK VQSNRVFCDTMNSLTLPSEVNLCNVDIFNPKY DCKIMTSKTDVSSSVITSLGAIVSCYGKTKCTA SNKNRGIIKTFSNGCDYVSNKGVDTVSVGNTL YYVNKQEGKSLYVKGEPIINFYDPLVFPSDEF DASISQVNEKINQSLAFIRKSDELLSAIGGYIPE APRDGQAYVRICDGEWVLLSTFLGGLVPRGS HHHHHHSAWSHPQFEK | 19 |

TABLE 4-continued

Antigenic Polypeptide Sequences

| Name | Sequence | SEQ ID NO: |
|---|---|---|
| LZF 57: Sequence contains a14 amino acid linker (bold and underlined), DS-Cav1 substitutions (S155C, S290C, S190F and V207L), and a c-terminal foldon (bold). | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSGSAIASGVAVCKVLHLEG EVNKIKSALLSTNKAVVSLSNGVSVLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLSAIGG YIPEAPRDGQAYVRKDGEWVLLSTFL | 20 |
| LZF 57a: Sequence contains a 14 amino acid linker (bold and underlined), DS-Cav1 substitutions (S155C, S290C, S190F and V207L), a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSGSAIASGVAVCKVLHLEG EVNKIKSALLSTNKAVVSLSNGVSVLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLSAIGG YIPEAPRDGQAYVRKDGEWVLLSTFLGGLV PRGSHHHHHHSAWSHPQFEK | 21 |
| LZF 109 Sequence contains a 14 amino acid linker (bold and underlined), DS-Cav1 substitutions (S155C, S290C, S190F and V207L), additional mutations S180C and S186C (bold, italicized and underlined) and a c-terminal foldon (bold) | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSGSAIASGVAVCKVLHLEG EVNKIKSALLSTNKAVV*C*LSNGV*C*VLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLSAIGG YIPEAPRDGQAYVRKDGEWVLLSTFL | 22 |
| LZF 109a Sequence contains a 14 amino acid linker (bold and underlined), DS-Cav1 substitutions (S155C, S290C, S190F and V207L), additional mutations S180C and S186C (bold, italicized and underlined) and a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSGSAIASGVAVCKVLHLEG EVNKIKSALLSTNKAVV*C*LSNGV*C*VLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS DEFDASISQVNEKINQSLAFIRKSDELLSAIGG YIPEAPRDGQAYVRKDGEWVLLSTFLGGLV PRGSHHHHHHSAWSHPQFEK | 23 |
| LZF 110 Sequence contains a14 amino acid linker (bold and underlined), DS-Cav1 | MELLILKANAITTILTAVTFCFASGQNITEEFYQ STCSAVSKGYLSALRTGWYTSVITIELSNIKEN KCNGTDAKVKLIKQELDKYKNAVTELQLLM GGGSGGGSGGGSGSAIASGVAVCKVLHLEG | 24 |

TABLE 4-continued

Antigenic Polypeptide Sequences

| Name | Sequence | SEQ ID NO: |
|---|---|---|
| substitutions (S155C, S290C, S190F and V207L), additional mutations D486C and A490C (bold, italicized and underlined) and a c-terminal foldon (bold) | EVNKIKSALLSTNKAVVSLSNGVSVLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS *C*EFD*C*SISQVNEKINQSLAFIRKSDELLSAIGG YIPEAPRDGQAYVRKDGEWVLLSTFL  |   |
| LZF 110a Sequence contains a 14 amino acid linker (bold and underlined), DS-Cav1 substitutions (S155C, S290C, S190F and V207L), additional mutations D486C and A490C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEEFYQ STCSAVSKGYLSALRTGWYTSVITIELSNIKEN KCNGTDAKVKLIKQELDKYKNAVTELQLLMGGGSGGGSGGGSGSAIASGVAVCKVLHLEG EVNKIKSALLSTNKAVVSLSNGVSVLTFKVLD LKNYIDKQLLPILNKQSCSISNIETVIEFQQKNN RLLEITREFSVNAGVTTPVSTYMLTNSELLSLI NDMPITNDQKKLMSNNVQIVRQQSYSIMCIIK EEVLAYVVQLPLYGVIDTPCWKLHTSPLCTTN TKEGSNICLTRTDRGWYCDNAGSVSFFPQAET CKVQSNRVFCDTMNSLTLPSEVNLCNVDIFNP KYDCKIMTSKTDVSSSVITSLGAIVSCYGKTK CTASNKNRGIIKTFSNGCDYVSNKGVDTVSVG NTLYYVNKQEGKSLYVKGEPIINFYDPLVFPS *C*EFD*C*SISQVNEKINQSLAFIRKSDELLSAIGG YIPEAPRDGQAYVRKDGEWVLLSTFLGGLV PRGSHHHHHHSAWSHPQFEK | 25 |
| LZF 111 Sequence contains a14 amino acid linker (bold and underlined), DS-Cav1 substitutions (S155C, S290C, S190F and V207L), additional mutations D486C and D489C (bold, italicized and underlined) and a c-terminal foldon (bold) | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPS*C*EF*C*ASISQVNEKINQSLAFIR KSDELLSAIGGYIPEAPRDGQAYVRKDG EWVLLSTFL | 26 |
| LZF 111a Sequence contains a14 amino acid linker (bold and underlined), DS-Cav1 substitutions (S155C, S290C, S190F and V207L), additional mutations D486C and D489C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTFKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPS*C*EF*C*ASISQVNEKINQSLAFIR KSDELLSAIGGYIPEAPRDGQAYVRKDG EWVLLSTFLGGLVPRGSHHHHHHSAWSH PQFEK | 27 |
| LZF 112 Sequence contains a 14 amino acid linker (bold and underlined), DS-Cav1 substitutions (S155C, | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL | 28 |

TABLE 4-continued

Antigenic Polypeptide Sequences

| Name | Sequence | SEQ ID NO: |
|---|---|---|
| S290C, S190F and V207L), additional mutations L512C and L513C (bold, italicized and underlined) and a c-terminal foldon (bold) | SNGVSVLTPKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDE_CC_SAIGGYIPEAPRDGQAYVRKDG EWVLLSTFL | |
| LZF 112a Sequence contains a 14 amino acid linker (bold and underlined), DS-Cav1 substitutions (S155C, S290C, S190F and V207L), additional mutations L512C and L513C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTPKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLAFIR KSDE_CC_SAIGGYIPEAPRDGQAYVRKDG EWVLLSTFLGGLVPRGSHHHHHHSAWSH PQFEK | 29 |
| LZF 113 Sequence contains a 14 amino acid linker (bold and underlined), DS-Cav1 substitutions (S155C, S290C, S190F and V207L), additional mutation F505C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTPKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLA_C_IR KSDELLSAIGGYIPEAPRDGQAYVRKDG EWVLLSTFL | 30 |
| LZF 113a Sequence contains a 14 amino acid linker (bold and underlined), DS-Cav1 substitutions (S155C, S290C, S190F and V207L), additional imitation F505C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMGGGSGGGSGGGSGSAIASGV AVCKVLHLEGEVNKIKSALLSTNKAVVSL SNGVSVLTPKVLDLKNYIDKQLLPILNKQS CSISNIETVIEFQQKNNRLLEITREFSVNAG VTTPVSTYMLTNSELLSLINDMPITNDQKK LMSNNVQIVRQQSYSIMCIIKEEVLAYVV QLPLYGVIDTPCWKLHTSPLCTTNTKEGS NICLTRTDRGWYCDNAGSVSFFPQAETCK VQSNRVFCDTMNSLTLPSEVNLCNVDIFN PKYDCKIMTSKTDVSSSVITSLGAIVSCYG KTKCTASNKNRGIIKTFSNGCDYVSNKGV DTVSVGNTLYYVNKQEGKSLYVKGEPIIN FYDPLVFPSDEFDASISQVNEKINQSLA_C_IR KSDELLSAIGGYIPEAPRDGQAYVRKDG EWVLLSTFLGGLVPRGSHHHHHHSAWSH PQFEK | 31 |

TABLE 4-continued

Antigenic Polypeptide Sequences

| Name | Sequence | SEQ ID NO: |
|---|---|---|
| LZF 123<br>Sequence contains DS-Cav1 substitutions (S155C, S290C, S190F and V207L) and additional substitutions S180C and S186C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVV*C*LSNGV*C*VLTFKVLDLKNYIDKQLLP ILNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPSDEFDASISQVNEKINQSL AFIRKSDELLSAIGGYIPEAPRDGQAYVR KDGEWVLLSTFL | 32 |
| LZF 123a<br>Sequence contains DS-Cav1 substitutions (S155C, S290C, S190F and V207L) and additional substitutions S180C and S186C (bold, italicized and underlined), a c-terminal foldon (bold), a GG linker (underlined), a thrombin cleavage site, a His tag, a SA linker (underlined) and a strep tag. | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVV*C*LSNGV*C*VLTFKVLDLKNYIDKQLLP ILNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPSDEFDASISQVNEKINQSL AFIRKSDELLSAIGGYIPEAPRDGQAYVR KDGEWVLLSTFLGGLVPRGSHHHHHHS AWSHPQFEK | 33 |
| LZF124<br>Sequence contains DS-Cav1 substitutions (S155C, S290C, S190F and V207L) and additional substitutions D486C and A490C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPS*C*EFD*C*SISQVNEKINQSL AFIRKSDELLSAIGGYIPEAPRDGQAYVR KDGEWVLLSTFL | 34 |
| LZF 124 a<br>Sequence contains DS-Cav1 substitutions (S155C, S290C, S190F and V207L), additional substitutions D486C and A490C (bold, italicized and underlined) and a c-terminal foldon (bold), a GG linker | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT | 35 |

TABLE 4-continued

Antigenic Polypeptide Sequences

| Name | Sequence | SEQ ID NO: |
|---|---|---|
| (underlined), a thrombin cleavage site, a His tag, a SA linker (underlined) and a strep tag. | NDQKKLMSNNVQIVRQQSYSIMCIIKEEV LAYVVQLPLYGVIDTPCWKLHTSPLCTTN TKEGSNICLTRTDRGWYCDNAGSVSFFPQ AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLVFPS*C*EFD*C*SISQVNEKINQSL AFIRKSDELLSAIGGYIPEAPRDGQAYVR KDGEWVLLSTFLGGLVPRGSHHHHHHS AWSHPQFEK | |
| LZF 125<br>Sequence contains DS-Cav1 substitutions (S155C, S290C, S190F and V207L) and additional substitutions D486C and D489C (bold, italicized and underlined) and a c-terminal foldon (bold). | MELLILKANAITTILTAVTFCFASGQNITEE FYQSTCSAVSKGYLSALRTGWYTSVITIEL SNIKENKCNGTDAKVKLIKQELDKYKNA VTELQLLMQSTPATNNRARRELPRFMNYT LNNAKKTNVTLSKKRKRRFLGFLLGVGSA IASGVAVCKVLHLEGEVNKIKSALLSTNK AVVSLSNGVSVLTFKVLDLKNYIDKQLLPI LNKQSCSISNIETVIEFQQKNNRLLEITREF SVNAGVTTPVSTYMLTNSELLSLINDMPIT NDQKK TABLE 4-continued Antigenic Polypeptide Sequences

| Name | Sequence | SEQ ID NO: |
|---|---|---|
| LZF 126a<br>Sequence contains DS-Cav1 substitutions (S155C, S290C, S190F and V207L), additional substitutions L512C and L513C (bold, italicized and underlined), a c-terminal foldon (bold), a GG linker (underlined), a thrombin cleavage site, a His tag, a SA linker (underlined) and a strep tag. | MEL

TABLE 4-continued

Antigenic Polypeptide Sequences

| Name | Sequence | SEQ ID NO: |
|---|---|---|
| | AETCKVQSNRVFCDTMNSLTLPSEVNLCN VDIFNPKYDCKIMTSKTDVSSSVITSLGAIV SCYGKTKCTASNKNRGIIKTFSNGCDYVS NKGVDTVSVGNTLYYVNKQEGKSLYVKG EPIINFYDPLSAIGGYIPEAPRDGQAYVRK DGEWVLLSTFL | |
| LZF 128 a<br>Sequence contains DS-Cav1 substitutions (S155C, S290C, S190F and V207L), additional deletion of HRB domain corresponding to amino acids 482-513, a c-terminal foldon (bold), a linker (underlined), a thrombin cleavage site, a His tag, a linker (underlined) and a strep tag. | MELLILKANAITTILTAVTFCFASGQNITEE FY

| Primers | Sequences |
|---|---|
| RSV A F N gene | 5' CTC AAT TTC CTC ACT TCT CCA GTG T (SEQ ID NO: 46) |
| RSV A R N gene | 5' CTT GAT TCC TCG GTG TAC CTC TGT (SEQ ID NO: 47) |
| RSV A FAM N gene | 5'FAM-TCC CAT TAT GCC TAG GCC AGC AGC A (BHQ1) (SEQ ID NO: 48) |

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A recombinant respiratory syncytial virus (RSV) F protein trimer, comprising: an amino acid sequence set forth in any one of SEQ ID NOS: 22, 23, 24, 25, 26, 27, 28, 29, 30, 31, 44, or 45.

2. An RSV immunogenic composition comprising the recombinant RSV F protein trimer of claim 1 and a pharmaceutically acceptable excipient.

3. The immunogenic composition of claim 2 formulated in an effective amount to produce an antigen-specific immune response directed against the recombinant RSV F trimer or the recombinant RSV F peptide.

4. The immunogenic composition of claim 2 that is formulated with an adjuvant.

5. The immunogenic composition of claim 4, wherein the adjuvant is an aluminum adjuvant.

6. The immunogenic composition of claim 5, wherein the aluminum adjuvant is amorphous aluminum hydroxyphosphate sulfate or an aqueous suspension of aluminum hydroxyphosphate.

7. The immunogenic composition of claim 2 further comprising a lipid nanoparticle comprising one or more cationic lipids and a poly(ethyleneglycol)-lipid (PEG lipid).

8. The immunogenic composition of claim 7, wherein the one or more cationic lipids are ionizable cationic lipids.

9. The immunogenic composition of claim 8, wherein the ionizable cationic lipids are selected from DLinDMA; DlinKC2DMA; DLin-MC3-DMA; CLinDMA; S-Octyl CLinDMA;

(2 S)-1-{7-[(3 β)-cholest-5-en-3-yloxy]heptyloxy}-3-[(4 Z)-dec-4-en-1-yloxy]-N, N-dimethylpropan-2-amine;
(2 R)-1-{4-[(3β)-cholest-5-en-3-yloxy]butoxy}-3-[(4 Z)-dec-4-en-1-yloxy]-N, N-dimethylpropan-2-amine;
1-[(2 R)-1-{7-[(3 β)-cholest-5-en-3-yloxy]butoxy}-3-(octyloxy)propan-2-yl]guanidine;
1-[(2 R)-1-{7-[(3 β)-cholest-5-en-3-yloxy]heptyloxy}-N, N-dimethyl-3-[(9 Z, 12 Z)-octadeca-9,12-dien-1-yl]oxy]propan-2-amine;
1-[(2 R)-1-{4-[(3 β)-cholest-5-en-3-yl]oxy]butoxy}-N,N-dimethyl-3-[(9 Z, 12 Z)-octadeca-9,12-dien-1-yloxy]propan-2-amine;
(2S)-1-({6-[(3 β)-cholest-5-en-3-yloxy]hexyl}oxy)-N,N-dimethyl-3-[(9 Z)-octadec-9-en-1-yloxy]propan-2-amine;
(3β)-3-[6-{[(2S)-3-[(9Z)-octadec-9-en-1-yloxy]]-2-(pyrrolidin-1-yl)propyl]oxy}hexyl)oxy]cholest-5-ene;
(2R)-1-({4-[(3β)-cholest-5-en-3-yloxy]butoxy}-3-(octyloxy)propan-2-amine;
(2R)-1-({8-[(3β)-cholest-5-en-3-yloxy]octyl}oxy)-N,N-dimethyl-3-(pentyloxy)propan-2-amine;
(2R)-1-({8-[(3β)-cholest-5-en-3-yloxyl]octyl}oxy)-3-(heptyloxy)-N,N-dimethylpropan-2-amine;
(2R)-1-({8-[(3β)-cholest-5-en-3-yloxy]octyl}oxy)-N,N-dimethyl-3-[(2Z)-pent-2-en-1-yloxy]propan-2-amine;
(2S)-1-butoxy-3-({8-[(3β)-cholest-5-en-3-yloxy]octyl}oxy)-N,N-dimethylpropan-2-amine;
(2S-1-({8-[(3β)-cholest-5-en-3-yloxy]octyl}oxy)-[2,2,3,3,4,4,5,5,6,6,7,7,8,8,9,9-hexadecafluorononyl)oxy]-N,N-dimethylpropan-2-amine;
2-amino-2-{[(9Z,12Z)-octadeca-9,12-dien-1-yloxy]methyl}propane-1,3-diol;
2-amino-3-((9-(((3S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)nonyl)oxy)-2-((((9Z,12Z)-octadeca-9,12-dien-1-yl)oxy)methyl)propan-1-ol;
2-amino-3-((6-(((3 S,10R,13R)-10,13-dimethyl-17-(6-methylheptan-2-yl)-2,3,4,7,8,9,10,11,12,13,14,15,16,17-tetradecahydro-1H-cyclopenta[a]phenanthren-3-yl)oxy)hexyl)oxy)-2-((((Z)-octadec-9-en-1-yl)oxy)methyl)propan-1-ol;
(20Z,23Z)-N,N-dimethylnonacosa-20,23-dien-10-amine;
(17Z,20Z)-N,N-dimethylhexacosa-17,20-dien-9-amine;
(16Z,19Z)-N,N-dimethylpentacosa-16,19-dien-8-amine;
(13Z,16Z)-N,N-dimethyldocosa-13,16-dien-5-amine;
(12Z,15Z)-N,N-dimethylhenicosa-12,15-dien-4-amine;
(14Z,17Z)-N,N-dimethyltricosa-14,17-dien-6-amine;
(15Z,18Z)-N,N-dimethyltetracosa-15,18-dien-7-amine;
(18Z,21Z)-N,N-dimethylheptacosa-18,21-dien-10-amine;
(15Z,18Z)-N,N-dimethyltetracosa-15,18-dien-5-amine;
(14Z,17Z)-N,N-dimethyltricosa-14,17-dien-4-amine;
(19Z,22Z)-N,N-dimethyloctacosa-19,22-dien-9-amine;
(18Z,21Z)-N,N-dimethylheptacosa-18,21-dien-8-amine;
(17Z,20Z)-N,N-dimethylhexacosa-17,20-dien-7-amine;
(16Z,19Z)-N,N-dimethylpentacosa-16,19-dien-6-amine;
(22Z,25Z)-N,N-dimethylhentriaconta-22,25-dien-10-amine;
(21Z,24Z)-N,N-dimethyltriaconta-21,24-dien-9-amine;
(18Z)-N,N-dimethylheptacos-18-en-10-amine;
(17Z)-N,N-dimethylhexacos-17-en-9-amine;
(19Z,22Z)-N,N-dimethyloctacosa-19,22-dien-7-amine;
N,N-dimethylheptacosan-10-amine;
(20Z,23Z)-N-ethyl-N-methylnonacosa-20,23-dien-10-amine;
1-[(11Z,14Z)-1-nonylicosa-11,14-dien-1-yl]pyrrolidine;
(20Z)-N,N-dimethylheptacos-20-en-10-amine;
(15Z)-N,N-dimethylheptacos-15-en-10-amine;
(14Z)-N,N-dimethylnonacos-14-en-10-amine;
(17Z)-N,N-dimethylnonacos-17-en-10-amine;
(24Z)-N,N-dimethyltritriacont-24-en-10-amine;
(20Z)-N,N-dimethylnonacos-20-en-10-amine;
(22Z)-N,N-dimethylhentriacont-22-en-10-amine;
(16Z)-N,N-dimethylpentacos-16-en-8-amine;
(12Z,15Z)-N,N-dimethyl-2-nonylhenicosa-12,15-dien-1-amine;
(13Z,16Z)-N,N-dimethyl-3-nonyldocosa-13,16-dien-1-amine;
N,N-dimethyl-1-[(1S,2R)-2-octylcyclopropyl]heptadecan-8-amine;
1-[(1S,2R)-2-hexylcyclopropyl]-N,N-dimethylnonadecan-10-amine;

N,N-dimethyl-1-[(1S,2R)-2-octylcyclopropyl]nonadecan-10-amine;

N,N-dimethyl-21-[(1S,2R)-2-octylcyclopropyl]henicosan-10-amine;

N,N-dimethyl-1-[(1S,2S)-2-{[(1R,2R)-2-pentylcyclopropyl]methyl}cyclopropyl]nonadecan-10-amine;

N,N-dimethyl-1-[(1S,2R)-2-octylcyclopropyl]hexadecan-8-amine;

N,N-dimethyl-1-[(1R,2S)-2-undecylcyclopropyl]tetradecan-5-amine;

N,N-dimethyl-3-{7-[(1S,2R)-2-octylcyclopropyl]heptyl}dodecan-1-amine;

1-[(1R,2S)-2-heptylcyclopropyl]-N,N-dimethyloctadecan-9-amine;

1-[(1S,2R)-2-decylcyclopropyl]-N,N-dimethylpentadecan-6-amine;

N,N-dimethyl-1-[(1S,2R)-2-octylcyclopropyl]pentadecan-8-amine; and (11E,20Z,23Z)-N,N-dimethylnonacosa-11,20,23-trien-10-amine;

or a pharmaceutically acceptable salt thereof, or a stereoisomer of any of the foregoing.

10. The immunogenic composition of claim 7, further comprising one or more non-cationic lipids selected from a phospholipid, a phospholipid derivative, a fatty acid, sterol, or a combination thereof.

11. The immunogenic composition of claim 10, which comprises 34-59 mole % ionizable cationic lipids selected from the group consisting of (2S)-1-({6-[(3β))-cholest-5-en-3-yloxy]hexyl}oxy)-N,N-dimethyl-3-[(9 Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine, 30-48 mole % cholesterol, 10-24% DSPC and 1-2 mole % PEG-DMG.

12. A method of producing an immune response to RSV F protein in a subject, the method comprising administering to the subject an effective amount of the RSV F protein trimer of claim 1.

13. The method of claim 12, wherein the subject is administered a single dose of the RSV F protein trimer.

14. The method of claim 12, wherein the subject is administered at least one booster dose of the RSV F protein trimer.

15. The method of claim 12, wherein the RSV F protein trimer is administered to the subject by intradermal injection or intramuscular injection.

16. The method of claim 12, wherein the subject has been exposed to RSV, wherein the subject is infected with RSV, or wherein the subject is at risk of infection by RSV.

* * * * *